US012599582B2

(12) United States Patent
Vendeville et al.

(10) Patent No.: US 12,599,582 B2
(45) Date of Patent: Apr. 14, 2026

(54) PYRROLE COMPOUNDS

(71) Applicant: ALIGOS THERAPEUTICS, INC., South San Francisco, CA (US)

(72) Inventors: Sandrine Vendeville, Brussels (BE); David Bernard Smith, San Mateo, CA (US); Leonid Beigelman, San Mateo, CA (US); Vladimir Serebryany, Burlingame, CA (US)

(73) Assignee: Aligos Therapeutics, Inc., South San Francisco, CA (US)

(*) Notice: Subject to any disclaimer, the term of this patent is extended or adjusted under 35 U.S.C. 154(b) by 48 days.

(21) Appl. No.: 18/453,887

(22) Filed: Aug. 22, 2023

(65) Prior Publication Data

US 2023/0390242 A1 Dec. 7, 2023

Related U.S. Application Data

(63) Continuation of application No. 17/455,178, filed on Nov. 16, 2021, now Pat. No. 11,771,680, which is a continuation of application No. 16/837,515, filed on Apr. 1, 2020, now Pat. No. 11,191,747.

(60) Provisional application No. 62/932,686, filed on Nov. 8, 2019, provisional application No. 62/828,919, filed on Apr. 3, 2019.

(51) Int. Cl.

| | |
|---|---|
| ***A61K 31/4025*** | (2006.01) |
| ***A61K 31/40*** | (2006.01) |
| ***A61K 31/4192*** | (2006.01) |
| ***C07D 207/34*** | (2006.01) |
| ***C07D 401/12*** | (2006.01) |
| ***C07D 403/12*** | (2006.01) |
| ***C07D 405/12*** | (2006.01) |
| ***C07D 409/12*** | (2006.01) |
| ***C07D 487/04*** | (2006.01) |

(52) U.S. Cl.

CPC .......... *A61K 31/4025* (2013.01); *A61K 31/40* (2013.01); *A61K 31/4192* (2013.01); *C07D 207/34* (2013.01); *C07D 401/12* (2013.01); *C07D 403/12* (2013.01); *C07D 405/12* (2013.01); *C07D 409/12* (2013.01); *C07D 487/04* (2013.01)

(58) Field of Classification Search

CPC ............................ C07D 207/34; C07D 405/12

See application file for complete search history.

(56) References Cited

U.S. PATENT DOCUMENTS

| | | | |
|---|---|---|---|
| 7,732,446 | B1 | 6/2010 | Gwaltney et al. |
| 10,752,584 | B2 | 8/2020 | Schinazi et al. |
| 11,191,747 | B2 | 12/2021 | Vendeville et al. |
| 11,771,680 | B2 | 10/2023 | Vendeville et al. |
| 2003/0119817 | A1 | 6/2003 | Mehta et al. |
| 2005/0288286 | A1 | 12/2005 | Flynn et al. |
| 2006/0102471 | A1 | 5/2006 | Maurer et al. |
| 2006/0105355 | A1 | 5/2006 | Maurer |
| 2007/0065877 | A1 | 3/2007 | Maurer |
| 2007/0191336 | A1 | 8/2007 | Flynn et al. |
| 2010/0234379 | A1 | 9/2010 | Bahr et al. |
| 2011/0312953 | A1 | 12/2011 | Fischer et al. |
| 2014/0256773 | A1 | 9/2014 | Gandhi |
| 2016/0166679 | A1 | 6/2016 | Low et al. |
| 2017/0127667 | A1 | 5/2017 | Gulba |
| 2020/0268730 | A1 | 8/2020 | Last et al. |
| 2020/0323821 | A1 | 10/2020 | Vendeville et al. |
| 2021/0017154 | A1 | 1/2021 | Zhang et al. |
| 2022/0071957 | A1 | 3/2022 | Vendeville et al. |
| 2022/0184035 | A1 | 6/2022 | Gou et al. |
| 2023/0056135 | A1 | 2/2023 | Schinazi et al. |

FOREIGN PATENT DOCUMENTS

| | | |
|---|---|---|
| AU | 2005221959 | 9/2005 |
| CL | 201503370 | 5/2016 |
| CL | 201600153 | 7/2016 |
| CL | 201802549 | 12/2018 |
| CL | 201900473 | 7/2019 |
| CL | 201901976 | 12/2019 |
| CN | 104672221 | 6/2015 |
| CN | 105431413 A | 3/2016 |
| CN | 108250122 | 7/2018 |
| CN | 109153640 A | 1/2019 |
| CN | 113454077 A | 9/2021 |
| GB | 2398299 | 8/2004 |
| IN | 2001DE00827 | 3/2005 |
| JP | 2016-539924 | 12/2016 |
| JP | 2018-150360 | 9/2018 |
| JP | 2019-507774 | 3/2019 |
| JP | 2021-519325 | 8/2021 |

(Continued)

OTHER PUBLICATIONS

Office Action dated Mar. 25, 2024 for JP Application No. 2021-559054, filed Apr. 1, 2020.

(Continued)

*Primary Examiner* — Kamal A Saeed

(74) *Attorney, Agent, or Firm* — Knobbe, Martens, Olson & Bear, LLP

(57) ABSTRACT

Provided herein are compounds of Formula (I), or pharmaceutically acceptable salts thereof, pharmaceutical compositions that include a compound described herein (including pharmaceutically acceptable salts of a compound described herein) and methods of synthesizing the same. Also provided herein are methods of treating diseases and/or conditions with a compound of Formula (I), or a pharmaceutically acceptable salt thereof.

2 Claims, 1 Drawing Sheet

Specification includes a Sequence Listing.

(56) References Cited

FOREIGN PATENT DOCUMENTS

| | | | |
|---|---|---|---|
| JP | 2022-508642 | | 1/2022 |
| JP | 2022-521081 | | 4/2022 |
| KR | 2017013629 | | 2/2017 |
| KR | 2017013630 | | 2/2017 |
| KR | 10-2018-0119669 | | 11/2018 |
| TW | 202045499 | A | 12/2020 |
| UZ | 5735 | C | 1/2019 |
| WO | WO 87/05926 | | 10/1987 |
| WO | WO 2002/006278 | | 1/2002 |
| WO | WO 2002/085908 | | 10/2002 |
| WO | WO 2003/013509 | | 2/2003 |
| WO | WO 2004/058164 | | 7/2004 |
| WO | WO 2005/087762 | | 9/2005 |
| WO | WO 2006/092059 | | 9/2006 |
| WO | WO 2008/033562 | | 3/2008 |
| WO | WO 2008/149382 | | 12/2008 |
| WO | WO 2008/155022 | | 12/2008 |
| WO | WO 2010/102238 | | 9/2010 |
| WO | WO 2011/050316 | | 4/2011 |
| WO | WO 2011/143466 | | 11/2011 |
| WO | WO 2011/157653 | | 12/2011 |
| WO | WO 2012/036573 | | 3/2012 |
| WO | WO 2012/047525 | | 4/2012 |
| WO | WO 2012/078902 | | 6/2012 |
| WO | WO 2012/087976 | | 6/2012 |
| WO | WO 2012/154880 | | 11/2012 |
| WO | WO 2012/154888 | | 11/2012 |
| WO | WO 2012/154967 | | 11/2012 |
| WO | WO 2013/006394 | | 1/2013 |
| WO | WO 2013/109991 | | 7/2013 |
| WO | WO 2014/047328 | | 3/2014 |
| WO | WO 2014/184350 | | 11/2014 |
| WO | WO 2015/011281 | | 1/2015 |
| WO | WO 2015/059212 | | 4/2015 |
| WO | WO 2015/134539 | | 9/2015 |
| WO | WO 2015/189331 | | 12/2015 |
| WO | WO 2017/081615 | | 5/2017 |
| WO | WO 2017/156255 | | 9/2017 |
| WO | WO 2018/039531 | | 3/2018 |
| WO | WO 2018/121689 | | 7/2018 |
| WO | WO 2020/072955 | | 4/2020 |
| WO | WO 2020/169784 | | 8/2020 |
| WO | WO 2020/205934 | | 10/2020 |
| WO | WO 2021/093172 | | 5/2021 |
| WO | WO 2022/143610 | | 7/2022 |

OTHER PUBLICATIONS

Rejection Decision dated Apr. 24, 2024, for Chinese Application No. 202080028131.4, filed Apr. 1, 2020.

Office Action dated Aug. 27, 2024 for JP Application No. 2021-559054, filed Apr. 1, 2020.

Office Action dated Jul. 16, 2024 for MX Application No. MX/a/2021/012105, filed Apr. 1, 2020.

Office Action mailed Jun. 13, 2024 for UA Application No. 2021 05907, filed Apr. 1, 2020.

Office Action mailed Jun. 12, 2024 for UZ Application No. IAP 2021 0514, filed Apr. 1, 2020.

Examination and Search Reports dated Nov. 15, 2024 for United Arab Emirates Application No. P6001788/2021, filed Nov. 16, 2021.

Examination Report dated Jan. 14, 2025 for Australian Patent Application No. 2020253444, filed Apr. 1, 2020.

Search Report and Opinion dated Feb. 25, 2025 for Brazilian Patent Application No. BR112021019817-2, filed Apr. 1, 2020.

Office Action dated Apr. 11, 2025, for Colombian Application No. NC2021/0014210, filed Apr. 1, 2020.

Communication dated Apr. 24, 2025 for EP Application No. 20784496.0, filed Apr. 1, 2020.

Office Action dated Apr. 7, 2025 for KR Application No. 10-2021-7035886, filed Apr. 1, 2020.

Office Action dated Sep. 24, 2024 for MX Application No. MX/a/2021/012105, filed Apr. 1, 2020.

Office Action dated Feb. 7, 2025 for MX Application No. MX/a/2021/012105, filed Apr. 1, 2020.

Examination Report dated Feb. 24, 2025 for PH Application No. 1-2021-552513, filed Apr. 1, 2020.

Search Report dated Aug. 28, 2023 for ARIPO Application No. AP/P/2021/013514, filed Apr. 1, 2020.

Examiner's Report and Search Report dated Nov. 14, 2023 for CL Application No. 202102575, filed Apr. 1, 2020.

Office Action dated Dec. 14, 2023, for Chinese Application No. 202080028131.4, filed Apr. 1, 2020.

Office Action dated Mar. 18, 2024 for Israeli Application No. 286902, filed Apr. 1, 2020.

Written Opinion dated Feb. 29. 2024 for SG Application No. 11202110718P, filed Apr. 1, 2020.

Office Action and Search Report completed Nov. 1, 2023 for TW Application No. 109111398, filed Apr. 1, 2020.

Communication dated Oct. 25, 2023 for EP Application No. 20784496.0, filed Apr. 1, 2020.

Office Action dated Nov. 19, 2023 for Georgian Application No. 15762/1, filed Apr. 1, 2020.

Second Examination Report dated Nov. 7, 2022 for Indian Patent Application No. 202117049271, filed Apr. 1, 2020.

"IUPAC-IUB Commission on Biochemical Nomenclature Abbreviated Nomenclature of Synthetic Polypeptides (Polymerized Amino Acids) Revised Recommendations (1971)" *Biochemistry*. (1972) 11(5) :942-944.

Liang, "Hepatitis B: The Virus and Disease" Hepatology (2009) 49(S5):S13-S21.

International Search Report and Written Opinion mailed Jun. 24, 2020 for PCT Application No. PCT/US2020/026116, filed Apr. 1, 2020.

Second Written Opinion mailed Feb. 26, 2021 for PCT Application No. PCT/US2020/026116, filed Apr. 1, 2020.

International Preliminary Report on Patentability mailed Jul. 28, 2021 for PCT Application No. PCT/US2020/026116, filed Apr. 1, 2020.

Office Action dated Apr. 26, 2021 for U.S. Appl. No. 16/837,515, filed Apr. 1, 2020.

Examination Report dated Mar. 10, 2022 for Indian Patent Application No. 202117049271, filed Apr. 1, 2020.

Opposition dated Apr. 19, 2022, for Colombian Application No. NC2021/0014210, filed Apr. 1, 2020.

Extended European Search Report dated Oct. 21, 2022 for EP Application No. 20784496.0, filed Apr. 1, 2020.

Office Action dated Apr. 17, 2023 for Eurasian Application No. 202192569, filed Apr. 1, 2020.

Office Action dated Nov. 10, 2022 for Georgian Application No. 15762/1, filed Apr. 1, 2020.

Examiner's Report and Search Report dated May 16, 2023 for CL Application No. 202102575, filed Apr. 1, 2020.

Office Action dated Jun. 1, 2023, for Chinese Application No. 202080028131.4, filed Apr. 1, 2020.

Office Action dated Feb. 6, 2023 for U.S. Appl. No. 17/455,178, filed Nov. 16, 2021.

Office Action dated Aug. 24, 2023 for Indonesian Application No. P00202108226, filed Apr. 1, 2020.

Examination Report dated May 14, 2025 for CA Application No. 3,134,635, filed Apr. 1, 2020.

Office Action dated Aug. 7, 2025 for Indonesian Application No. P00202108226, filed Apr. 1, 2020.

First Examination Report dated Dec. 30, 2025 for Indian Patent Application No. 202218052838, filed Apr. 1, 2020.

Examination Report dated Sep. 29, 2025 for MY Application No. PI2021005800, filed Apr. 1, 2020.

Technical Report issued Oct. 31, 2025 for PE Application No. 1658-2021, filed Apr. 1, 2020.

Examination Report dated Aug. 12, 2025 for SG Application No. 11202110718P, filed Apr. 1, 2020.

Office Action mailed Jul. 3, 2025 for UZ Application No. IAP 2021 0514, filed Apr. 1, 2020.

The plate map of compound treatment
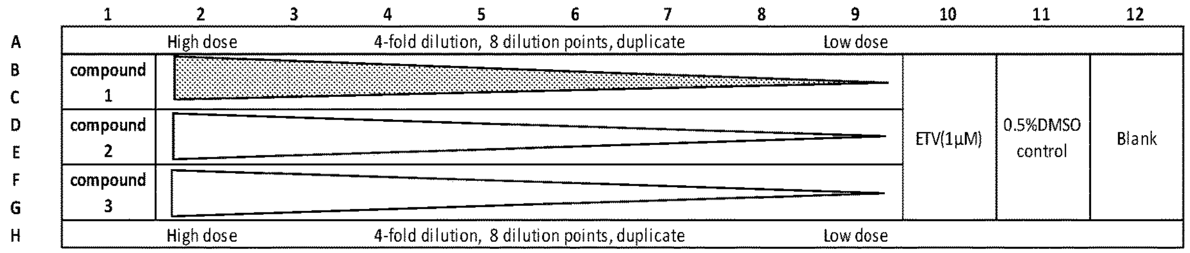

SEQUENCE LISTING

```
Sequence total quantity: 3
SEQ ID NO: 1           moltype = DNA  length = 20
FEATURE                Location/Qualifiers
misc_feature           1..20
                       note = HBV forward primer
source                 1..20
                       mol_type = other DNA
                       organism = synthetic construct
SEQUENCE: 1
gtgtctgcgg cgttttatca                                             20

SEQ ID NO: 2           moltype = DNA  length = 21
FEATURE                Location/Qualifiers
misc_feature           1..21
                       note = HBV reverse primer
```

-continued

```
source                  1..21
                        mol_type = other DNA
                        organism = synthetic construct
SEQUENCE: 2
gacaaacggg caacatacct t                                    21

SEQ ID NO: 3            moltype = DNA  length = 28
FEATURE                 Location/Qualifiers
misc_feature            1..28
                        note = HBV probe
source                  1..28
                        mol_type = other DNA
                        organism = synthetic construct
variation               6
                        note = n is c or t
SEQUENCE: 3
cctctncatc ctgctgctat gcctcatc                             28
```

PYRROLE COMPOUNDS

INCORPORATION BY REFERENCE TO ANY PRIORITY APPLICATIONS

Any and all applications for which a foreign or domestic priority claim is identified, for example, in the Application Data Sheet or Request as filed with the present application, are hereby incorporated by reference under 37 CFR 1.57, and Rules 4.18 and 20.6, including U.S. application Ser. No. 17/455,178, filed Nov. 16, 2021, Ser. No. 16/837,515, filed Apr. 1, 2020, 62/828,919, filed Apr. 3, 2019 and 62/932,686, filed Nov. 8, 2019. The present application is a continuation of U.S. application Ser. No. 17/455,178, filed Nov. 16, 2021, which is a continuation of U.S. application Ser. No. 16/837,515, filed Apr. 1, 2020, which is now U.S. Pat. No. 11,191,747, issued Dec. 7, 2021, which claims priority to U.S. Provisional Application Nos. 62/828,919, filed Apr. 3, 2019, and 62/932,686, filed Nov. 8, 2019, all of which are hereby incorporated by reference in its entireties.

BACKGROUND

Field

The present application relates to the fields of chemistry, biochemistry and medicine. Disclosed herein are compounds of Formula (I), or pharmaceutically acceptable salts thereof, pharmaceutical compositions that include a compound described herein (including pharmaceutically acceptable salts of a compound described herein) and methods of synthesizing the same. Also disclosed herein are methods of treating diseases and/or conditions with a compound of Formula (I), or a pharmaceutically acceptable salt thereof.

Description

The hepatitis B virus (HBV) is a DNA virus and a member of the Hepadnaviridae family. HBV infects more than 300 million worldwide, and is a causative agent of liver cancer and liver disease such as chronic hepatitis, cirrhosis, and hepatocellular carcinoma. Although there are approved drugs for treating HBV, by either boosting the immune system or slowing down the replication of the HBV virus, HBV continues to be a problem due to the drawbacks associated with each of the approved drugs.

SEQUENCE STATEMENT

This application contains a Sequence Listing, which has been submitted electronically and is hereby incorporated by reference in its entirety. The sequence listing, was created on Feb. 2, 2026, is named ALIG.024C2.xml and is 5.12 kb in size.

SUMMARY

Some embodiments disclosed herein relate to a compound of Formula (I), or a pharmaceutically acceptable salt thereof.

Some embodiments disclosed herein relate to a pharmaceutical composition that can contain an effective amount of a compound of Formula (I), or a pharmaceutically acceptable salt thereof.

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to a compound, or a pharmaceutically acceptable salt thereof, as described herein, or a pharmaceutical composition that includes an effective amount of a compound, or a pharmaceutically acceptable salt thereof, as described herein for the use of inhibiting the replication HBV and/or HDV.

These are other embodiments are described in greater detail below

BRIEF DESCRIPTION OF THE DRAWINGS

FIG. 1 shows the plate map of compound treatment for the HBV-DNA Antiviral Assay described herein.

DETAILED DESCRIPTION

HBV is a partially double-stranded circular DNA of about 3.2 kilobase (kb) pairs, and is classified into eight genotypes, A to H. The HBV replication pathway has been studied in great detail. T. J. Liang, Hepatology (2009) 49(5 Suppl): S13-S21. On part of replication includes the formation of the covalently closed circular (cccDNA) form. The presence of the cccDNA gives rise to the risk of viral reemergence throughout the life of the host organism. HBV carriers can transmit the disease for many years. An estimated 300 million people are living with hepatitis B virus infection, and it is estimated that over 750,000 people worldwide die of hepatitis B each year. In addition, immunosuppressed individuals or individuals undergoing chemotherapy are especially at risk for reactivation of a HBV infection. HBV can be acute and/or chronic. Acute HBV infection can be either asymptomatic or present with symptomatic acute hepatitis.

HBV can be transmitted by blood, semen, and/or another body fluid. This can occur through direct blood-to-blood contact, unprotected sex, sharing of needles, and from an infected mother to her baby during the delivery process. The HBV surface antigen (HBsAg) is most frequently used to screen for the presence of this infection. Currently available medications do not cure a HBV and/or HDV infection. Rather, the medications suppress replication of the virus.

The hepatitis D virus (HDV) is a DNA virus, also in the Hepadnaviridae family of viruses. HDV can propagate only in the presence of HBV. The routes of transmission of HDV are similar to those for HBV. Transmission of HDV can occur either via simultaneous infection with HBV (coinfection) or in addition to chronic hepatitis B or hepatitis B carrier state (superinfection). Both superinfection and coinfection with HDV results in more severe complications compared to infection with HBV alone. These complications include a greater likelihood of experiencing liver failure in acute infections and a rapid progression to liver cirrhosis, with an increased risk of developing liver cancer in chronic infections. In combination with hepatitis B, hepatitis D has the highest fatality rate of all the hepatitis infections, at 20%. There is currently no cure or vaccine for hepatitis D.

Definitions

Unless defined otherwise, all technical and scientific terms used herein have the same meaning as is commonly understood by one of ordinary skill in the art. All patents, applications, published applications and other publications referenced herein are incorporated by reference in their entirety unless stated otherwise. In the event that there are a plurality of definitions for a term herein, those in this section prevail unless stated otherwise.

Whenever a group is described as being "optionally substituted" that group may be unsubstituted or substituted with one or more of the indicated substituents. Likewise, when a group is described as being "unsubstituted or substituted" if substituted, the substituent(s) may be selected from one or more of the indicated substituents. If no substituents are indicated, it is meant that the indicated "optionally substituted" or "substituted" group may be substituted with one or more group(s) individually and independently selected from deuterium, alkyl, alkenyl, alkynyl, cycloalkyl, cycloalkenyl, aryl, heteroaryl, heterocyclyl, aryl (alkyl), heteroaryl(alkyl), (heterocyclyl)alkyl, hydroxy, alkoxy, acyl, cyano, halogen, thiocarbonyl, O-carbamyl, N-carbamyl, O-thiocarbamyl, N-thiocarbamyl, C-amido, N-amido, S-sulfonamido, N-sulfonamido, C-carboxy, O-carboxy, isocyanato, thiocyanato, nitro, azido, silyl, sulfenyl, sulfinyl, sulfonyl, haloalkyl, haloalkoxy, trihalomethanesulfonyl, trihalomethanesulfonamido, an amino, a mono-substituted amino group and a di-substituted amino group.

As used herein, "$C_a$ to $C_b$" in which "a" and "b" are integers refer to the number of carbon atoms in an alkyl, alkenyl or alkynyl group, or the number of carbon atoms in the ring of a cycloalkyl, cycloalkenyl, aryl, heteroaryl or heterocyclyl group. That is, the alkyl, alkenyl, alkynyl, ring of the cycloalkyl, ring of the cycloalkenyl, ring of the aryl, ring of the heteroaryl or ring of the heterocyclyl can contain from "a" to "b", inclusive, carbon atoms. Thus, for example, a "$C_1$ to $C_4$ alkyl" group refers to all alkyl groups having from 1 to 4 carbons, that is, $CH_3$—, $CH_3CH_2$—, $CH_3CH_2CH_2$—, $(CH_3)_2CH$—, $CH_3CH_2CH_2CH_2$—, $CH_3CH_2CH(CH_3)$— and $(CH_3)_3C$—. If no "a" and "b" are designated with regard to an alkyl, alkenyl, alkynyl, cycloalkyl cycloalkenyl, aryl, heteroaryl or heterocyclyl group, the broadest range described in these definitions is to be assumed.

As used herein, "alkyl" refers to a straight or branched hydrocarbon chain that comprises a fully saturated (no double or triple bonds) hydrocarbon group. The alkyl group may have 1 to 20 carbon atoms (whenever it appears herein, a numerical range such as "1 to 20" refers to each integer in the given range; e.g., "1 to 20 carbon atoms" means that the alkyl group may consist of 1 carbon atom, 2 carbon atoms, 3 carbon atoms, etc., up to and including 20 carbon atoms, although the present definition also covers the occurrence of the term "alkyl" where no numerical range is designated). The alkyl group may also be a medium size alkyl having 1 to 10 carbon atoms. The alkyl group could also be a lower alkyl having 1 to 6 carbon atoms. The alkyl group of the compounds may be designated as "$C_1$-$C_4$ alkyl" or similar designations. Byway of example only, "$C_1$-$C_4$ alkyl" indicates that there are one to four carbon atoms in the alkyl chain, i.e., the alkyl chain is selected from methyl, ethyl, propyl, iso-propyl, n-butyl, iso-butyl, sec-butyl and t-butyl. Typical alkyl groups include, but are in no way limited to, methyl, ethyl, propyl, isopropyl, butyl, isobutyl, tertiary butyl, pentyl and hexyl. The alkyl group may be substituted or unsubstituted.

As used herein, "alkenyl" refers to an alkyl group that contains in the straight or branched hydrocarbon chain one or more double bonds. The length of an alkenyl can vary. For example, the alkenyl can be a $C_{2-4}$ alkenyl, $C_{2-6}$ alkenyl or $C_{2-8}$ alkenyl. Examples of alkenyl groups include allenyl, vinylmethyl and ethenyl. An alkenyl group may be unsubstituted or substituted.

As used herein, "alkynyl" refers to an alkyl group that contains in the straight or branched hydrocarbon chain one or more triple bonds. The length of an alkynyl can vary. For example, the alkynyl can be a $C_{2-4}$ alkynyl, $C_{2-6}$ alkynyl or $C_{2-8}$ alkynyl. Examples of alkynyls include ethynyl and propynyl. An alkynyl group may be unsubstituted or substituted.

As used herein, "cycloalkyl" refers to a completely saturated (no double or triple bonds) mono- or multi-cyclic hydrocarbon ring system. When composed of two or more rings, the rings may be joined together in a fused fashion. Cycloalkyl groups can contain 3 to 10 atoms in the ring(s). 3 to 8 atoms in the ring(s) or 3 to 6 atoms in the ring(s). A cycloalkyl group may be unsubstituted or substituted. Typical cycloalkyl groups include, but are in no way limited to, cyclopropyl, cyclobutyl, cyclopentyl, cyclohexyl, cycloheptyl and cyclooctyl.

As used herein, "cycloalkenyl" refers to a mono- or multi-cyclic hydrocarbon ring system that contains one or more double bonds in at least one ring; although, if there is more than one, the double bonds cannot form a fully delocalized pi-electron system throughout all the rings (otherwise the group would be "aryl," as defined herein). When composed of two or more rings, the rings may be connected together in a fused fashion. A cycloalkenyl can contain 3 to 10 atoms in the ring(s) or 3 to 8 atoms in the ring(s). A cycloalkenyl group may be unsubstituted or substituted.

As used herein, "aryl" refers to a carbocyclic (all carbon) monocyclic or multicyclic aromatic ring system (including fused ring systems where two carbocyclic rings share a chemical bond) that has a fully delocalized pi-electron system throughout all the rings. The number of carbon atoms in an aryl group can vary. For example, the aryl group can be a $C_6$-$C_{14}$ aryl group, a $C_6$-$C_{10}$ aryl group, or a $C_6$ aryl group. Examples of aryl groups include, but are not limited to, benzene, naphthalene and azulene. An aryl group may be substituted or unsubstituted.

As used herein, "heteroaryl" refers to a monocyclic, bicyclic and tricyclic aromatic ring system (a ring system with fully delocalized pi-electron system) that contain(s) one or more heteroatoms (for example, 1 to 5 heteroatoms), that is, an element other than carbon, including but not limited to, nitrogen, oxygen and sulfur. The number of atoms in the ring(s) of a heteroaryl group can vary. For example, the heteroaryl group can contain 4 to 14 atoms in the ring(s), 5 to 10 atoms in the ring(s) or 5 to 6 atoms in the ring(s). Furthermore, the term "heteroaryl" includes fused ring systems where two rings, such as at least one aryl ring and at least one heteroaryl ring, or at least two heteroaryl rings, share at least one chemical bond. Examples of heteroaryl rings include, but are not limited to, furan, furazan, thiophene, benzothiophene, phthalazine, pyrrole, oxazole, benzoxazole, 1,2,3-oxadiazole, 1,2,4-oxadiazole, thiazole, 1,2,3-thiadiazole, 1,2,4-thiadiazole, benzothiazole, imidazole, benzimidazole, indole, indazole, pyrazole, benzopyrazole, isoxazole, benzoisoxazole, isothiazole, triazole, benzotriazole, thiadiazole, tetrazole, pyridine, pyridazine, pyrimidine, pyrazine, purine, pteridine, quinoline, isoquinoline, quinazoline, quinoxaline, cinnoline and triazine. A heteroaryl group may be substituted or unsubstituted.

As used herein, "heterocyclyl" refers to a monocyclic, bicyclic and tricyclic ring system wherein carbon atoms together with from 1 to 5 heteroatoms constitute said ring system. A heterocycle may optionally contain one or more unsaturated bonds situated in such a way, however, that a fully delocalized pi-electron system does not occur throughout all the rings. The number of atoms in the ring(s) of a heterocyclyl group can vary. For example, the heterocyclyl group can contain 4 to 14 atoms in the ring(s), 5 to 10 atoms in the ring(s) or 5 to 6 atoms in the ring(s). The heteroatom(s) is an element other than carbon including, but not limited to, oxygen, sulfur and nitrogen. A heterocycle may further contain one or more carbonyl or thiocarbonyl functionalities, so as to make the definition include oxo-systems and thio-systems such as lactams, lactones, cyclic imides, cyclic thioimides and cyclic carbamates. When composed of two or more rings, the rings may be joined together in a fused fashion. Additionally, any nitrogens in a heterocyclyl may be quaternized. Heterocyclyl groups may be unsubstituted or substituted. Examples of such "heterocyclyl groups include but are not limited to, 1,3-dioxin, 1,3-dioxane, 1,4-dioxane, 1,2-dioxolane, 1,3-dioxolane, 1,4-dioxolane, 1,3-oxathiane, 1,4-oxathiin, 1,3-oxathiolane, 1,3-dithiole, 1,3-dithiolane, 1,4-oxathiane, tetrahydro-1,4-thiazine, 2H-1,2-oxazine, maleimide, succinimide, barbituric acid, thiobarbituric acid, dioxopiperazine, hydantoin, dihydrouracil, trioxane, hexahydro-1,3,5-triazine, imidazoline, imidazolidine, isoxazoline, isoxazolidine, oxazoline, oxazolidine, oxazolidinone, thiazoline, thiazolidine, morpholine, oxirane, piperidine N-Oxide, piperidine, piperazine, pyrrolidine, pyrrolidone, pyrrolidione, 4-piperidone, pyrazoline, pyrazolidine, 2-oxopyrrolidine, tetrahydropyran, 4H-pyran, tetrahydrothiopyran, thiamorpholine, thiamorpholine sulfoxide, thiamorpholine sulfone and their benzo-fused analogs (e.g., benzimidazolidinone, tetrahydroquinoline and 3,4-methylenedioxyphenyl).

As used herein, "aryl(alkyl)" refer to an aryl group connected, as a substituent, via a lower alkylene group. The lower alkylene and aryl group of an aryl(alkyl) may be substituted or unsubstituted. Examples include but are not limited to benzyl, 2-phenyl(alkyl), 3-phenyl(alkyl), and naphthyl(alkyl).

As used herein, "heteroaryl(alkyl)" refer to a heteroaryl group connected, as a substituent, via a lower alkylene group. The lower alkylene and heteroaryl group of heteroaryl(alkyl) may be substituted or unsubstituted. Examples include but are not limited to 2-thienyl(alkyl), 3-thienyl(alkyl), furyl(alkyl), thienyl(alkyl), pyrrolyl(alkyl), pyridyl(alkyl), isoxazolyl(alkyl), imidazolyl(alkyl), and their benzo-fused analogs.

A "(heterocyclyl)alkyl" refer to a heterocyclic group connected, as a substituent, via a lower alkylene group. The lower alkylene and heterocyclyl of a heterocyclyl(alkyl) may be substituted or unsubstituted. Examples include but are not limited tetrahydro-2H-pyran-4-yl(methyl), piperidin-4-yl(ethyl), piperidin-4-yl(propyl), tetrahydro-2H-thiopyran-4-yl(methyl) and 1,3-thiazinan-4-yl(methyl).

"Lower alkylene groups" are straight-chained $—CH_2—$ tethering groups, forming bonds to connect molecular fragments via their terminal carbon atoms. Examples include but are not limited to methylene ($—CH_2—$), ethylene ($—CH_2CH_2—$), propylene ($—CH_2CH_2CH_2—$) and butylene ($—CH_2CH_2CH_2CH_2—$). A lower alkylene group can be substituted by replacing one or more hydrogen of the lower alkylene group with a substituent(s) listed under the definition of "substituted."

As used herein, "alkoxy" refers to the formula —OR wherein R is an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) is defined herein. A non-limiting list of alkoxys are methoxy, ethoxy, n-propoxy, 1-methylethoxy (isopropoxy), n-butoxy, iso-butoxy, sec-butoxy, tert-butoxy, phenoxy and benzoxy. An alkoxy may be substituted or unsubstituted.

As used herein, "acyl" refers to a hydrogen an alkyl, an alkenyl, an alkynyl, a cycloalkyl, a cycloalkenyl, aryl, heteroaryl, heterocyclyl, aryl(alkyl), heteroaryl(alkyl) or heterocyclyl(alkyl) connected, as substituents, via a carbonyl group. Examples include formyl, acetyl, propanoyl, benzoyl, and acryl. An acyl may be substituted or unsubstituted.

As used herein, "hydroxyalkyl" refers to an alkyl group in which one or more of the hydrogen atoms are replaced by a hydroxy group. Exemplary hydroxyalkyl groups include but are not limited to, hydroxymethyl, 1-hydroxyethyl, 2-hydroxyethyl, 3-hydroxypropyl, 2-hydroxypropyl and 2,2-dihydroxyethyl. A hydroxyalkyl may be substituted or unsubstituted.

As used herein, "haloalkyl" refers to an alkyl group in which one or more of the hydrogen atoms are replaced by a halogen (e.g., mono-haloalkyl, di-haloalkyl and tri-haloalkyl). Such groups include but are not limited to, chloromethyl, fluoromethyl, difluoromethyl, trifluoromethyl, 1-chloro-2-fluoromethyl and 2-fluoroisobutyl. A haloalkyl may be substituted or unsubstituted.

As used herein, "haloalkoxy" refers to a O-alkyl group in which one or more of the hydrogen atoms are replaced by a halogen (e.g., mono-haloalkoxy, di-haloalkoxy and tri-haloalkoxy). Such groups include but are not limited to, chloromethoxy, fluoromethoxy, difluoromethoxy, trifluoromethoxy, 1-chloro-2-fluoromethoxy and 2-fluoroisobutoxy. A haloalkoxy may be substituted or unsubstituted.

A "sulfenyl" group refers to an "—SR" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A sulfenyl may be substituted or unsubstituted.

A "sulfinyl" group refers to an "—S(═O)—R" group in which R can be the same as defined with respect to sulfenyl. A sulfinyl may be substituted or unsubstituted.

A "sulfonyl" group refers to an "$SO_2R$" group in which R can be the same as defined with respect to sulfenyl. A sulfonyl may be substituted or unsubstituted.

An "O-carboxy" group refers to a "RC(═O)O—" group in which R can be hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl), as defined herein. An O-carboxy may be substituted or unsubstituted.

The terms "ester" and "C-carboxy" refer to a "—C(═O)OR" group in which R can be the same as defined with respect to O-carboxy. An ester and C-carboxy may be substituted or unsubstituted.

A "thiocarbonyl" group refers to a "—C(═S)R" group in which R can be the same as defined with respect to O-carboxy. A thiocarbonyl may be substituted or unsubstituted.

A "trihalomethanesulfonyl" group refers to an "$X_3CSO_2—$" group wherein each X is a halogen.

A "trihalomethanesulfonamido" group refers to an "$X_3CS(O)_2N(R_A)$—" group wherein each X is a halogen, and $R_A$ is hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl).

The term "amino" as used herein refers to a —$NH_2$ group.

As used herein, the term "hydroxy" refers to a —OH group.

A "cyano" group refers to a "—CN" group.

The term "azido" as used herein refers to a —$N_3$ group.

An "isocyanato" group refers to a "—NCO" group.

A "thiocyanato" group refers to a "—CNS" group.

An "isothiocyanato" group refers to an "—NCS" group.

A "mercapto" group refers to an "—SH" group.

A "carbonyl" group refers to a C═O group.

An "S-sulfonamido" group refers to a "—$SO_2N(R_AR_B)$" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An S-sulfonamido may be substituted or unsubstituted.

An "N-sulfonamido" group refers to a "$RSO_2N(R_A)$—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-sulfonamido may be substituted or unsubstituted.

An "O-carbamyl" group refers to a "—OC(═O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-carbamyl may be substituted or unsubstituted.

An "N-carbamyl" group refers to an "ROC(═O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-carbamyl may be substituted or unsubstituted.

An "O-thiocarbamyl" group refers to a "—OC(═S)—N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An O-thiocarbamyl may be substituted or unsubstituted.

An "N-thiocarbamyl" group refers to an "ROC(═S)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-thiocarbamyl may be substituted or unsubstituted.

A "C-amido" group refers to a "—C(═O)N($R_AR_B$)" group in which $R_A$ and $R_B$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). A C-amido may be substituted or unsubstituted.

An "N-amido" group refers to a "RC(═O)N($R_A$)—" group in which R and $R_A$ can be independently hydrogen, alkyl, alkenyl, alkynyl, cycloalkyl, cycloalkenyl, aryl, heteroaryl, heterocyclyl, aryl(alkyl), heteroaryl(alkyl) or heterocyclyl(alkyl). An N-amido may be substituted or unsubstituted.

The term "halogen atom" or "halogen" as used herein, means any one of the radio-stable atoms of column 7 of the Periodic Table of the Elements, such as, fluorine, chlorine, bromine and iodine.

As used herein, the term "α-amino acids" refers to any amino acid (both standard and non-standard amino acids). Examples of suitable α-amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine.

As used herein, the term "phosphate" is used in its ordinary sense as understood by those skilled in the art, and includes

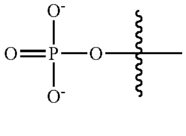 [SMILES: *OP(=O)([O-])[O-]]

along with its protonated forms (for example,

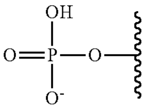
and
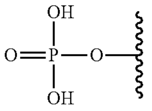
).

Where the numbers of substituents is not specified (e.g. haloalkyl), there may be one or more substituents present. For example "haloalkyl" may include one or more of the same or different halogens. As another example, "$C_1$-$C_3$ alkoxyphenyl" may include one or more of the same or different alkoxy groups containing one, two or three atoms.

As used herein, the abbreviations for any protective groups, amino acids and other compounds, are, unless indicated otherwise, in accord with their common usage, recognized abbreviations, or the IUPAC-IUB Commission on Biochemical Nomenclature (See, Biochem. 11:942-944 (1972)).

The term "pharmaceutically acceptable salt" refers to a salt of a compound that does not cause significant irritation to an organism to which it is administered and does not abrogate the biological activity and properties of the compound. In some embodiments, the salt is an acid addition salt of the compound. Pharmaceutical salts can be obtained by reacting a compound with inorganic acids such as hydrohalic acid (e.g., hydrochloric acid or hydrobromic acid), sulfuric acid, nitric acid and phosphoric acid. Pharmaceutical salts can also be obtained by reacting a compound with an organic acid such as aliphatic or aromatic carboxylic or sulfonic acids, for example formic, acetic, succinic, lactic, malic, tartaric, citric, ascorbic, nicotinic, methanesulfonic, ethanesulfonic, p-toluenesulfonic, salicylic or naphthalenesulfonic acid. Pharmaceutical salts can also be obtained by reacting a compound with a base to form a salt such as an ammonium salt, an alkali metal salt, such as a sodium or a potassium salt, an alkaline earth metal salt, such as a calcium or a magnesium salt, a salt of organic bases such as dicyclohexylamine, N-methyl-D-glucamine, tris(hydroxymethyl)methylamine, $C_1$-$C_7$ alkylamine, cyclohexylamine, triethanolamine, ethylenediamine, and salts with amino acids such as arginine and lysine.

Terms and phrases used in this application, and variations thereof, especially in the appended claims, unless otherwise expressly stated, should be construed as open ended as opposed to limiting. As examples of the foregoing, the term 'including' should be read to mean 'including, without limitation,' 'including but not limited to,' or the like; the term 'comprising' as used herein is synonymous with 'including,' 'containing,' or 'characterized by,' and is inclusive or open-ended and does not exclude additional, unrecited elements or method steps; the term 'having' should be interpreted as 'having at least;' the term 'includes' should be interpreted as 'includes but is not limited to;' the term 'example' is used to provide exemplary instances of the item in discussion, not an exhaustive or limiting list thereof. In addition, the term "comprising" is to be interpreted synonymously with the phrases "having at least" or "including at least". When used in the context of a compound or composition, the term "comprising" means that the compound or composition includes at least the recited features or components, but may also include additional features or components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. The indefinite article "a" or "an" does not exclude a plurality.

It is understood that, in any compound described herein having one or more chiral centers, if an absolute stereochemistry is not expressly indicated, then each center may independently be of (R)-configuration or (S)-configuration or a mixture thereof. Thus, the compounds provided herein may be enantiomerically pure, enantiomerically enriched, racemic mixture, diastereomerically pure, diastereomerically enriched, or a stereoisomeric mixture. In addition it is understood that, in any compound described herein having one or more double bond(s) generating geometrical isomers that can be defined as E or Z, each double bond may independently be E or Z a mixture thereof. Likewise, it is understood that, in any compound described, all tautomeric forms are also intended to be included.

It is to be understood that where compounds disclosed herein have unfilled valencies, then the valencies are to be filled with hydrogens or isotopes thereof, e.g., hydrogen-1 (protium) and hydrogen-2 (deuterium).

It is understood that the compounds described herein can be labeled isotopically. Substitution with isotopes such as deuterium may afford certain therapeutic advantages resulting from greater metabolic stability, such as, for example, increased in vivo half-life or reduced dosage requirements. Each chemical element as represented in a compound structure may include any isotope of said element. For example, in a compound structure a hydrogen atom may be explicitly disclosed or understood to be present in the compound. At any position of the compound that a hydrogen atom may be present, the hydrogen atom can be any isotope of hydrogen, including but not limited to hydrogen-1 (protium) and hydrogen-2 (deuterium). Thus, reference herein to a compound encompasses all potential isotopic forms unless the context clearly dictates otherwise.

Where a range of values is provided, it is understood that the upper and lower limit, and each intervening value between the upper and lower limit of the range is encompassed within the embodiments.

Compounds

Some embodiments disclosed herein relate to a compound of Formula (I), or a pharmaceutically acceptable salt thereof:

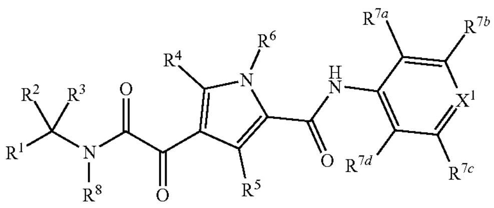

(I)

wherein: $R^1$ can be an unsubstituted or a substituted $C_2$ alkenyl, an unsubstituted or a substituted $C_2$ alkynyl, an unsubstituted $C_{1-4}$ haloalkyl, an unsubstituted or a substituted monocyclic heteroaryl, an unsubstituted or a substituted bicyclic heteroaryl or an unsubstituted or a substituted monocyclic heterocyclyl, wherein when the $C_2$ alkenyl, the $C_2$ alkynyl and the monocyclic heteroaryl are substituted, the $C_2$ alkenyl, the $C_2$ alkynyl and the monocyclic heteroaryl can be independently substituted with one or more substituents selected from halogen, an unsubstituted $C_{1-4}$ alkyl, an unsubstituted $C_{1-4}$ haloalkyl, an unsubstituted $C_{1-4}$ hydroxyalkyl, an unsubstituted monocyclic $C_{3-6}$ cycloalkyl and a hydroxy-substituted monocyclic $C_{3-6}$ cycloalkyl; $R^2$ and $R^3$ can be independently selected from hydrogen, an unsubstituted or a substituted $C_{1-4}$ alkyl, an unsubstituted $C_{1-4}$ haloalkyl, an unsubstituted or a substituted monocyclic $C_{3-6}$ cycloalkyl, an unsubstituted or a substituted monocyclic 3-6 membered heterocyclyl, an unsubstituted $C_{1-4}$ hydroxyalkyl and an unsubstituted $C_{1-5}$ alkoxyalkyl, wherein when the monocyclic $C_{3-6}$ cycloalkyl and the monocyclic 3-6 heterocyclyl are substituted, the monocyclic $C_{3-6}$ cycloalkyl and the monocyclic 3-6 heterocyclyl can be independently substituted with one or more substituents selected from halogen or hydroxy, and wherein when the $C_{1-4}$ alkyl is substituted, the $C_{1-4}$ alkyl is substituted with one or more substituents selected from the group consisting of a phosphate, an O-linked α-amino acid and an O-carboxy; or $R^2$ and $R^3$ can be taken together along with the carbon to which $R^2$ and $R^3$ are attached to form an unsubstituted or a substituted monocyclic $C_{3-6}$ cycloalkyl or an unsubstituted or a substituted monocyclic 3-6 membered heterocyclyl, wherein when the $C_{3-6}$ cycloalkyl and 3-6 membered heterocyclyl are substituted, the $C_{3-6}$ cycloalkyl and the 3-6 membered heterocyclyl can be independently substituted with 1 or 2 substituents selected from halogen and hydroxy; $R^4$ and $R^5$ can be independently hydrogen, halogen, an unsubstituted $C_{1-4}$ alkyl, a deuterated $C_{1-4}$ alkyl or an unsubstituted $C_{2-4}$ alkenyl; $R^6$ can be hydrogen, an unsubstituted $C_{1-4}$ alkyl, a deuterated $C_{1-4}$ alkyl or an unsubstituted $C_{3-4}$ alkenyl; and provided that at least one of $R^4$, $R^5$ and $R^6$ is not hydrogen; or $R^5$ can be hydrogen, halogen, an unsubstituted $C_{1-4}$ alkyl or an unsubstituted $C_{2-4}$ alkenyl; and $R^4$ and $R^6$ can be taken together to form an unsubstituted or substituted 5-6 membered heterocyclic ring; $X^1$ can be $CR^A$ or N (nitrogen); $R^{7a}$, $R^{7b}$, $R^{7c}$ and $R^{7d}$ can be independently hydrogen, halogen, an unsubstituted $C_{1-4}$ haloalkyl, cyano or an unsubstituted $C_{1-4}$ alkoxy; $R^8$ can be hydrogen, $—CH_2OC(═O)$-(an unsubstituted $C_{1-4}$ alkyl), —$CH_2OC$(=O)—O(an unsubstituted $C_{1-4}$ alkyl), —$CH_2$-(α-amino acid) or —$CH_2$-phosphate; and $R^A$ can be hydrogen, halogen, an unsubstituted $C_{1-4}$ haloalkyl or cyano.

Various groups can be attached to the pyrrole ring of Formula (I). As provided herein, the pyrrole ring can have hydrogen, halogen, an unsubstituted $C_{1-4}$ alkyl, a deuterated $C_{1-4}$ alkyl and/or or an unsubstituted $C_{2-4}$ alkenyl attached, provided that at least one of $R^4$, $R^5$ and $R^6$ is not hydrogen. Examples of $C_{1-4}$ alkyls include methyl, ethyl, n-propyl, isopropyl, n-butyl, isobutyl and tert-butyl. In some embodiments, one of $R^4$ and $R^5$ can be halogen or an unsubstituted $C_{1-4}$ alkyl and/or $R^6$ can be an unsubstituted $C_{1-4}$ alkyl. In other embodiments, $R^4$ and/or $R^5$ can be each independently halogen or an unsubstituted $C_{1-4}$ alkyl and/or $R^6$ can be an unsubstituted $C_{1-4}$ alkyl. In still other embodiments, $R^4$ and $R^5$ can be each independently halogen or an unsubstituted $C_{1-4}$ alkyl and $R^6$ can be an unsubstituted $C_{1-4}$ alkyl. In yet still other embodiments, one of $R^4$, $R^5$ and $R^6$ can be an unsubstituted $C_{1-4}$ alkyl and one of $R^4$, $R^5$ and $R^6$ can be an unsubstituted $C_{3-4}$ alkenyl. When one of $R^4$, $R^5$ and $R^6$ is a deuterated $C_{1-4}$ alkyl, one or more hydrogens of a $C_{1-4}$ alkyl can be replaced by deuteriums. For example, one of $R^4$, $R^5$ and $R^6$ can be $CH_2D$, $CHD_2$, $CD_3$, $CH_2CD_3$, $CD_2CD_3$, $CH_2CH_2CD_3$, $CH(CD_3)_2$. In some embodiments, one of $R^4$, $R^5$ and $R^6$ can be a deuterated $C_{1-4}$ alkyl, and the other two of $R^4$, $R^5$ and $R^6$ can be an unsubstituted $C_{1-4}$ alkyl.

In some embodiments, $R^4$ can be hydrogen; $R^5$ can be hydrogen; and $R^6$ can be an unsubstituted $C_{1-4}$ alkyl. In other embodiments, $R^4$ can be halogen; $R^5$ can be hydrogen; and $R^6$ can be an unsubstituted $C_{1-4}$ alkyl. In still other embodiments, $R^4$ can be hydrogen; $R^5$ can be halogen; and $R^6$ can be an unsubstituted $C_{1-4}$ alkyl. In still other embodiments, $R^4$ can be hydrogen; $R^5$ can be an unsubstituted $C_{1-4}$ alkyl; and $R^6$ can be an unsubstituted $C_{3-4}$ alkenyl.

In some embodiments, $R^4$ can be hydrogen; $R^5$ can be halogen; and $R^6$ can be hydrogen. In other embodiments, $R^4$ can be hydrogen; $R^5$ can be halogen; and $R^6$ can be hydrogen. In still other embodiments, $R^4$ can be halogen; $R^5$ can be halogen; and $R^6$ can be hydrogen. In yet still other embodiments, $R^4$ can be an unsubstituted $C_{1-4}$ alkyl; $R^5$ can be hydrogen; and $R^6$ can be an unsubstituted $C_{1-4}$ alkyl. In some embodiments, $R^4$ can be an unsubstituted $C_{1-4}$ alkyl; $R^5$ can be halogen; and $R^6$ can be an unsubstituted $C_{1-4}$ alkyl. In other embodiments, $R^4$ can be an unsubstituted $C_{1-4}$ alkyl; $R^5$ can be an unsubstituted $C_{1-4}$ alkyl; and $R^6$ can be an unsubstituted $C_{1-4}$ alkyl. In still other embodiments, when $R^4$, $R^5$ and/or $R^6$ are an unsubstituted $C_{1-4}$ alkyl, the unsubstituted $C_{1-4}$ alkyl can be methyl. For example, $R^4$, $R^5$ and $R^6$ can be each methyl. In yet still other embodiments, $R^4$ can be hydrogen; and $R^5$ and $R^6$ can be each an unsubstituted $C_{1-4}$ alkyl. In some embodiments, $R^4$ can be halogen; and $R^5$ and $R^6$ can be each an unsubstituted $C_{1-4}$ alkyl. In other embodiments, $R^5$ can be halogen; and $R^4$ and $R^6$ can be each an unsubstituted $C_{1-4}$ alkyl. In still other embodiments, $R^4$ and $R^5$ can be each hydrogen; and $R^6$ can be an unsubstituted $C_{1-4}$ alkyl. In yet still embodiments, $R^4$ can be hydrogen; $R^5$ can be halogen; and $R^6$ can be an unsubstituted $C_{1-4}$ alkyl. In some embodiments, $R^4$ and $R^5$ can be each halogen; and $R^6$ can be an unsubstituted $C_{1-4}$ alkyl. In other embodiments, $R^4$ and $R^5$ can be each an unsubstituted $C_{1-4}$ alkyl; and $R^6$ can be a deuterated $C_{1-4}$ alkyl, such as $CD_3$.

As provided herein, in some embodiments, $R^5$ can be hydrogen, halogen, an unsubstituted $C_{1-4}$ alkyl or an unsubstituted $C_{2-4}$ alkenyl; and $R^4$ and $R^6$ can be taken together to form an unsubstituted or substituted 5-6 membered heterocyclic ring. For example, $R^4$ and $R^6$ can be taken together to form an unsubstituted or substituted

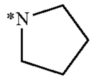

or an unsubstituted or substituted

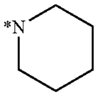, wherein N* indicates the nitrogen of the pyrrolyl of Formula (I). In some embodiments, $R^5$ can be hydrogen; and $R^4$ and $R^6$ can be taken together to form an unsubstituted or substituted 5-6 membered heterocyclic ring such as those described herein. In other embodiments, $R^5$ can be halogen; and $R^4$ and $R^6$ can be taken together to form an unsubstituted or substituted 5-6 membered heterocyclic ring such as those described herein. In still other embodiments, $R^5$ can be an unsubstituted $C_{1-4}$ alkyl; and $R^4$ and $R^6$ can be taken together to form an unsubstituted or substituted 5-6 membered heterocyclic ring such as those described herein. In yet still other embodiments, $R^5$ can be an unsubstituted $C_{2-4}$ alkenyl; and $R^4$ and $R^6$ can be taken together to form an unsubstituted or substituted 5-6 membered heterocyclic ring such as those described herein.

The 6-membered aromatic ring that includes $X^1$ can be an optionally substituted phenyl or an optionally substituted pyridine. When $X^1$ is $CR^A$, the 6-membered ring can be an optionally substituted phenyl. The 6-membered aromatic ring can be an optionally substituted pyridine when $X^1$ is N (nitrogen). As provided herein, the 6-membered aromatic ring that includes $X^1$ can be substituted. When substituted, the phenyl and/or pyridine can be substituted 1, 2 or 3 or more times. The substituted phenyl ring can be substituted at the para-position. Additionally or in the alternative, the phenyl ring can be substituted at the meta-position. In some embodiments, the phenyl ring can be substituted at the ortho-position.

In some embodiments, $X^1$ can be CH. In other embodiments, $X^1$ can be $CR^A$. When $X^1$ is $CR^A$, $R^A$ can be a non-hydrogen group. For example, in some embodiments, $R^A$ can be halogen (such as F, Cl or Br). In other embodiments, $R^A$ can be an unsubstituted $C_{1-4}$ haloalkyl. Suitable $C_{1-4}$ haloalkyls include, but are not limited to, —$CHF_2$, —$CF_3$, $CH_2F$, CHClF AND $CCl_3$. In still other embodiments, $R^A$ can be cyano. In yet still other embodiments, $R^A$ can be an unsubstituted $C_{1-4}$ alkoxy. Example $C_{1-4}$ alkoxys include methoxy, ethoxy, n-propoxy, isopropoxy, n-butoxy, isobutoxy and tert-butoxy.

As described herein, $R^{7b}$ and/$R^{7c}$ can be hydrogen. As with $R^A$, $R^{7b}$ and/$R^{7c}$ can be a non-hydrogen group, such as halogen, an unsubstituted $C_{1-4}$ haloalkyl, cyano and an unsubstituted $C_{1-4}$ alkoxy. In some embodiments, $R^{7b}$ can be hydrogen. In other embodiments, $R^{7b}$ can be halogen (for example, F, Cl or Br). In still other embodiments, $R^{7b}$ can be an unsubstituted $C_{1-4}$ haloalkyl, such as those described herein and including —$CHF_2$, —$CF_3$, and —$CH_2F$. In yet still other embodiments, $R^{7b}$ can be cyano. In some embodiments, $R^{7b}$ can be an unsubstituted $C_{1-4}$ alkoxy, such as those described herein. In some embodiments, $R^{7c}$ can be hydrogen. In other embodiments, $R^{7c}$ can be halogen, such as F, Cl or Br. In still other embodiments, $R^{7c}$ can be an unsubstituted $C_{1-4}$ haloalkyl, such as —$CHF_2$, —$CF_3$, —$CH_2F$, —CHClF and —$CCl_3$. In yet still other embodiments, $R^{7c}$ can be cyano. In some embodiments, $R^{7c}$ can be an unsubstituted $C_{1-4}$ alkoxy, for example, methoxy, ethoxy, n-propoxy, isopropoxy, n-butoxy, isobutoxy and tert-butoxy.

As with other positions on the 6-membered aromatic ring that includes $X^1$, $R^{7a}$ and/or $R^{7d}$ can be hydrogen or a non-hydrogen group. In some embodiments, $R^{7a}$ can be hydrogen. In other embodiments, $R^{7a}$ can be halogen, such as F, Cl or Br. In still other embodiments, $R^{7a}$ can be an unsubstituted $C_{1-4}$ haloalkyl, for example, —$CHF_2$, —$CF_3$, —$CH_2F$, —CHClF and —$CCl_3$. In yet still other embodiments, $R^{7a}$ can be cyano. In some embodiments, $R^{7a}$ can be an unsubstituted $C_{1-4}$ alkoxy, including, but not limited to, those described herein. In some embodiments, $R^{7d}$ can be hydrogen. In other embodiments, $R^{7d}$ can be halogen (for example, F, Cl or Br). In still other embodiments, $R^{7d}$ can be an unsubstituted $C_{1-4}$ haloalkyl, including, but are not limited to, —$CHF_2$, —$CF_3$, —$CH_2F$, —CHClF and —$CCl_3$. In yet still other embodiments, $R^{7d}$ can be cyano. In some embodiments, $R^{7d}$ can be an unsubstituted $C_{1-4}$ alkoxy. For example, $R^{7d}$ can be for example, methoxy, ethoxy, n-propoxy, isopropoxy, n-butoxy, isobutoxy or tert-butoxy.

In some embodiments, $R^A$ can be a non-hydrogen group as described herein; and $R^{7b}$ or $R^{7c}$ can be a non-hydrogen group as described herein. In other embodiments, $R^A$ can be a non-hydrogen group as described herein; $R^{7b}$ or $R^{7c}$ can be a non-hydrogen group as described herein; and $R^{7a}$ and $R^{7d}$ are each hydrogen. In still other embodiments, $R^A$ can be a non-hydrogen group as described herein; one of $R^{7b}$ and $R^{7c}$ can be a non-hydrogen group as described herein, and the other of $R^{7b}$ and $R^{7c}$ can be hydrogen; and $R^{7a}$ and $R^{7d}$ are each hydrogen. The following are examples of 6-membered aromatic ring that includes $X^1$:

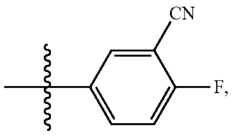

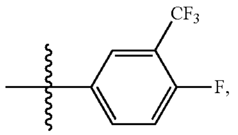

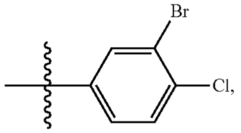

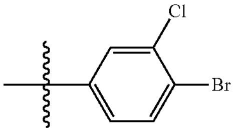

and

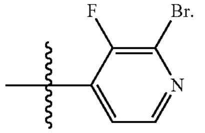

In some embodiments, $R^2$ and $R^3$ can be independently selected from hydrogen, an unsubstituted or a substituted $C_{1-4}$ alkyl, an unsubstituted $C_{1-4}$ haloalkyl, an unsubstituted or a substituted monocyclic $C_{3-6}$ cycloalkyl, an unsubstituted or a substituted monocyclic 3-6 membered heterocyclyl, an unsubstituted $C_{1-4}$ hydroxyalkyl and an unsubstituted $C_{1-5}$ alkoxyalkyl, wherein when the monocyclic $C_{3-6}$ cycloalkyl and the monocyclic 3-6 heterocyclyl are substituted, the monocyclic $C_{3-6}$ cycloalkyl and the monocyclic 3-6 heterocyclyl can be independently substituted with one or more substituents selected from halogen or hydroxy, and wherein when the $C_{1-4}$ alkyl is substituted, the $C_{1-4}$ alkyl is substituted with one or more substituents selected from the group consisting of a phosphate, an O-linked α-amino acid and an O-carboxy. In other embodiments, $R^2$ and $R^3$ are taken together along with the carbon to which $R^2$ and $R^3$ are attached to form an unsubstituted or a substituted monocyclic $C_{3-6}$ cycloalkyl or an unsubstituted or a substituted monocyclic 3-6 membered heterocyclyl, wherein when the $C_{3-6}$ cycloalkyl and 3-6 membered heterocyclyl are substituted, the $C_{3-6}$ cycloalkyl and the 3-6 membered heterocyclyl are independently substituted with 1 or 2 substituents selected from the group consisting of halogen and hydroxy.

The substituents for $R^2$ and $R^3$ can be the same or different, or $R^2$ and $R^3$ can be taken together along with the carbon to which $R^2$ and $R^3$ are attached to form an unsubstituted or a substituted monocyclic $C_{3-6}$ cycloalkyl or an unsubstituted or a substituted monocyclic 3-6 membered heterocyclyl. In some embodiments, $R^2$ and $R^3$ can be each hydrogen. In other embodiments, $R^2$ and $R^3$ can be each an unsubstituted $C_{1-4}$ alkyl. Examples of suitable an unsubstituted $C_{1-4}$ alkyls are described herein. For example, $R^2$ and $R^3$ can be each methyl.

As described herein, $R^2$ and $R^3$ can be different. As an example, one of $R^2$ and $R^3$ can be hydrogen; and the other of $R^2$ and $R^3$ can be an unsubstituted $C_{1-4}$ alkyl, an unsubstituted $C_{1-4}$ haloalkyl, an unsubstituted or a substituted monocyclic $C_{3-6}$ cycloalkyl, an unsubstituted or a substituted monocyclic 3-6 membered heterocyclyl, an unsubstituted $C_{1-4}$ hydroxyalkyl and an unsubstituted $C_{1-5}$ alkoxyalkyl. In some embodiments, one of $R^2$ and $R^3$ can be hydrogen; and the other of $R^2$ and $R^3$ can be an unsubstituted $C_{1-4}$ alkyl, such as methyl, ethyl, n-propyl, isopropyl, n-butyl, isobutyl and tert-butyl. In other embodiments, one of $R^2$ and $R^3$ can be hydrogen; and the other of $R^2$ and $R^3$ can be an unsubstituted $C_{1-4}$ haloalkyl. Exemplary $C_{1-4}$ haloalkyls are described herein, and include, but are not limited to, —$CHF_2$, —$CF_3$, —$CH_2F$, —CHClF and —$CCl_3$. In still other embodiments, one of $R^2$ and $R^3$ can be hydrogen; and the other of $R^2$ and $R^3$ can be an unsubstituted or a substituted monocyclic $C_{3-6}$ cycloalkyl. For example, one of $R^2$ and $R^3$ can be hydrogen; and the other of $R^2$ and $R^3$ can be an unsubstituted cycloproyl, an unsubstituted cyclobutyl, an unsubstituted cyclopentyl and an unsubstituted cyclohexyl; or one of $R^2$ and $R^3$ can be hydrogen; and the other of $R^2$ and $R^3$ can be a substituted cycloproyl, a substituted cyclobutyl, a substituted cyclopentyl and a substituted cyclohexyl. When substituted, the substituted monocyclic $C_{3-6}$ cycloalkyl can be substituted 1, 2 or 3 or times with a substituent independently selected from halogen (F, Cl or Br) and hydroxy. In some embodiments, substituted monocyclic $C_{3-6}$ cycloalkyl can be substituted with 1 or 2 halogens. For example, one of $R^2$ and $R^3$ can be hydrogen; and the other of $R^2$ and $R^3$ can be

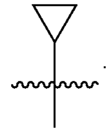

In yet still other embodiments, one of $R^2$ and $R^3$ can be hydrogen; and the other of $R^2$ and $R^3$ can be an unsubstituted or a substituted monocyclic 3-6 membered heterocyclyl. Various monocyclic 3-6 membered heterocyclyls are suitable for $R^2$/$R^3$. In some embodiments, one of $R^2$ and $R^3$ can be hydrogen; and the other of $R^2$ and $R^3$ can be an unsubstituted $C_{1-4}$ hydroxyalkyl. As an example, one of $R^2$ and $R^3$ can be hydrogen; and the other of $R^2$ and $R^3$ can be $—CH_2OH$. In other embodiments, one of $R^2$ and $R^3$ can be hydrogen; and the other of $R^2$ and $R^3$ can be an unsubstituted $C_{1-5}$ alkoxyalkyl. Examples of an unsubstituted $C_{1-5}$ alkoxyalkyls include $—CH_2OCH_3$, $—CH_2CH_2OCH_3$, $—CH_2OCH_2CH_3$, $—CH_2CH_2OCH_2CH_3$, $—CH_2OCH(CH_3)_2$, $—CH_2OCH_2CH(CH_3)_2$ and $—CH_2CH_2OCH(CH_3)_2$.

A prodrug moiety can be present at one of $R^2$ and $R^3$. In some embodiments, one of $R^2$ and $R^3$ can be an unsubstituted $C_{1-4}$ alkyl (for example, methyl); and the other of $R^2$ and $R^3$ can be a substituted $C_{1-4}$ alkyl, wherein the $C_{1-4}$ alkyl is substituted with one or more substituents selected from a phosphate, an O-linked α-amino acid and an O-carboxy. Suitable α-amino acids are described herein and include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. As used herein, an "—O-linked α-amino acid" refers to an α-amino acid that is attached to the indicated moiety via the hydroxy from its main-chain carboxylic acid group. When the α-amino acid is attached in an —O-linked α-amino acid, the hydrogen that is part of the hydroxy from its main-chain carboxylic acid group is not present and the α-amino acid is attached via the oxygen. In some embodiments, the —O-linked α-amino acid substituted on the $C_{1-4}$ alkyl of $R^2$ or $R^3$ can be an —O-linked-L-α-amino acid. In other embodiments, the —O-linked α-amino acid substituted on the $C_{1-4}$ alkyl of $R^2$ or $R^3$ can be an —O-linked-D-α-amino acid. Examples of —O-linked-α-amino acids are shown here with respect to $R^8$. As another example of a prodrug moiety that can be present on the substituted $C_{1-4}$ alkyl of $R^2$ or $R^3$ is an O-carboxy. In some embodiments, one of $R^2$ and $R^3$ can be an unsubstituted $C_{1-4}$ alkyl (such as, methyl); and the other of $R^2$ and $R^3$ can be an O-carboxy substituted $C_{1-4}$ alkyl. For example, the O-carboxy substituted $C_{1-4}$ alkyl can have the structure $—(CH_2)_4—OC(=O)$(an unsubstituted $C_{1-4}$ alkyl). As described herein, the $C_{1-4}$ alkyl of $R^2$ or $R^3$ can be substituted with a phosphate. For example, when $R^2$ or $R^3$ are a substituted $C_{1-4}$ alkyl with a phosphate, $R^2$ or $R^3$ can be $—CH_2—O—P(=O)(O^-)_2$ or $—CH_2—O—P(=O)(OH)_2$.

As provided herein, $R^2$ and $R^3$ can be taken together along with the carbon to which $R^2$ and $R^3$ are attached to form an unsubstituted or a substituted monocyclic $C_{3-6}$ cycloalkyl or an unsubstituted or a substituted monocyclic 3-6 membered heterocyclyl are substituted, the $C_{3-6}$ cycloalkyl and the 3-6 membered heterocyclyl are independently substituted with 1 or 2 substituents selected from the group consisting of halogen and hydroxy. In some embodiments, $R^2$ and $R^3$ can be taken together along with the carbon to which $R^2$ and $R^3$ are attached to form an unsubstituted monocyclic $C_{3-6}$ cycloalkyl. In other embodiments, $R^2$ and $R^3$ can be taken together along with the carbon to which $R^2$ and $R^3$ are attached to form a substituted monocyclic $C_{3-6}$ cycloalkyl. The $C_{3-6}$ cycloalkyl can be an unsubstituted or a substituted cyclopropyl, an unsubstituted or a substituted cyclobutyl, an unsubstituted or a substituted cyclopentyl or an unsubstituted or a substituted cyclohexyl. When the $C_{3-6}$ cycloalkyl is substituted, the $C_{3-6}$ cycloalkyl can be substituted 1, 2 or 3 or more times. When 2 or more substituents are present, the substituents can be all the same or at least different substituents can be present. For example, in some embodiments, the $C_{3-6}$ cycloalkyl can be substituted with 1 or 2 halogens (such as 1 or 2 fluoro substituents). In other embodiments, the $C_{3-6}$ cycloalkyl can be substituted with a hydroxy. Exemplary $C_{3-6}$ cycloalkyls include unsubstituted cyclopropyl, unsubstituted cyclobutyl, unsubstituted cyclopentyl, unsubstituted cyclohexyl, fluoro-substituted cyclopropyl, fluoro-substituted cyclobutyl, fluoro-substituted cyclopentyl, fluoro-substituted cyclohexyl, hydroxy-substituted cyclopropyl, hydroxy-substituted cyclobutyl, hydroxy-substituted cyclopentyl, hydroxy-substituted cyclohexyl,

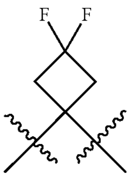

and

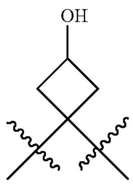

.

In some embodiments, $R^2$ and $R^3$ can be taken together along with the carbon to which $R^2$ and $R^3$ are attached to form an unsubstituted monocyclic 3-6 membered heterocyclyl. In some embodiments, $R^2$ and $R^3$ can be taken together along with the carbon to which $R^2$ and $R^3$ are attached to form a substituted monocyclic 3-6 membered heterocyclyl. For example, $R^2$ and $R^3$ can be taken together along with the carbon to which $R^2$ and $R^3$ are attached to form an unsubstituted or substituted monocyclic 3-membered heterocyclyl, an unsubstituted or substituted monocyclic 4-membered heterocyclyl, an unsubstituted or substituted monocyclic 5-membered heterocyclyl or an unsubstituted or substituted monocyclic 6-membered heterocyclyl. In some embodiments, $R^2$ and $R^3$ can be taken together along with the carbon to which $R^2$ and $R^3$ are attached to form an unsubstituted monocyclic, oxygen-containing 3-6 membered heterocyclyl. In other embodiments, $R^2$ and $R^3$ can be taken together along with the carbon to which $R^2$ and $R^3$ are attached to form an unsubstituted monocyclic, nitrogen-containing 3-6 membered heterocyclyl. Suitable monocyclic 3-6 membered heterocyclyls include, but are not limited to, an unsubstituted or substituted oxetane, an unsubstituted or substituted thietane, an unsubstituted or substituted

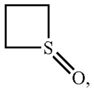

an unsubstituted or substituted

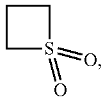

an unsubstituted or substituted

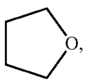

an unsubstituted or substituted

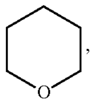, an unsubstituted or substituted

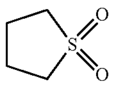

and an unsubstituted or substituted

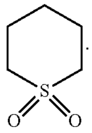.

In some embodiments, $R^2$ and $R^3$ can be taken together along with the carbon to which $R^2$ and $R^3$ are attached to form

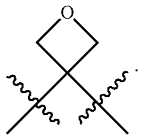 [SMILES: *C1(*)COC1].

Various unsaturated substituents can be present at $R^1$. As described herein, $R^1$ can be substituted or unsubstituted. In some embodiments, $R^1$ can be an unsubstituted $C_2$ alkenyl. In other embodiments, $R^1$ can be a substituted $C_2$ alkenyl that can be substituted with one or more substituents independently selected from halogen, an unsubstituted $C_{1-4}$ haloalkyl an unsubstituted $C_{1-4}$ hydroxyalkyl, an unsubstituted monocyclic $C_{3-6}$ cycloalkyl and a hydroxy-substituted monocyclic $C_{3-6}$ cycloalkyl. In some embodiments, $R^1$ can be an unsubstituted $C_2$ alkynyl. In other embodiments, $R^1$ can be a substituted $C_2$ alkynyl. The $C_2$ alkynyl can be substituted one or more times with a substituent independently selected from halogen, an unsubstituted $C_{1-4}$ haloalkyl an unsubstituted $C_{1-4}$ hydroxyalkyl, an unsubstituted monocyclic $C_{3-6}$ cycloalkyl and a hydroxy-substituted monocyclic $C_{3-6}$ cycloalkyl. For example, the $C_2$ alkynyl can be substituted one time with an unsubstituted monocyclic $C_{3-6}$ cycloalkyl or the $C_2$ alkynyl can be substituted one time with an unsubstituted $C_{1-4}$ haloalkyl. In some embodiments, $R^1$ can be an unsubstituted $C_{1-4}$ haloalkyl, for example, $CF_3$.

As described herein, several cyclic moieties can be present at $R^1$. In some embodiments, $R^1$ can be an unsubstituted monocyclic heteroaryl. In other embodiments, $R^1$ can be a substituted monocyclic heteroaryl. Several suitable monocyclic heteroaryls are described herein. In some embodiments, $R^1$ can be an unsubstituted or a substituted nitrogen-containing monocyclic heteroaryl, for example, $R^1$ can be an unsubstituted or a substituted 1,2,3-triazole (such as

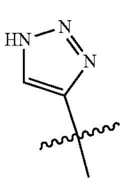 and 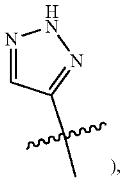), an unsubstituted or a substituted thiazole (for example,

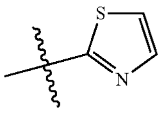 and 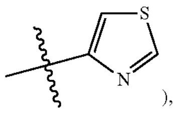), an unsubstituted or a substituted pyridinyl (such as

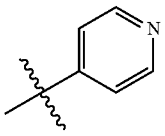, 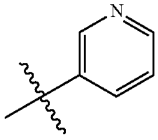 and

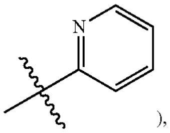), an unsubstituted or a substituted pyrimindine (for example,

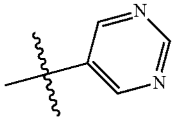 and 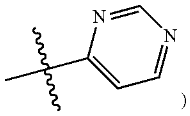)

an unsubstituted or a substituted pyrazole (e.g.,

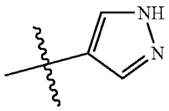, 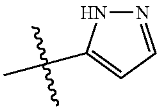 and

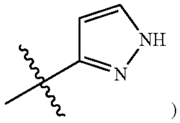)

an unsubstituted or a substituted imidazole (such as

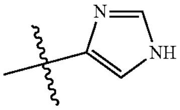 and 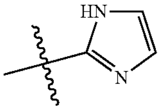)

or an unsubstituted or a substituted oxadiazole (for example,

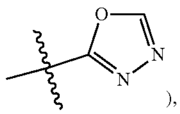 [SMILES: *c1nnco1]

), wherein each of the structures shown can be unsubstituted or substituted (including where a hydrogen on a nitrogen can be replaced with a non-hydrogen substitutent). In some embodiments, $R^1$ can be an unsubstituted bicyclic heteroaryl. In other embodiments, $R^1$ can be a substituted bicyclic heteroaryl. Exemplary bicyclic heteroaryls are provided herein, and include benzimidazole. In some embodiments, $R^1$ can be an unsubstituted monocyclic heterocyclyl. In other embodiments, $R^1$ can be a substituted monocyclic heterocyclyl. Several examples of suitable monocyclic heterocyclyls are described herein. In some embodiments, $R^1$ can be an unsubstituted or substituted 2-oxo-1H-pyridinyl. When cyclic moieties of $R^1$ is substituted, various substituents can be present. Examples of substituents that can be present on the monocyclic heteroaryl of $R^1$ include the following: an unsubstituted $C_{1-4}$ alkyl, an unsubstituted cyclopropyl and an unsubstituted cyclobutyl.

Several substituents can be present at $R^8$. In some embodiments, $R^8$ can be hydrogen. In other embodiments, $R^8$ can be —$CH_2OC({=}O)$-(an unsubstituted $C_{1-4}$ alkyl). For example, $R^8$ can be pivaloyloxymethyl (POM). In still other embodiments, $R^8$ can be —$CH_2OC({=}O)$—O(an unsubstituted $C_{1-4}$ alkyl), such as isopropyloxycarbonyloxymethyl (POC). In yet still other embodiments, $R^8$ can be —$CH_2$-(α-amino acid). Suitable α-amino acids include, but are not limited to, alanine, asparagine, aspartate, cysteine, glutamate, glutamine, glycine, proline, serine, tyrosine, arginine, histidine, isoleucine, leucine, lysine, methionine, phenylalanine, threonine, tryptophan and valine. When $R^8$ includes an α-amino acid, the carboxylic acid moiety is the portion connected to the —$CH_2$ of —$CH_2$-(α-amino acid), and the hydrogen of the carboxylic acid is not present. As some examples, $R^8$ can be

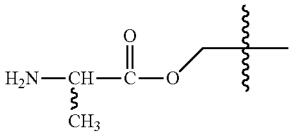

,

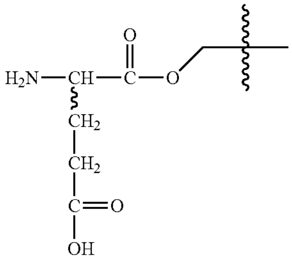

,

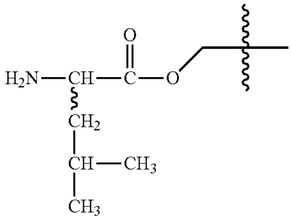

,

-continued

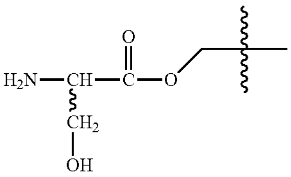

,

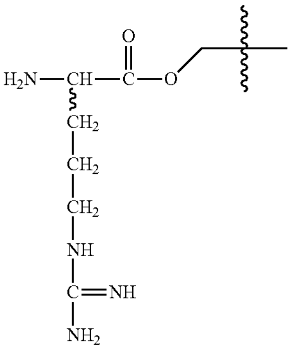

,

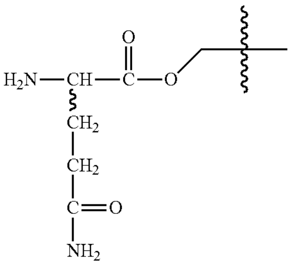

,

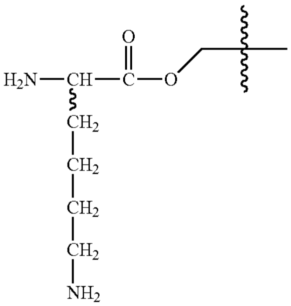

,

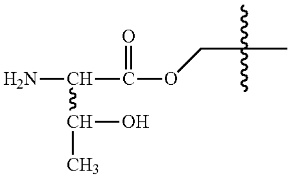

,

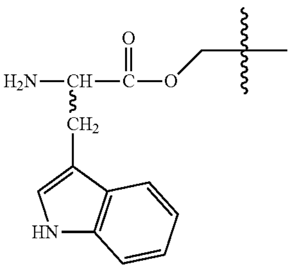

,

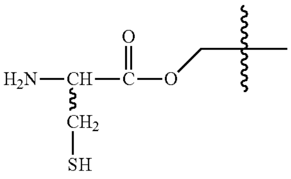

,

-continued

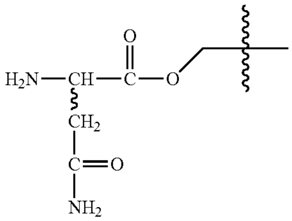

,

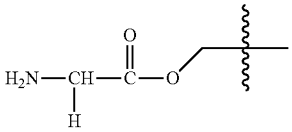

,

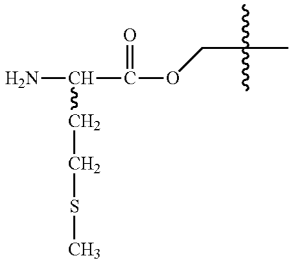

,

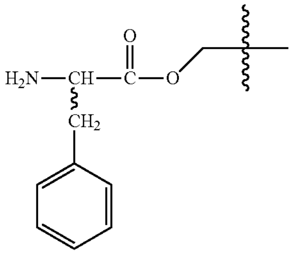

,

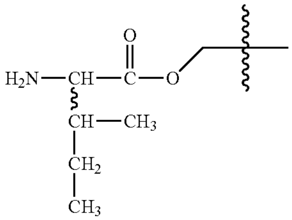

,

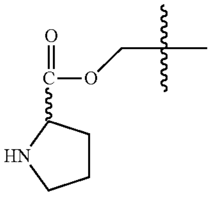

,

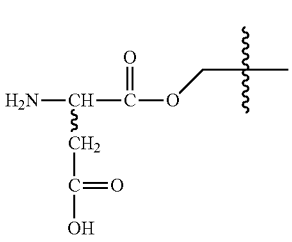

,

-continued

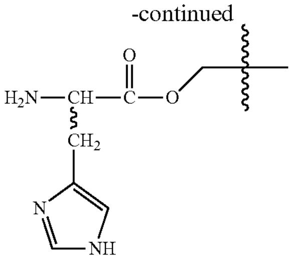

and

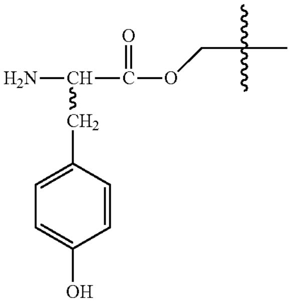

.

In some embodiments, the -α-amino acid of —$CH_2$-(α-amino acid) of $R^8$ can be an L-α-amino acid. In other embodiments, the -α-amino acid of —$CH_2$-(α-amino acid) of $R^8$ can be an D-α-amino acid. In some embodiments, $R^8$ can be —$CH_2$-phosphate ( 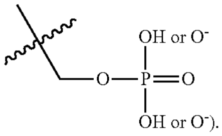 ).

Compounds of Formula (I), along with pharmaceutically acceptable salts thereof, can have a variety of structures. In some embodiments, $R^1$ can be an unsubstituted or a substituted $C_2$ alkenyl, an unsubstituted or a substituted $C_2$ alkynyl, an unsubstituted or a substituted monocyclic heteroaryl, an unsubstituted or a substituted bicyclic heteroaryl or an unsubstituted or a substituted monocyclic heterocyclyl, wherein when the $C_2$ alkenyl, the $C_2$ alkynyl, an unsubstituted $C_{1-4}$ haloalkyl and the monocyclic heteroaryl are substituted, the $C_2$ alkenyl, the $C_2$ alkynyl and the monocyclic heteroaryl are independently substituted with one or more substituents selected from halogen, an unsubstituted $C_{1-4}$ alkyl, an unsubstituted $C_{1-4}$ haloalkyl, an unsubstituted $C_{1-4}$ hydroxyalkyl, an unsubstituted monocyclic $C_{3-6}$ cycloalkyl and a hydroxy-substituted monocyclic $C_{3-6}$ cycloalkyl; $R^2$ and $R^3$ can be independently selected from hydrogen, an unsubstituted or a substituted $C_{1-4}$ alkyl, an unsubstituted $C_{1-4}$ haloalkyl, an unsubstituted or a substituted monocyclic $C_{3-6}$ cycloalkyl, an unsubstituted or a substituted monocyclic 3-6 membered heterocyclyl, an unsubstituted $C_{1-4}$ hydroxyalkyl and an unsubstituted $C_{1-5}$ alkoxyalkyl, wherein when the monocyclic $C_{3-6}$ cycloalkyl and the monocyclic 3-6 heterocyclyl are substituted, the monocyclic $C_{3-6}$ cycloalkyl and the monocyclic 3-6 heterocyclyl are independently substituted with one or more substituents selected from halogen or hydroxy, and wherein when the $C_{1-4}$ alkyl is substituted, the $C_{1-4}$ alkyl is substituted with one or more substituents selected from a phosphate, an O-linked α-amino acid and an O-carboxy, and provided that at least one of $R^2$ and $R^3$ is not hydrogen; $R^4$ and $R^5$ can be independently hydrogen, halogen, an unsubstituted $C_{1-4}$ alkyl, a deuterated $C_{1-4}$ alkyl or an unsubstituted $C_{2-4}$ alkenyl; $R^6$ can be hydrogen, an unsubstituted $C_{1-4}$ alkyl, a deuterated $C_{1-4}$ alkyl or an unsubstituted $C_{3-4}$ alkenyl; and provided that at least one of $R^4$, $R^5$ and $R^6$ is not hydrogen; $X^1$ can be $CR^A$ or N; $R^{7a}$, $R^{7b}$, $R^{7c}$ and $R^{7d}$ can be independently hydrogen, halogen, an unsubstituted $C_{1-4}$ haloalkyl, cyano or an unsubstituted $C_{1-4}$ alkoxy; $R^8$ can be hydrogen, —$CH_2OC$(═O)-(an unsubstituted $C_{1-4}$ alkyl), —$CH_2OC$(═O)—O(an unsubstituted $C_{1-4}$ alkyl), —$CH_2$-(α-amino acid) or —$CH_2$-phosphate; and $R^A$ can be hydrogen, halogen, an unsubstituted $C_{1-4}$ haloalkyl or cyano. For this paragraph, when at least one of $R^2$ and $R^3$ is not hydrogen, the following for $R^2$ and $R^3$ are provided: (1) $R^2$ and $R^3$ can be each an unsubstituted $C_{1-4}$ alkyl, such as methyl, (2) a $C_{1-4}$ alkyl substituted by a phosphate, an O-linked α-amino acid or an O-carboxy (for example, —O(C═O)(an unsubstituted $C_{1-4}$ alkyl), (3) an unsubstituted $C_{1-4}$ haloalkyl (for example, $CF_3$), (4) an unsubstituted cyclopropyl and (5) an unsubstituted $C_{1-4}$ hydroxyalkyl (such as —$CH_2OH$).

In other embodiments, $R^1$ can be an unsubstituted or a substituted $C_2$ alkenyl, an unsubstituted or a substituted $C_2$ alkynyl, an unsubstituted or a substituted monocyclic heteroaryl, an unsubstituted or a substituted bicyclic heteroaryl or an unsubstituted or a substituted monocyclic heterocyclyl, wherein when the $C_2$ alkenyl, the $C_2$ alkynyl, an unsubstituted $C_{1-4}$ haloalkyl and the monocyclic heteroaryl are substituted, the $C_2$ alkenyl, the $C_2$ alkynyl and the monocyclic heteroaryl are independently substituted with one or more substituents selected from halogen, an unsubstituted $C_{1-4}$ alkyl, an unsubstituted $C_{1-4}$ haloalkyl, an unsubstituted $C_{1-4}$ hydroxyalkyl, an unsubstituted monocyclic $C_{3-6}$ cycloalkyl and a hydroxy-substituted monocyclic $C_{3-6}$ cycloalkyl; $R^2$ and $R^3$ can be taken together along with the carbon to which $R^2$ and $R^3$ are attached to form an unsubstituted or a substituted monocyclic $C_{3-6}$ cycloalkyl or an unsubstituted or a substituted monocyclic 3-6 membered heterocyclyl, wherein when the $C_{3-6}$ cycloalkyl and 3-6 membered heterocyclyl are substituted, the $C_{3-6}$ cycloalkyl and the 3-6 membered heterocyclyl are independently substituted with 1 or 2 substituents selected from halogen and hydroxy; $R^4$ and $R^5$ can be independently hydrogen, halogen, an unsubstituted $C_{1-4}$ alkyl, a deuterated $C_{1-4}$ alkyl or an unsubstituted $C_{2-4}$ alkenyl; $R^6$ can be hydrogen, an unsubstituted $C_{1-4}$ alkyl, a deuterated $C_{1-4}$ alkyl or an unsubstituted $C_{3-4}$ alkenyl; and provided that at least one of $R^4$, $R^5$ and $R^6$ is not hydrogen; $X^1$ can be $CR^A$ or N; $R^{7a}$, $R^{7b}$, $R^{7c}$ and $R^{7d}$ can be independently hydrogen, halogen, an unsubstituted $C_{1-4}$ haloalkyl, cyano or an unsubstituted $C_{1-4}$ alkoxy; $R^8$ can be hydrogen, —$CH_2OC$(═O)-(an unsubstituted $C_{1-4}$ alkyl), —$CH_2OC$(═O)—O(an unsubstituted $C_{1-4}$ alkyl), —$CH_2$-(α-amino acid) or —$CH_2$-phosphate; and $R^A$ can be hydrogen, halogen, an unsubstituted $C_{1-4}$ haloalkyl or cyano. As provided herein, $R^2$ and $R^3$ can be taken together along with the carbon to which $R^2$ and $R^3$ are attached form an unsubstituted cyclobutyl, a fluoro-substituted cyclobutyl, a hydroxy-substituted cyclobutyl or an unsubstituted oxetane.

In still other embodiments, $R^1$ can be an unsubstituted or a substituted $C_2$ alkenyl, an unsubstituted or a substituted $C_2$ alkynyl, an unsubstituted $C_{1-4}$ haloalkyl, an unsubstituted or a substituted monocyclic heteroaryl, an unsubstituted or a substituted bicyclic heteroaryl or an unsubstituted or a substituted monocyclic heterocyclyl, wherein when the $C_2$ alkenyl, the $C_2$ alkynyl and the monocyclic heteroaryl are substituted, the $C_2$ alkenyl, the $C_2$ alkynyl and the monocyclic heteroaryl can be independently substituted with one or more substituents selected from halogen, an unsubstituted $C_{1-4}$ alkyl, an unsubstituted $C_{1-4}$ haloalkyl, an unsubstituted $C_{1-4}$ hydroxyalkyl, an unsubstituted monocyclic $C_{3-6}$ cycloalkyl and a hydroxy-substituted monocyclic $C_{3-6}$ cycloalkyl; $R^2$ and $R^3$ can be independently selected from hydrogen, an unsubstituted or a substituted $C_{1-4}$ alkyl, an unsubstituted $C_{1-4}$ haloalkyl, an unsubstituted or a substituted monocyclic $C_{3-6}$ cycloalkyl, an unsubstituted or a substituted monocyclic 3-6 membered heterocyclyl, an unsubstituted $C_{1-4}$ hydroxyalkyl and an unsubstituted $C_{1-5}$ alkoxyalkyl, wherein when the monocyclic $C_{3-6}$ cycloalkyl and the monocyclic 3-6 heterocyclyl are substituted, the monocyclic $C_{3-6}$ cycloalkyl and the monocyclic 3-6 heterocyclyl can be independently substituted with one or more substituents selected from halogen or hydroxy, and wherein when the $C_{1-4}$ alkyl is substituted, the $C_{1-4}$ alkyl is substituted with one or more substituents selected from the group consisting of a phosphate, an O-linked α-amino acid and an O-carboxy; or $R^2$ and $R^3$ can be taken together along with the carbon to which $R^2$ and $R^3$ are attached to form an unsubstituted or a substituted monocyclic $C_{3-6}$ cycloalkyl or an unsubstituted or a substituted monocyclic 3-6 membered heterocyclyl, wherein when the $C_{3-6}$ cycloalkyl and 3-6 membered heterocyclyl are substituted, the $C_{3-6}$ cycloalkyl and the 3-6 membered heterocyclyl can be independently substituted with 1 or 2 substituents selected from halogen and hydroxy; $R^5$ can be hydrogen, halogen, an unsubstituted $C_{1-4}$ alkyl or an unsubstituted $C_{2-4}$ alkenyl; and $R^4$ and $R^6$ can be taken together to form an unsubstituted or substituted 5-6 membered heterocyclic ring; $X^1$ can be $CR^A$ or N (nitrogen); $R^{7a}$, $R^{7b}$, $R^{7c}$ and $R^{7d}$ can be independently hydrogen, halogen, an unsubstituted $C_{1-4}$ haloalkyl, cyano or an unsubstituted $C_{1-4}$ alkoxy; $R^8$ can be hydrogen, —$CH_2OC$(═O)-(an unsubstituted $C_{1-4}$ alkyl), —$CH_2OC$(═O)—O(an unsubstituted $C_{1-4}$ alkyl), —$CH_2$-(α-amino acid) or —$CH_2$— phosphate; and $R^A$ can be hydrogen, halogen, an unsubstituted $C_{1-4}$ haloalkyl or cyano.

Examples of compound of Formula (I), or a pharmaceutically acceptable salt thereof, include the following:

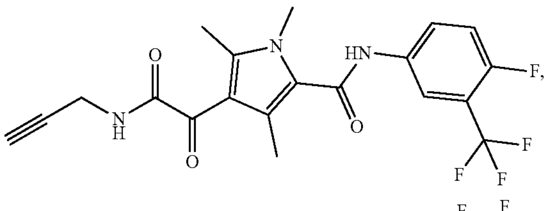

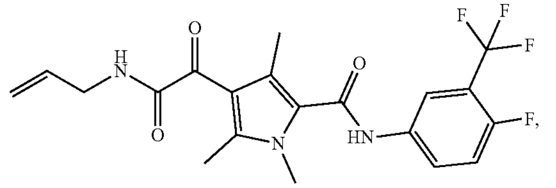

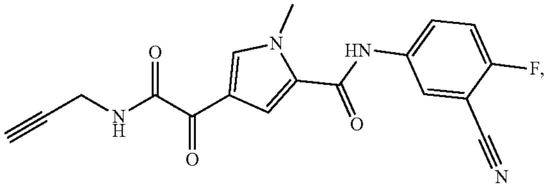

-continued
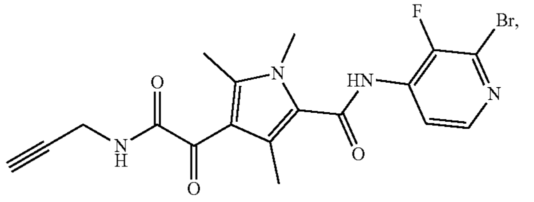
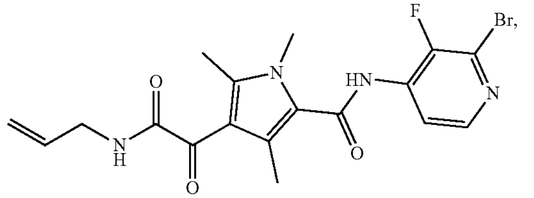
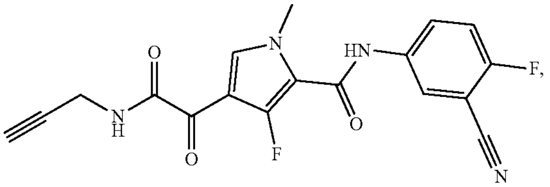
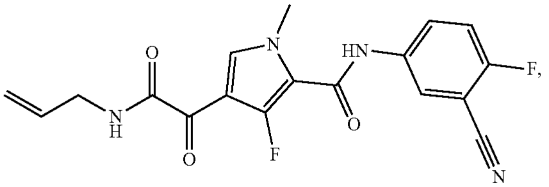
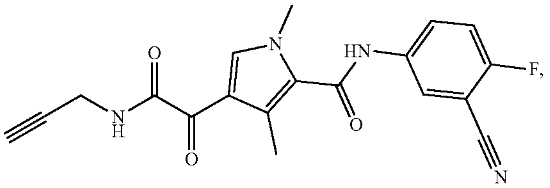
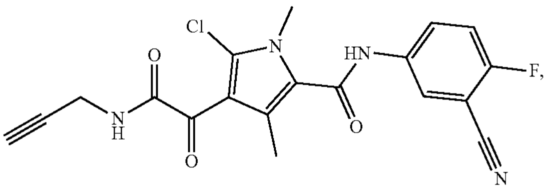
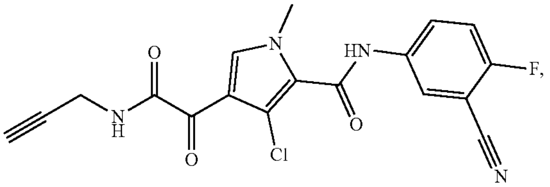
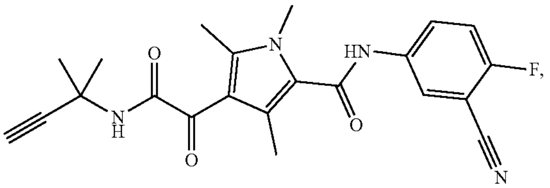
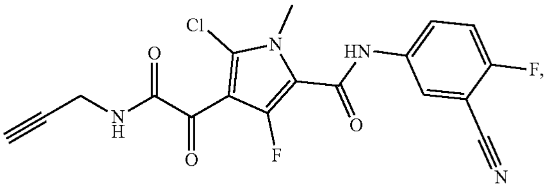
-continued
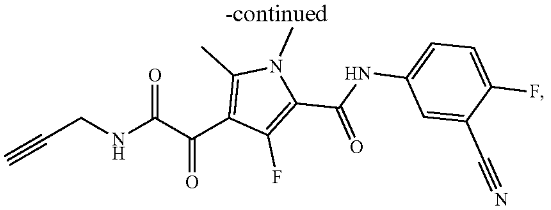
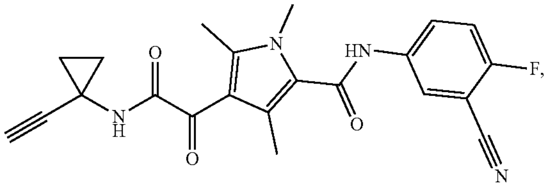
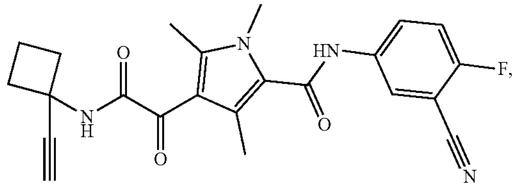
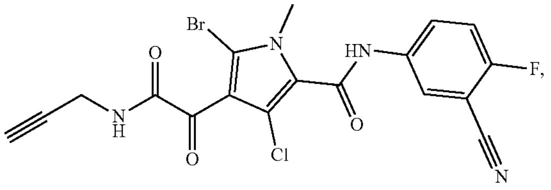
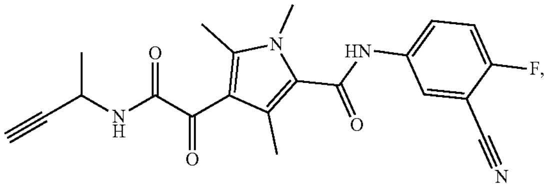
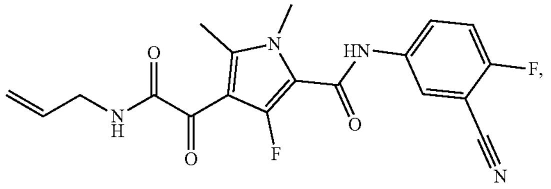
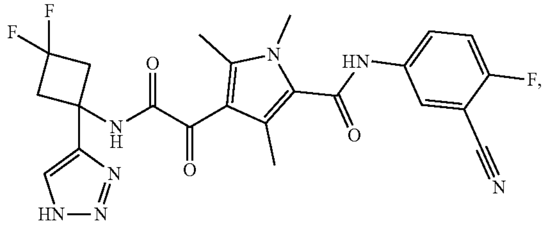
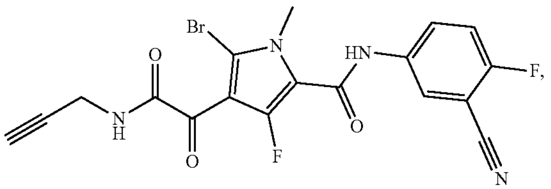
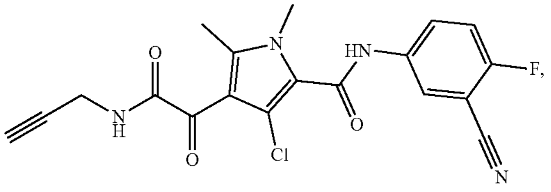

-continued
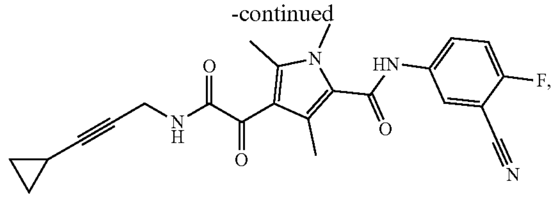
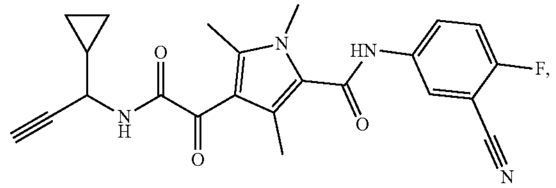
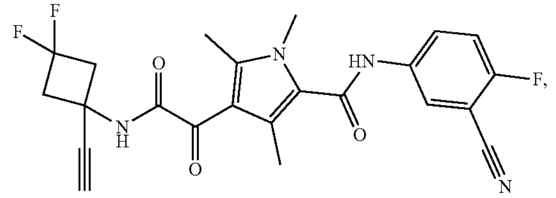
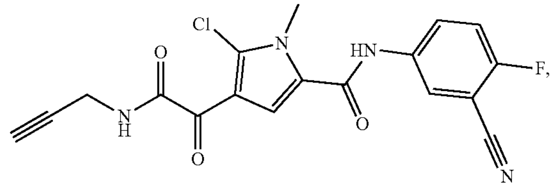
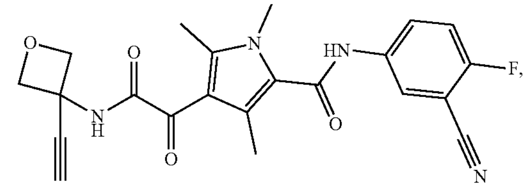
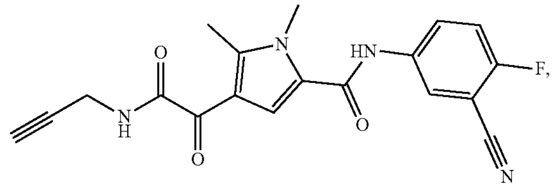
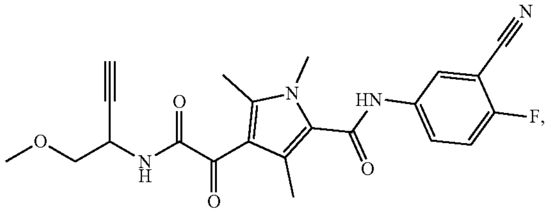
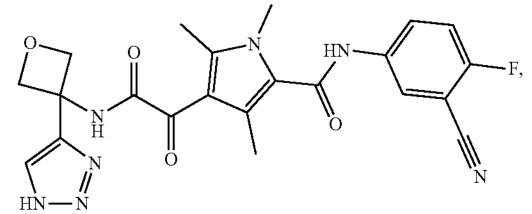
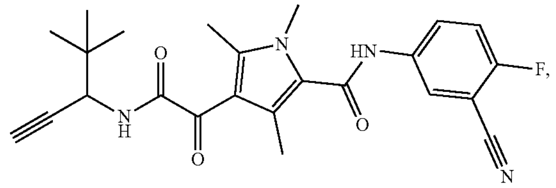
-continued
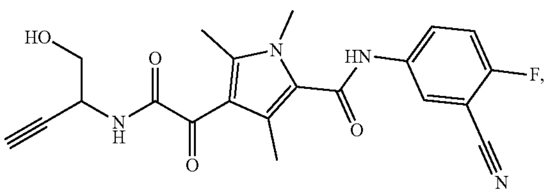
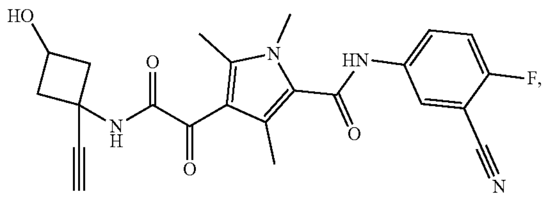
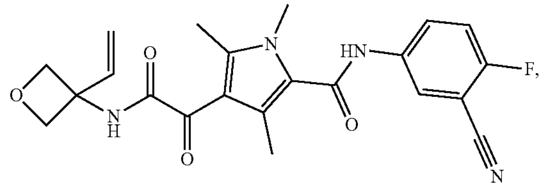
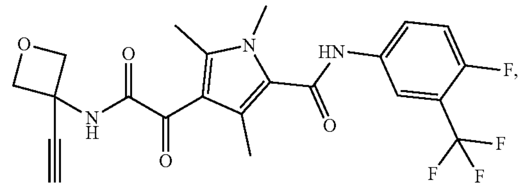
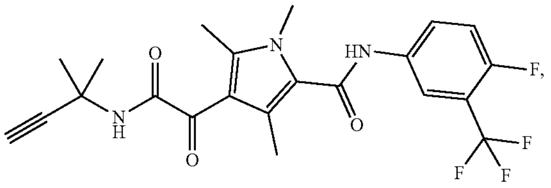
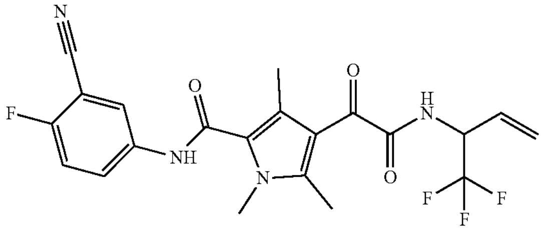
,
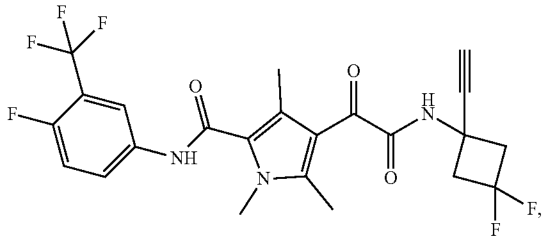
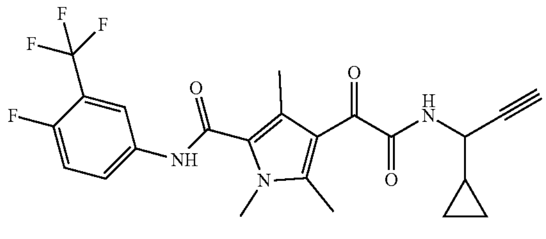
, -continued
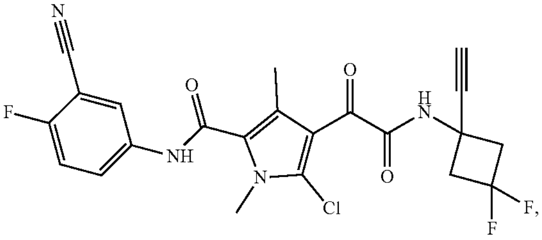
,
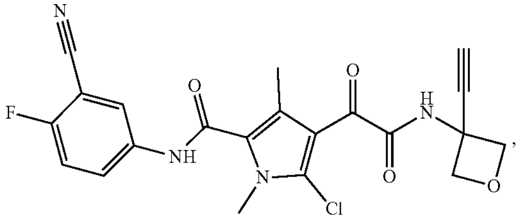
,
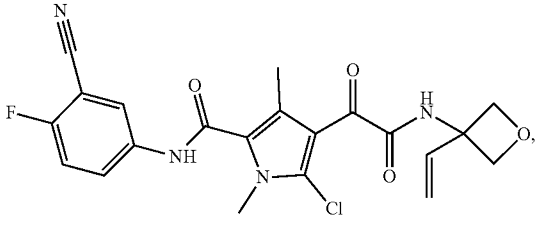
,
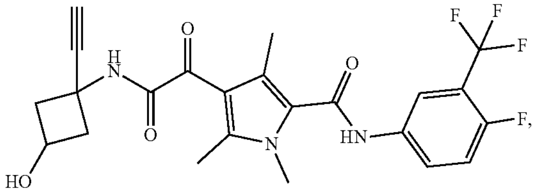
,
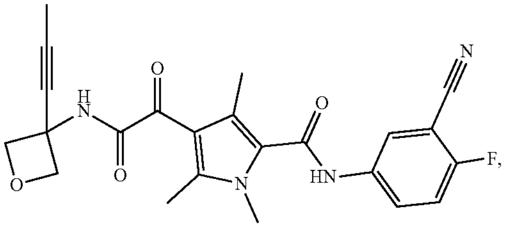
,
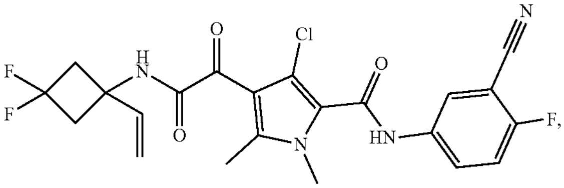
,
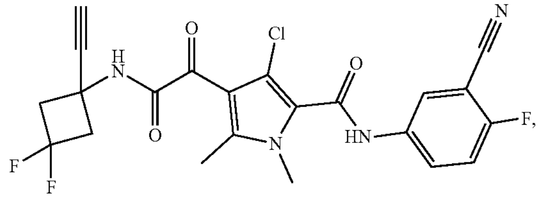
,
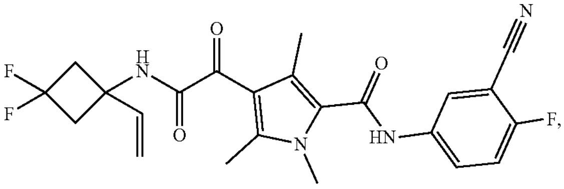
,
-continued
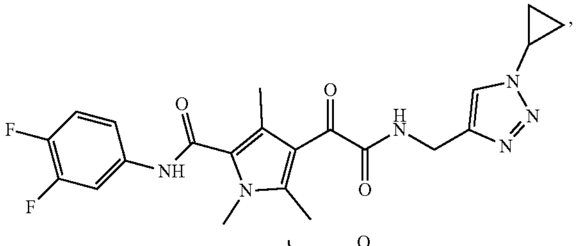
,
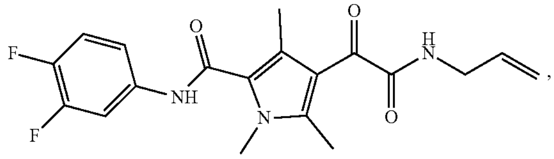
,
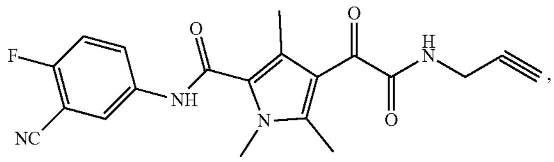
,
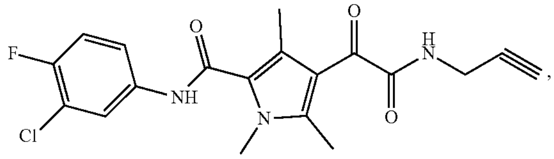
,
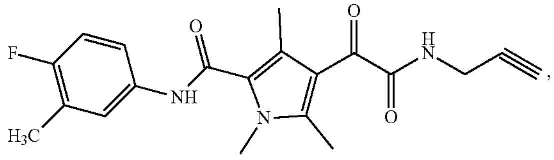
,
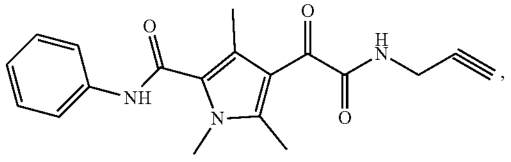
,
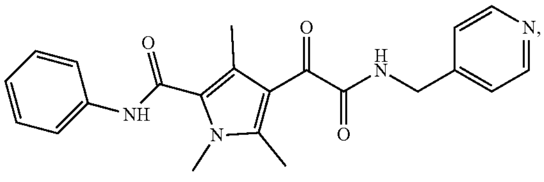
,
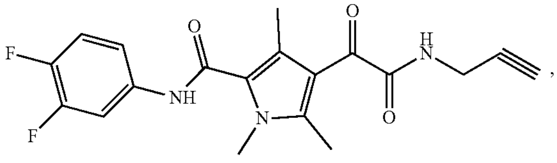
,
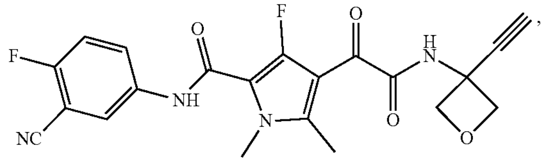
,
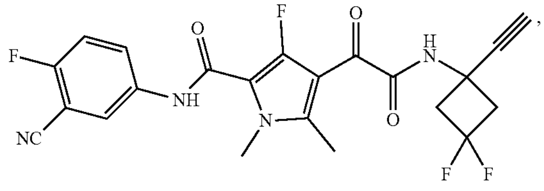
, -continued
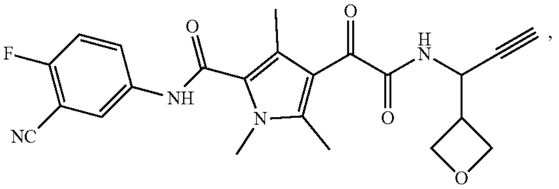
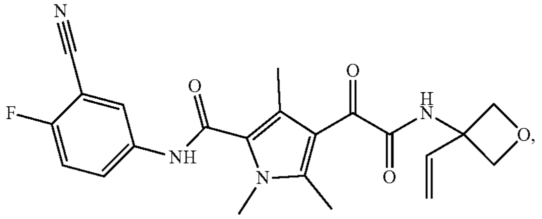
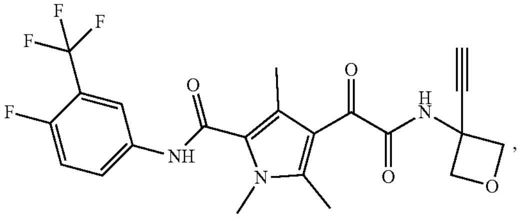
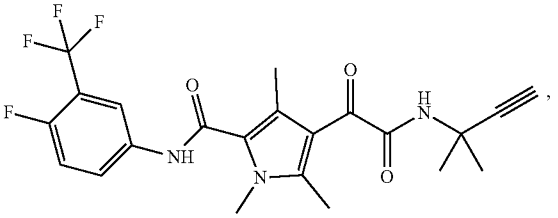
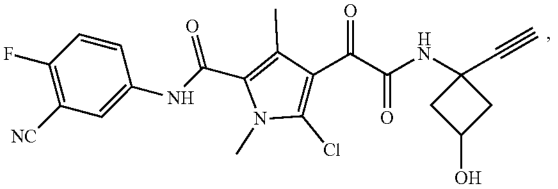
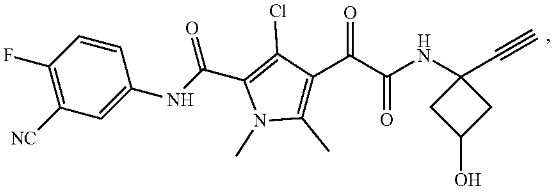
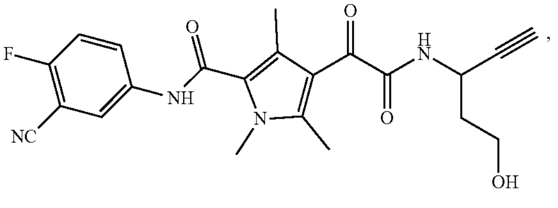
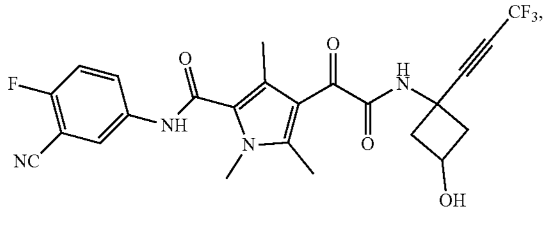
-continued
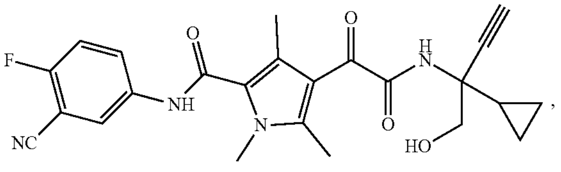
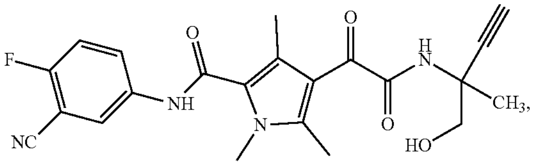
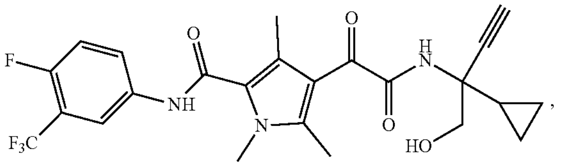
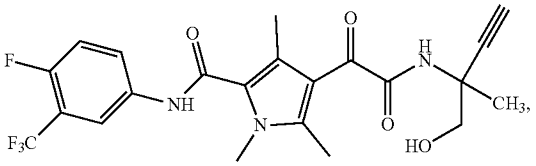
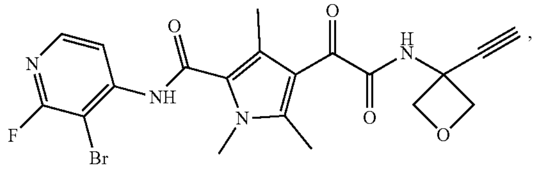
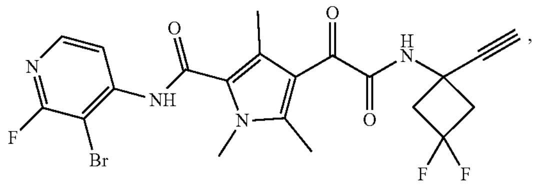
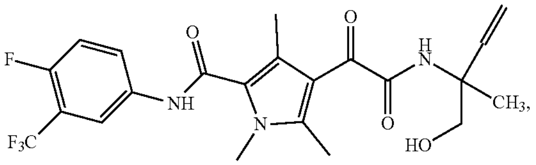
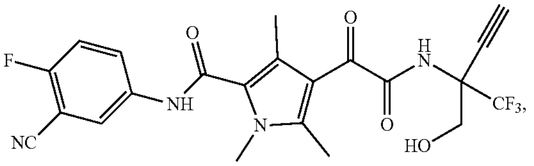
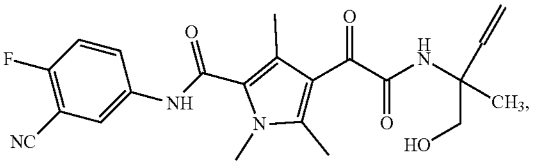

-continued
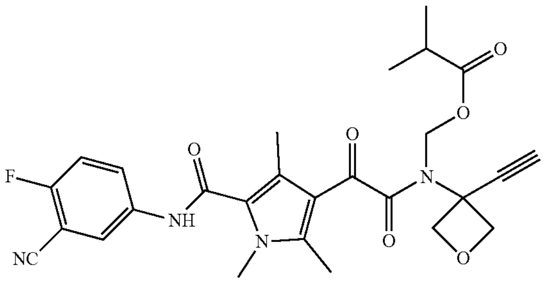,
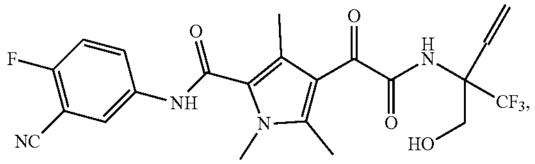,
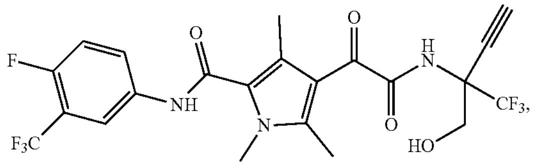,
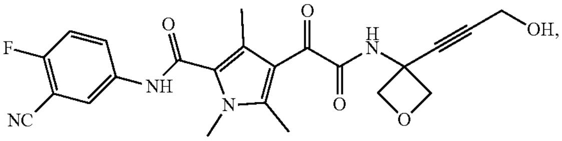,
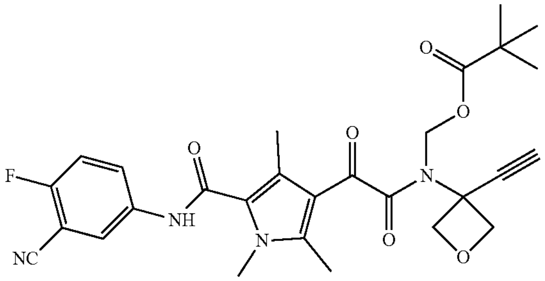,
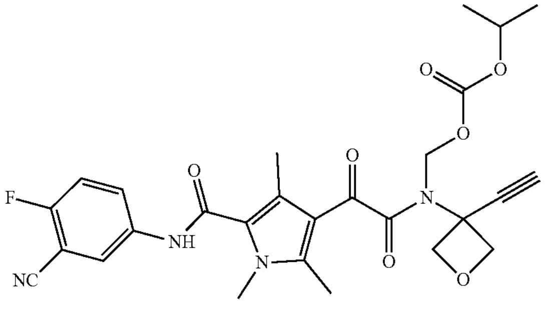,
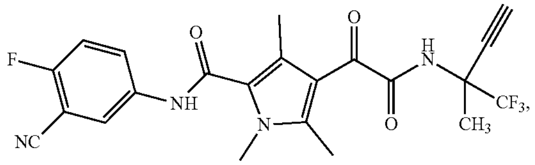,
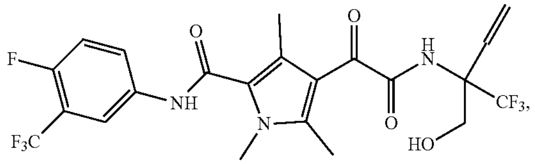,
-continued
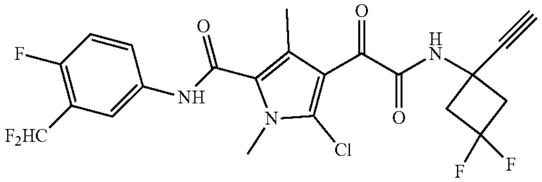,
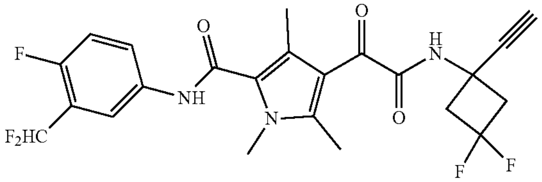,
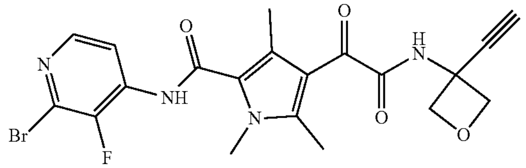,
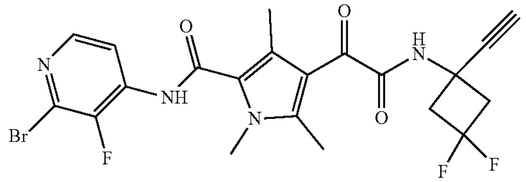,
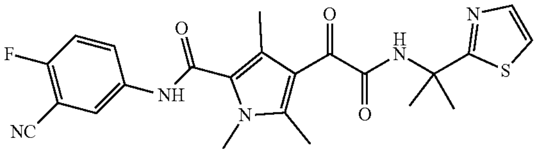,
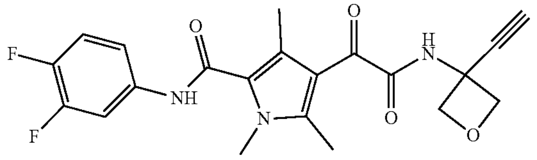,
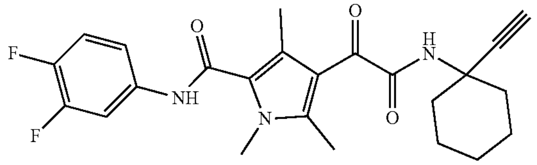,
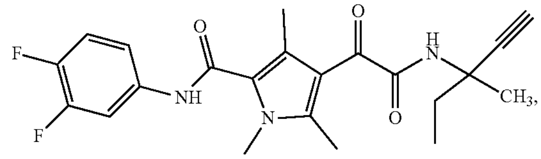,
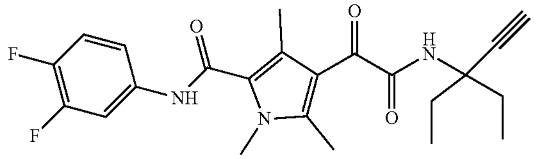,
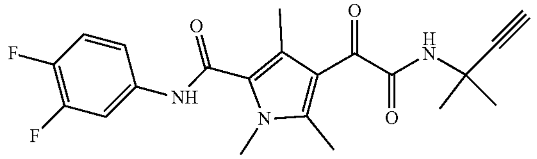, -continued
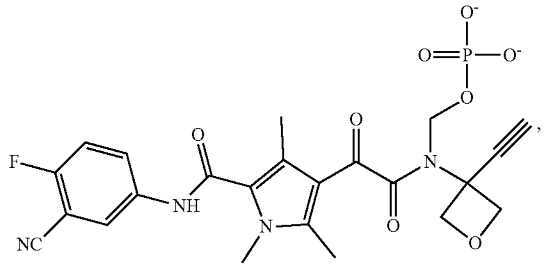
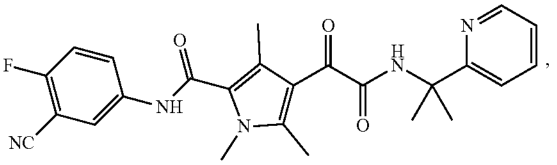
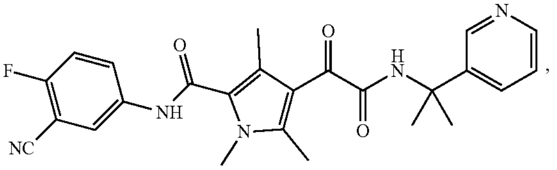
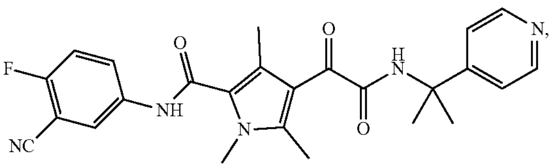
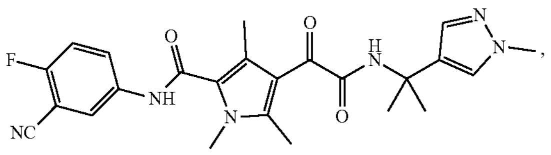
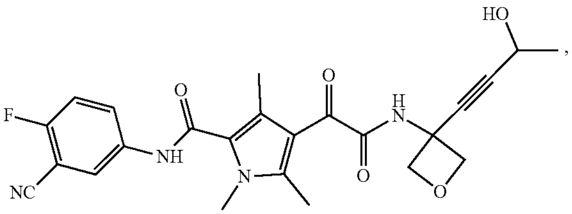
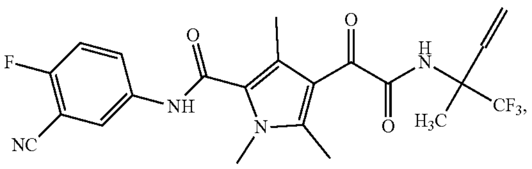
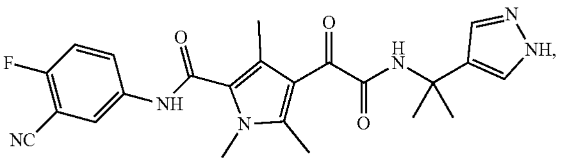
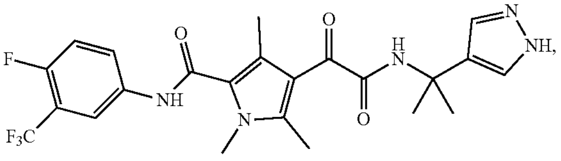
-continued
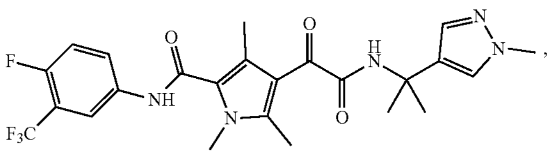
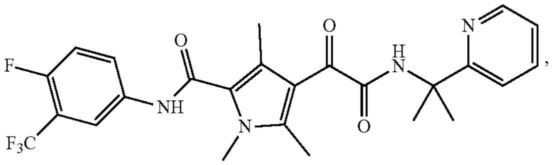
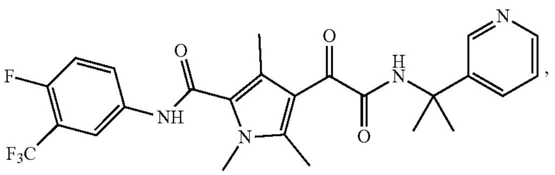
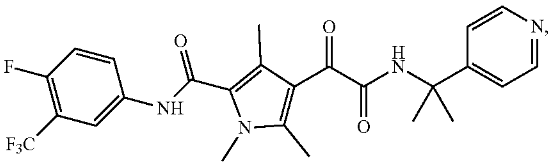
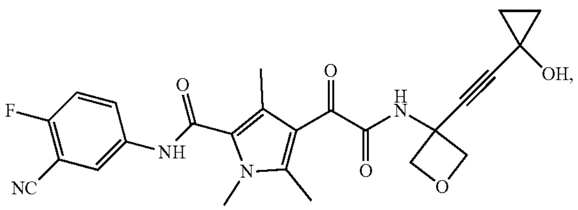
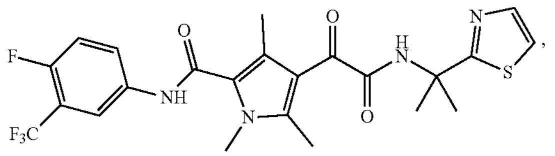
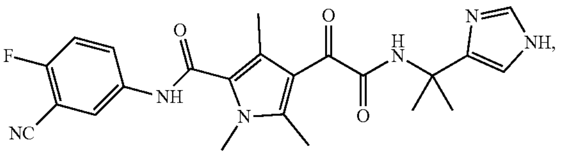
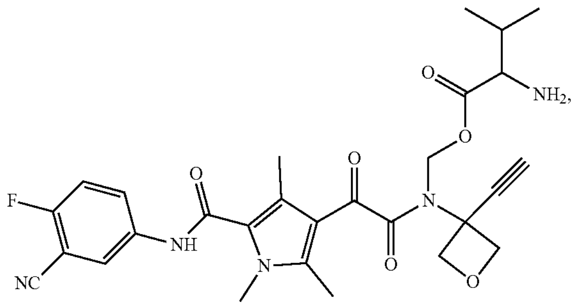
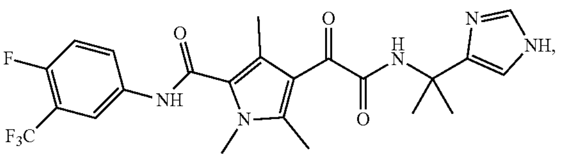

-continued
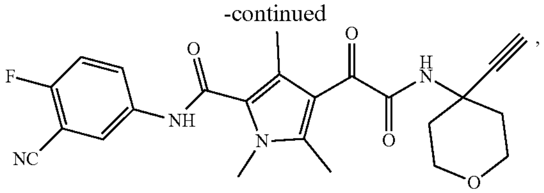,
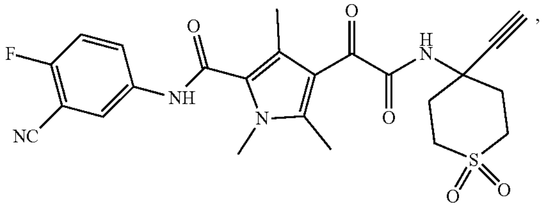,
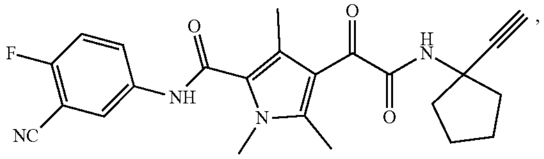,
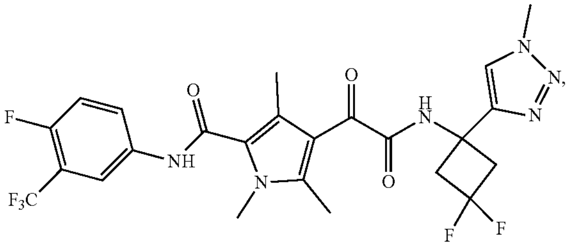,
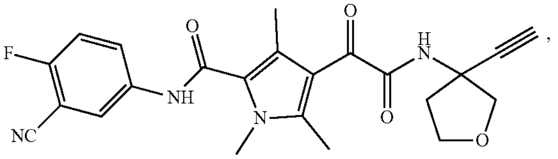,
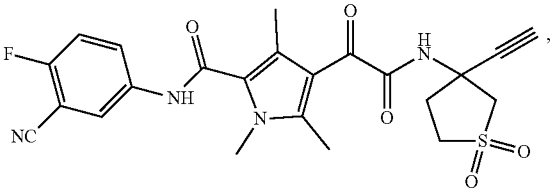,
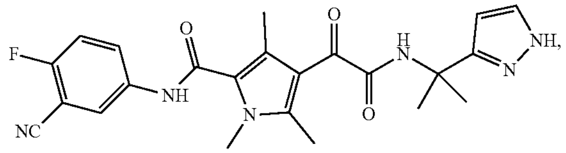,
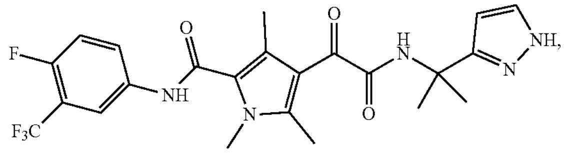,
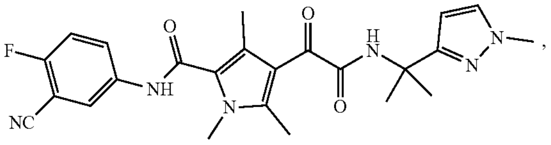,
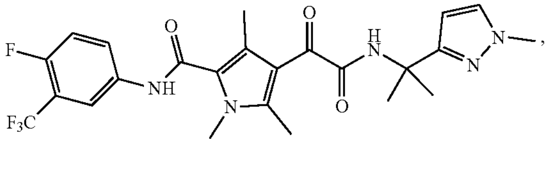,
-continued
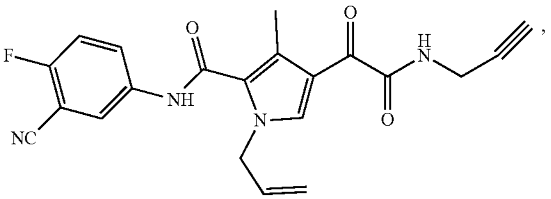,
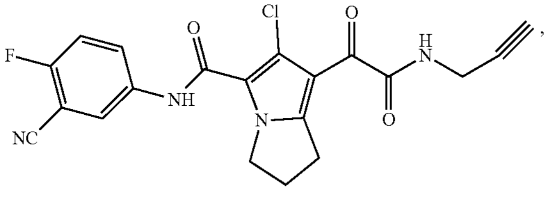,
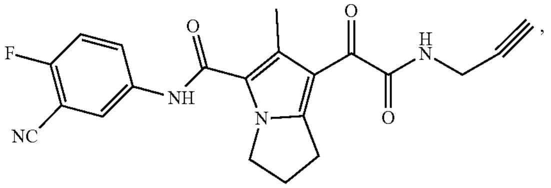,
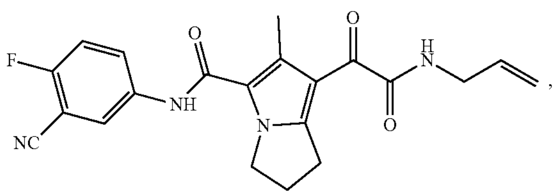,
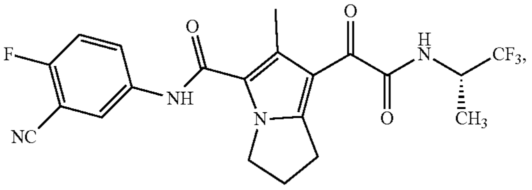,
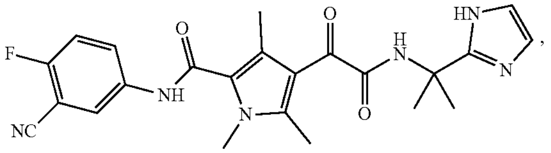,
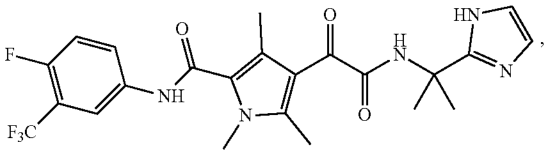,
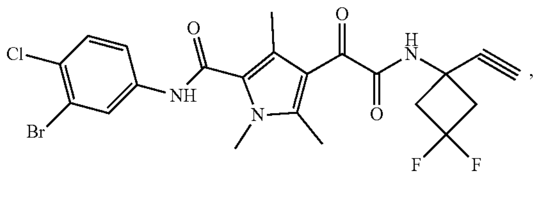,
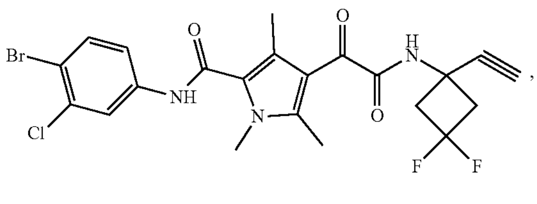, -continued
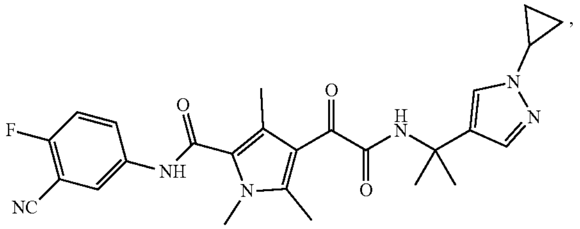
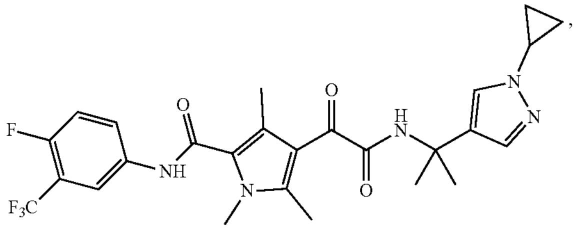
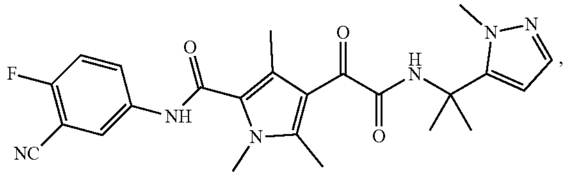
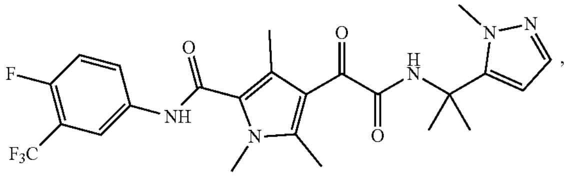
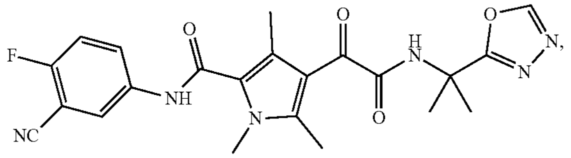
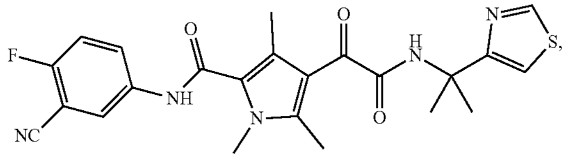
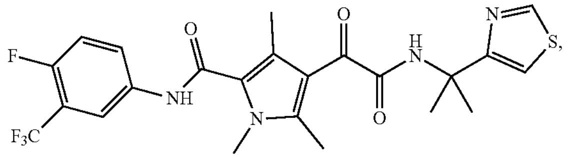
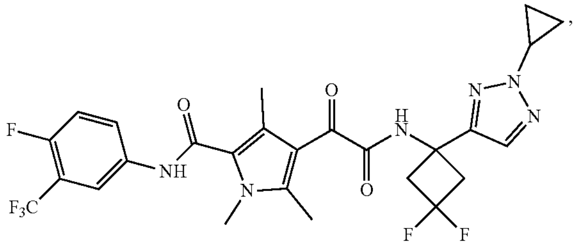
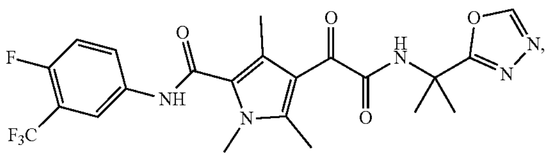
-continued
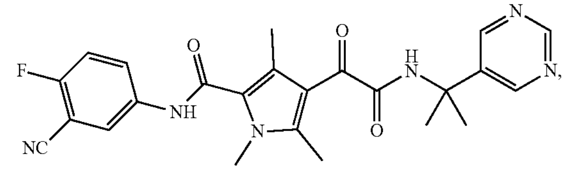
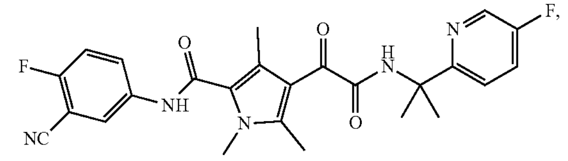
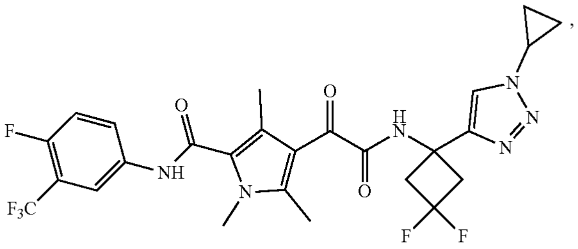
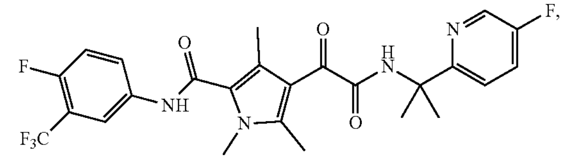
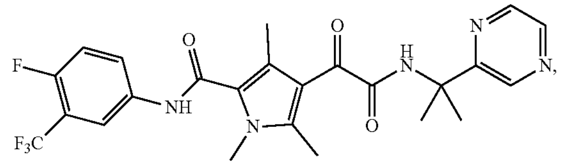
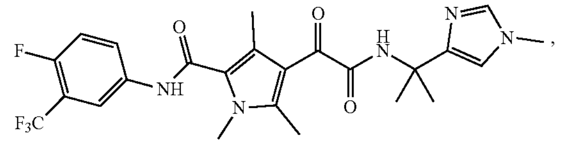
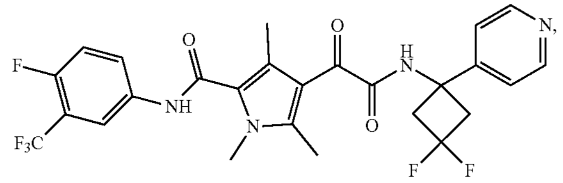
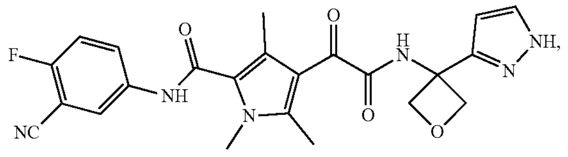
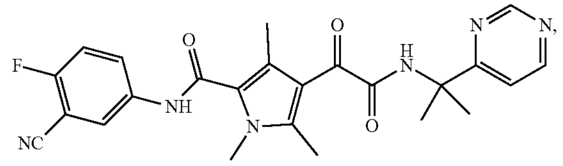
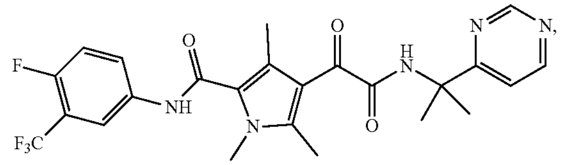

-continued
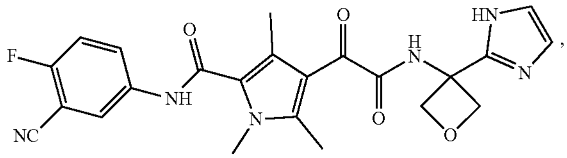,
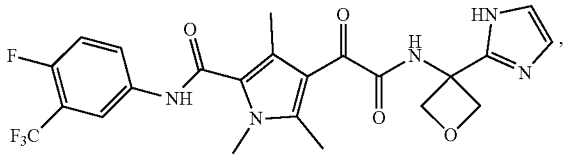,
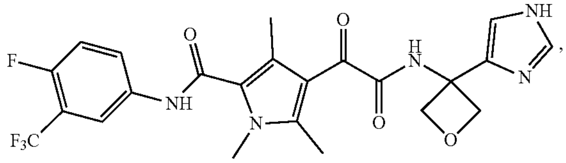,
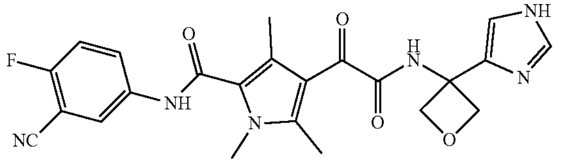,
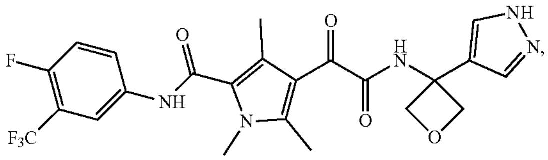,
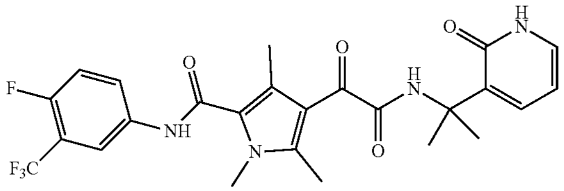,
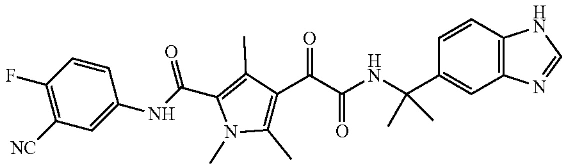,
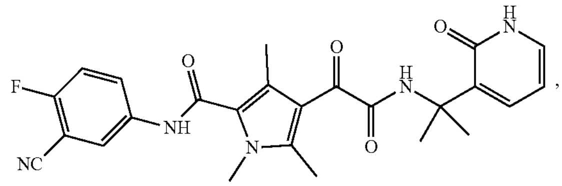,
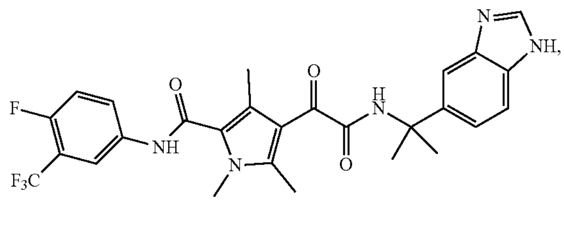,
-continued
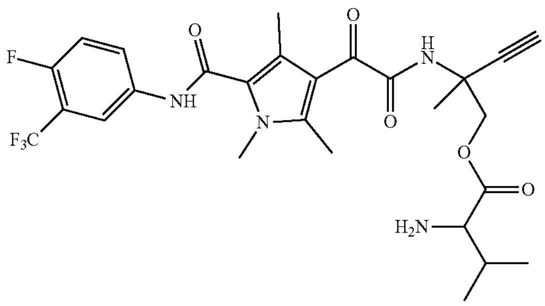,
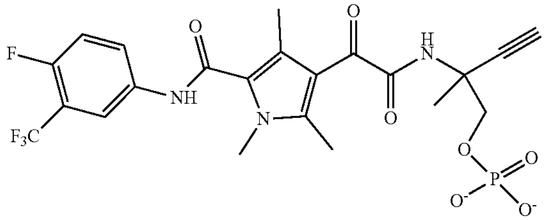,
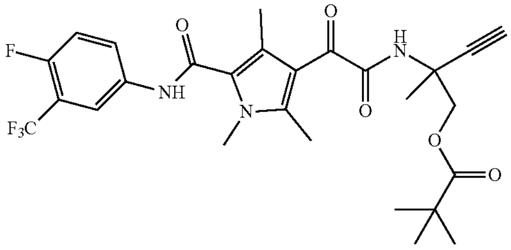
and
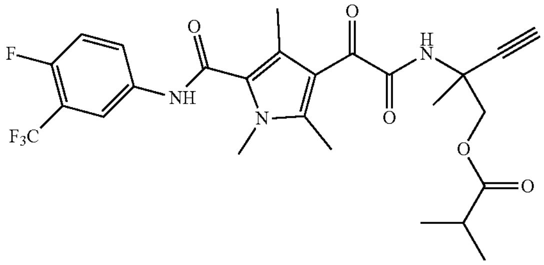,
or a pharmaceutically acceptable salt of any of the foregoing.
Further examples of compound of Formula (I), or a pharmaceutically acceptable salt thereof, include the following:
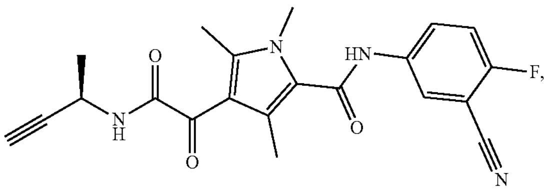,
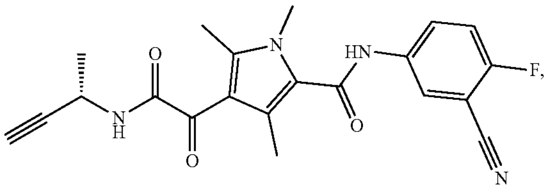, -continued
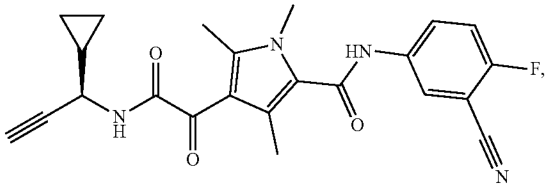,
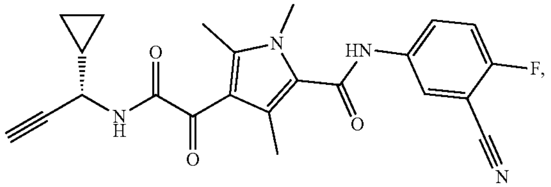,
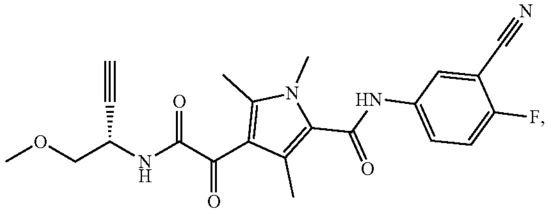,
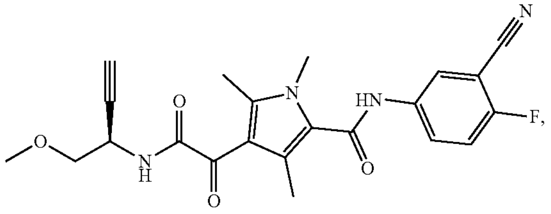,
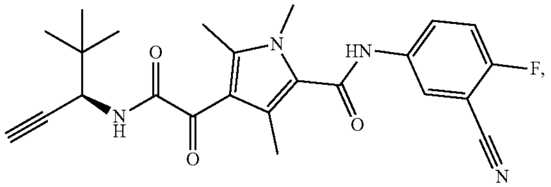,
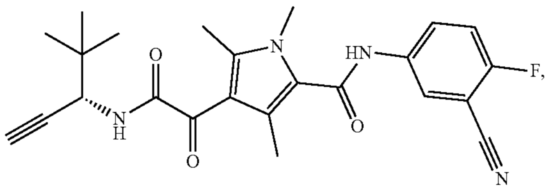,
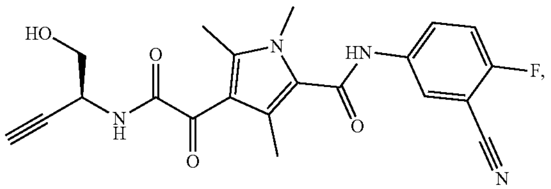,
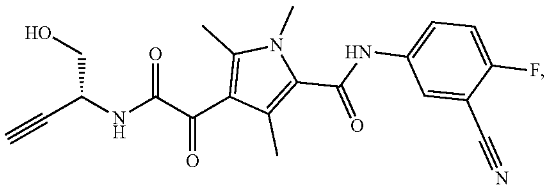,
-continued
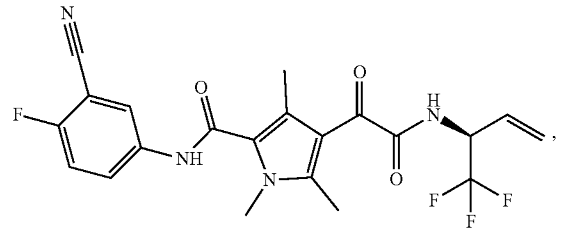,
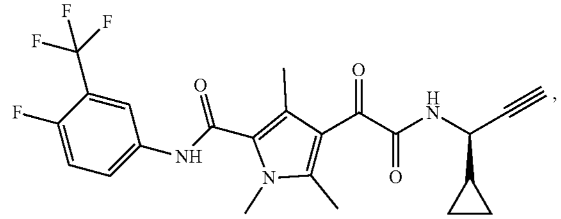,
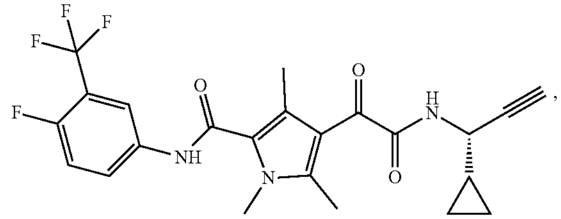,
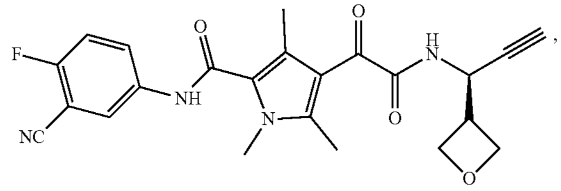,
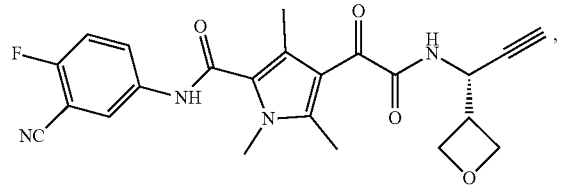,
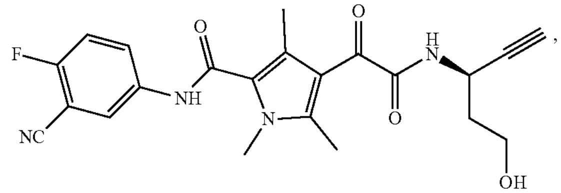,
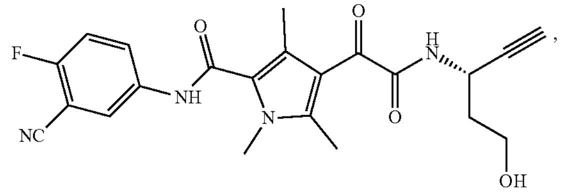,
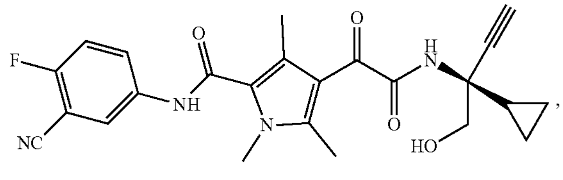, -continued
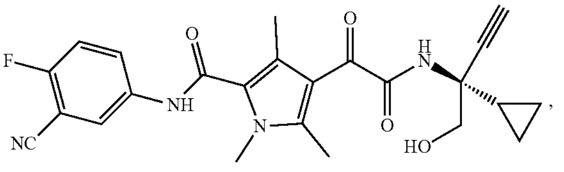
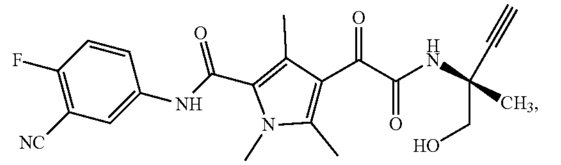
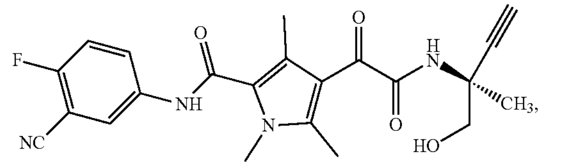
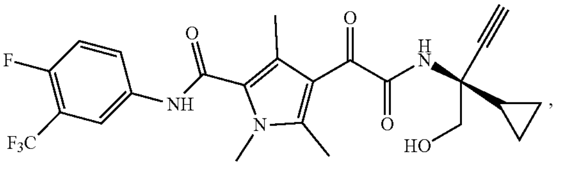
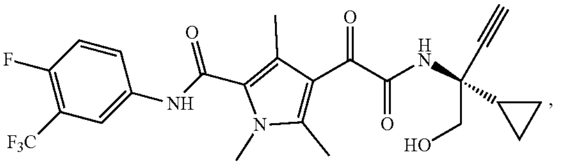
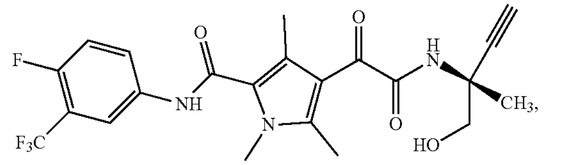
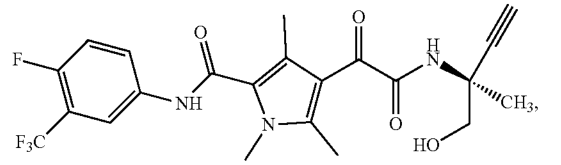
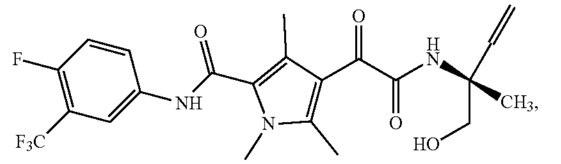
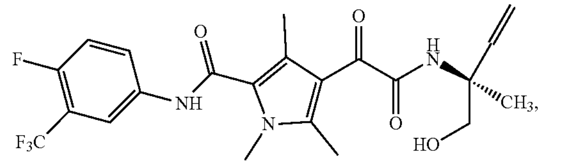
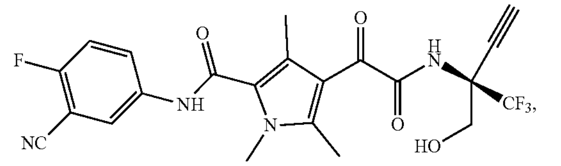
-continued
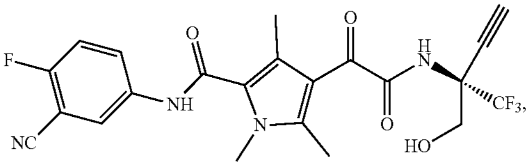
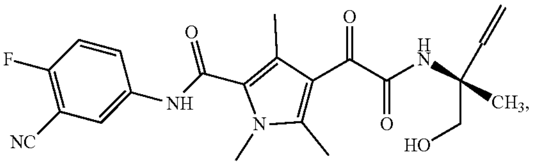
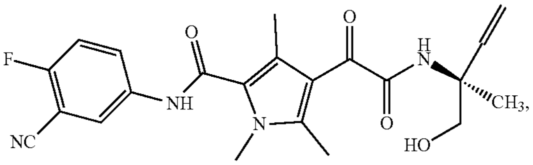
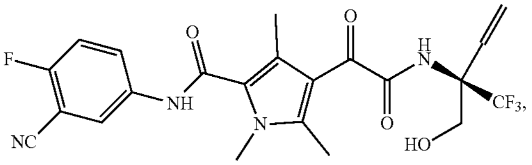
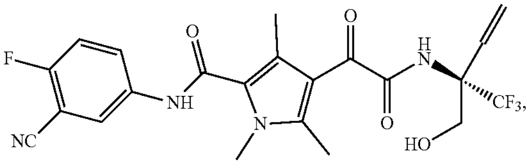
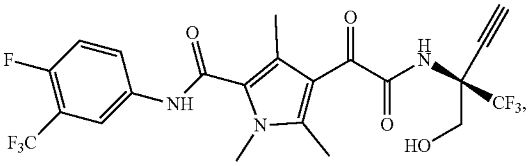
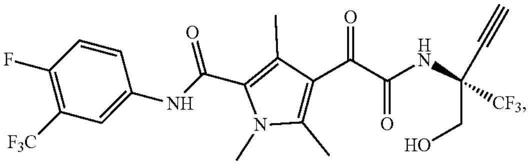
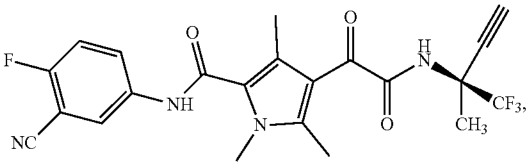
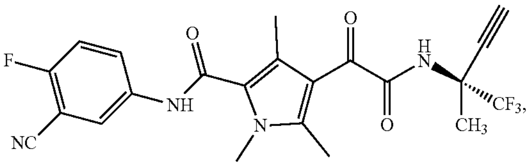
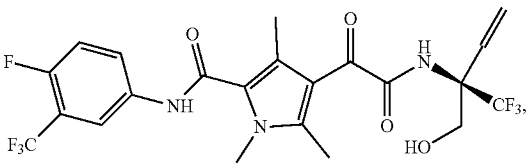

-continued
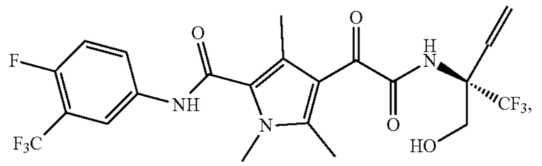
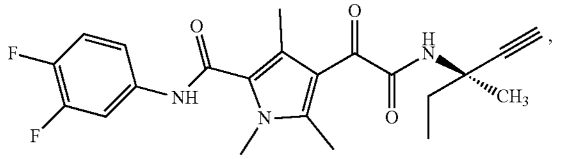
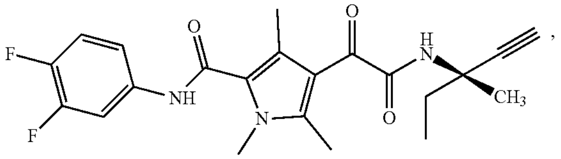
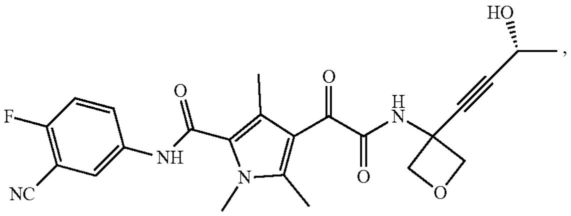
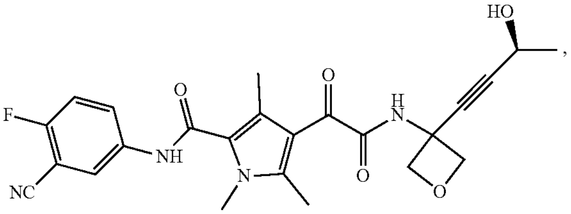
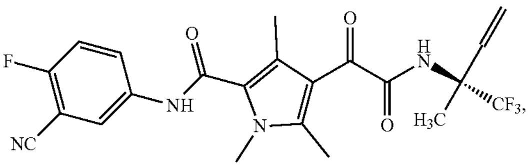
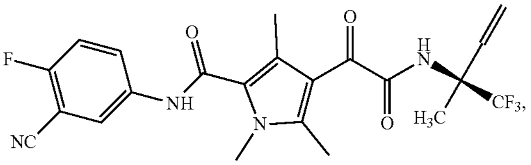
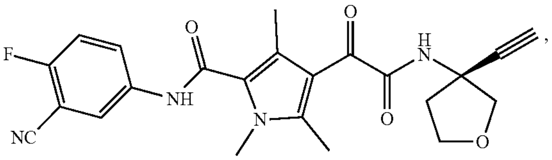
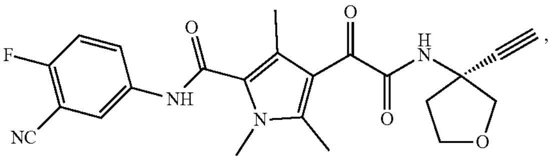
-continued
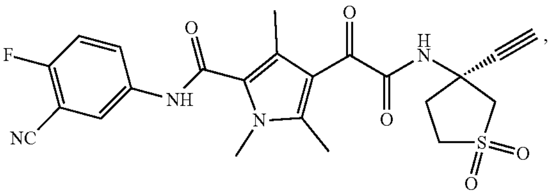
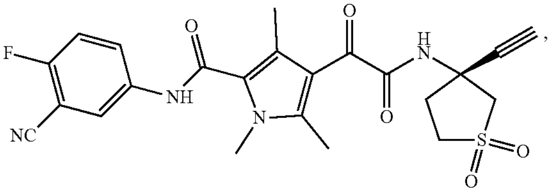
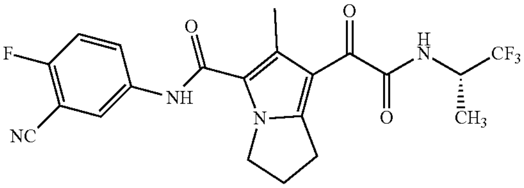
and
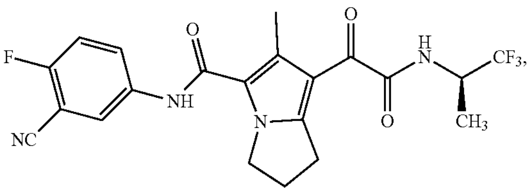
or a pharmaceutically acceptable salt of any of the foregoing.
In some embodiments, a compound of Formula (I), or a pharmaceutically acceptable salt, cannot be one or more of the following compounds:
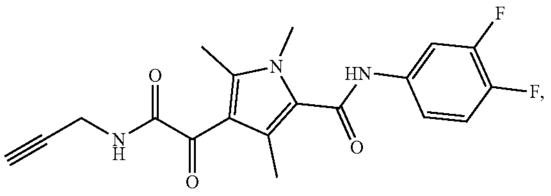
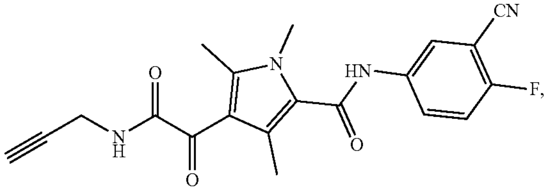
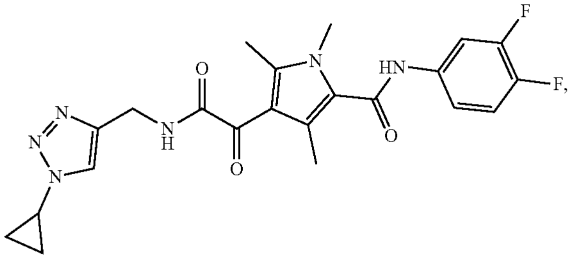

-continued

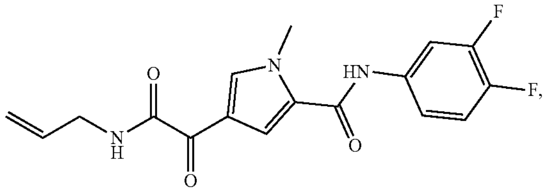

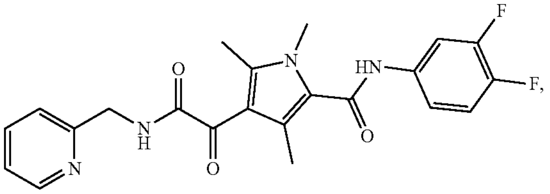

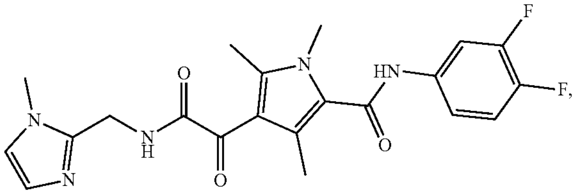

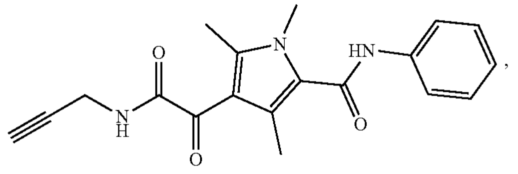

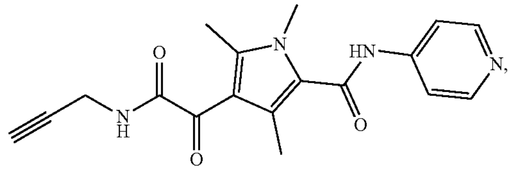

-continued

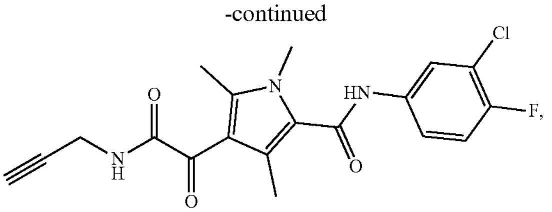

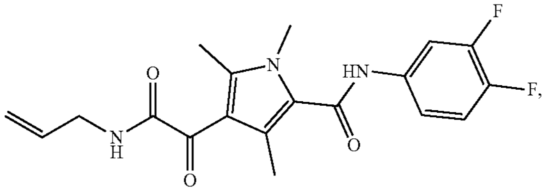

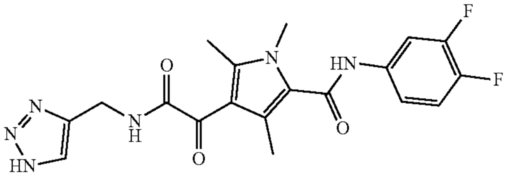

and

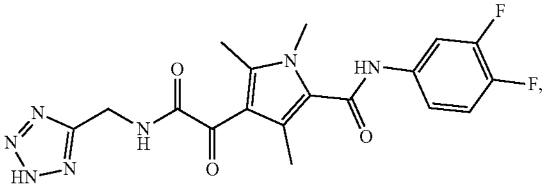

or a pharmaceutically acceptable salt of any of the foregoing. In some embodiments, a compound of Formula (I), or a pharmaceutically acceptable salt, cannot be a compound provided in WO 2017/156255. In some embodiments, $R^1$ cannot be a difluoro-substituted phenyl. In some embodiments, $R^1$ cannot be an unsubstituted or substituted tetrazole, an unsubstituted or substituted 1,2,3-triazole and/or an unsubstituted or substituted imidazole. In some embodiments, $X^1$ cannot be $CR^A$, wherein $R^A$ is halogen (such as F); and $R^{7B}$ cannot be halogen (such as F or Cl). In some embodiments, at least of $R^A$, $R^{7a}$, $R^{7b}$, $R^{7c}$ and $R^{7d}$ is an unsubstituted $C_{1-4}$ haloalkyl, for example, $CF_3$. In some embodiments, at least one of $R^4$ and $R^5$ is halogen. In some embodiments, at least one of $R^4$, $R^5$ and $R^6$ is hydrogen.

Synthesis

Compounds of Formula (I) along with those described herein may be prepared in various ways. General synthetic routes for preparing compounds of Formula (I) are shown and described herein along with some examples of starting materials used to synthesize compounds described herein. The routes shown and described herein are illustrative only and are not intended, nor are they to be construed, to limit the scope of the claims in any manner whatsoever. Those skilled in the art will be able to recognize modifications of the disclosed syntheses and to devise alternate routes based on the disclosures herein; all such modifications and alternate routes are within the scope of the claims.

Scheme 1

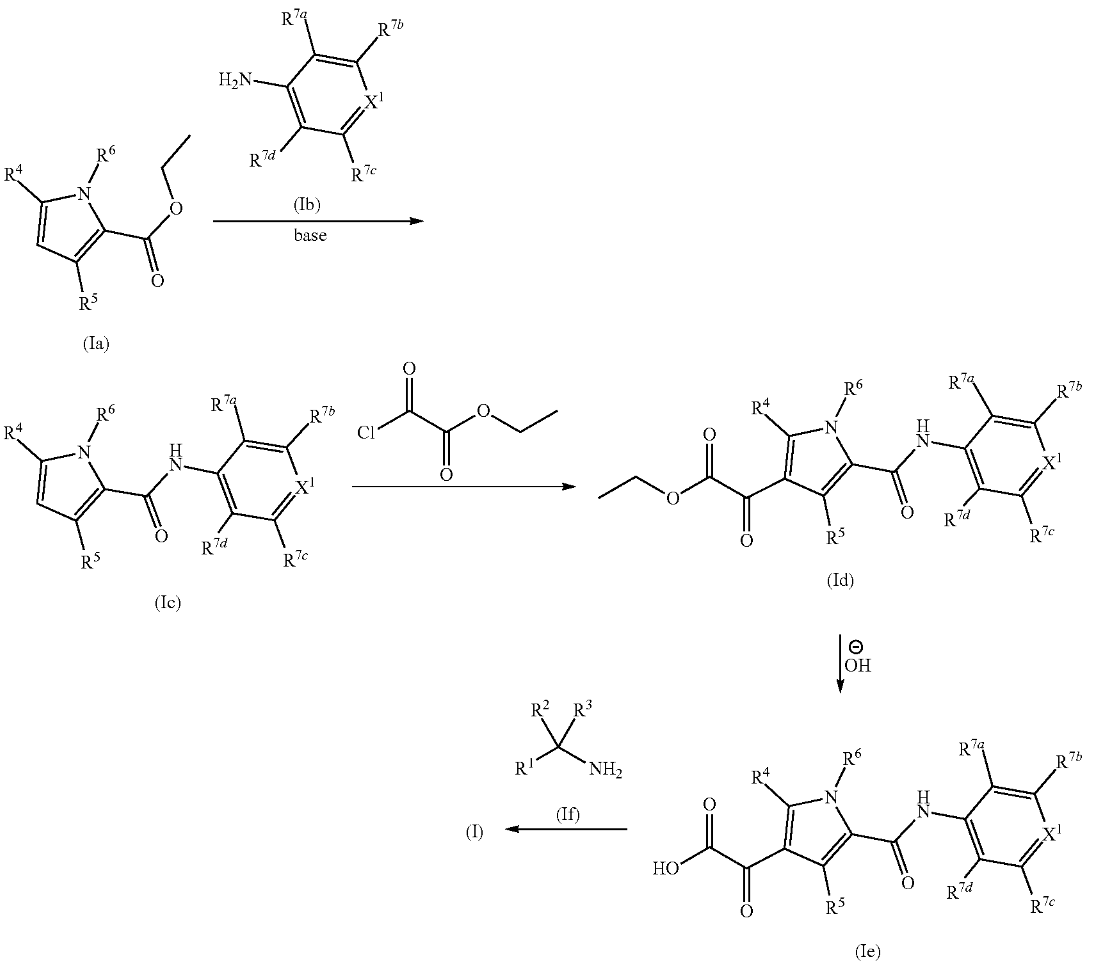

The synthesis of compounds of Formula (I) can be performed as outlined in Scheme 1. An ester of general Formula (Ia) can be coupled with an amine of general Formula (Ib), in presence of a base, for example LiHMDS, in a suitable solvent (such as THF), to give an amide of general Formula (Ic). Reaction of general Formula (Ic) with ethyl 2-chloro-2-oxoacetate in presence of aluminium chloride in a suitable solvent (for example, DCM) can give ketoester of general Formula (Id). General Formula (Id) can subsequently be saponified in basic conditions, using for example lithium hydroxide in a mixture of methanol and water, to give the ketoacid derivative of general Formula (Ie). Coupling of general Formula (Ie) with a substituted amine of general Formula (If) can be performed in the presence of a peptide coupling reagent, for example, HATU or EDCI/HOAT, in the presence of an organic amine base (such as $Et_3N$ or DIPEA), in a suitable solvent (for example DCM), to afford compound of Formula (I), and pharmaceutically acceptable salts thereof.

Pharmaceutical Compositions

Some embodiments described herein relate to a pharmaceutical composition, that can include an effective amount of a compound described herein (e.g., a compound, or a pharmaceutically acceptable salt thereof, as described herein) and a pharmaceutically acceptable carrier, excipient or combination thereof. A pharmaceutical composition described herein is suitable for human and/or veterinary applications.

As used herein, a "carrier" refers to a compound that facilitates the incorporation of a compound into cells or tissues. For example, without limitation, dimethyl sulfoxide (DMSO) is a commonly utilized carrier that facilitates the uptake of many organic compounds into cells or tissues of a subject.

As used herein, a "diluent" refers to an ingredient in a pharmaceutical composition that lacks pharmacological activity but may be pharmaceutically necessary or desirable. For example, a diluent may be used to increase the bulk of a potent drug whose mass is too small for manufacture and/or administration. It may also be a liquid for the dissolution of a drug to be administered by injection, ingestion or inhalation. A common form of diluent in the art is a buffered aqueous solution such as, without limitation, phosphate buffered saline that mimics the composition of human blood.

As used herein, an "excipient" refers to an inert substance that is added to a pharmaceutical composition to provide, without limitation, bulk, consistency, stability, binding ability, lubrication, disintegrating ability etc., to the composition. A "diluent" is a type of excipient.

Proper formulation is dependent upon the route of administration chosen. Techniques for formulation and administration of the compounds described herein are known to those skilled in the art. Multiple techniques of administering a compound exist in the art including, but not limited to, oral, rectal, topical, aerosol, injection and parenteral delivery, including intramuscular, subcutaneous, intravenous, intramedullary injections, intrathecal, direct intraventricular, intraperitoneal, intranasal and intraocular injections. Pharmaceutical compositions will generally be tailored to the specific intended route of administration.

One may also administer the compound in a local rather than systemic manner, for example, via injection of the compound directly into the infected area, often in a depot or sustained release formulation. Furthermore, one may administer the compound in a targeted drug delivery system, for example, in a liposome coated with a tissue-specific antibody. The liposomes may be targeted to and taken up selectively by the organ.

The pharmaceutical compositions disclosed herein may be manufactured in a manner that is itself known, e.g., by means of conventional mixing, dissolving, granulating, dragee-making, levigating, emulsifying, encapsulating, entrapping or tableting processes. As described herein, compounds used in a pharmaceutical composition may be provided as salts with pharmaceutically compatible counterions.

Methods of Use

Some embodiments described herein relate to a method of treating a HBV and/or HDV infection that can include administering to a subject identified as suffering from the HBV and/or HDV infection an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein or a pharmaceutical composition that includes a compound, or a pharmaceutically acceptable salt thereof, as described herein for treating a HBV and/or HDV infection.

Some embodiments disclosed herein relate to a method of treating a HBV and/or HDV infection that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating a HBV and/or HDV infection. Still other embodiments described herein relate to the use of a compound, or a pharmaceutically acceptable salt thereof, as described herein described herein, or a pharmaceutical composition that includes an effective amount of a compound, or a pharmaceutically acceptable salt thereof, as described herein for treating a HBV and/or HDV infection.

Some embodiments disclosed herein relate to a method of inhibiting replication of HBV and/or HDV that can include contacting a cell infected with the HBV and/or HDV with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for inhibiting replication of HBV and/or HDV. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein, for inhibiting replication of HBV and/or HDV.

In some embodiments, the HBV infection can be an acute HBV infection. In some embodiments, the HBV infection can be a chronic HBV infection.

Some embodiments disclosed herein relate to a method of treating liver cirrhosis that is developed because of a HBV and/or HDV infection that can include administering to a subject suffering from liver cirrhosis and/or contacting a cell infected with the HBV and/or HDV in a subject suffering from liver cirrhosis with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cirrhosis with an effective amount of the compound, or a pharmaceutically acceptable salt thereof. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cirrhosis.

Some embodiments disclosed herein relate to a method of treating liver cancer (such as hepatocellular carcinoma) that is developed because of a HBV and/or HDV infection that can include administering to a subject suffering from the liver cancer and/or contacting a cell infected with the HBV and/or HDV in a subject suffering from the liver cancer with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver cancer (such as hepatocellular carcinoma). Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver cancer (such as hepatocellular carcinoma).

Some embodiments disclosed herein relate to a method of treating liver failure that is developed because of a HBV and/or HDV infection that can include administering to a subject suffering from liver failure and/or contacting a cell infected with the HBV and/or HDV in a subject suffering from liver failure with an effective amount of a compound, or a pharmaceutically acceptable salt thereof, as described herein, or a pharmaceutical composition that includes an effective amount of a compound, or a pharmaceutically acceptable salt thereof, as described herein. Other embodiments described herein relate to using a compound, or a pharmaceutically acceptable salt thereof, as described herein in the manufacture of a medicament for treating liver failure. Still other embodiments described herein relate to the use of a compound, or a pharmaceutically acceptable salt thereof, as described herein, or a pharmaceutical composition that includes an effective amount of a compound, or a pharmaceutically acceptable salt thereof, as described herein for treating liver failure.

Various indicators for determining the effectiveness of a method for treating an HBV and/or HDV infection are also known to those skilled in the art. Examples of suitable indicators include, but are not limited to, a reduction in viral load indicated by reduction in HBV DNA (or load) (e.g., reduction<$10^5$ copies/mL in serum), HBV surface antigen (HBsAg) and HBV e-antigen (HBeAg), a reduction in plasma viral load, a reduction in viral replication, a reduction in time to seroconversion (virus undetectable in patient serum), an increase in the rate of sustained viral response to therapy, an improvement in hepatic function, and/or a reduction of morbidity or mortality in clinical outcomes.

As used herein, the terms "treat," "treating," "treatment," "therapeutic," and "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the subject's overall feeling of well-being or appearance.

As used herein, a "subject" refers to an animal that is the object of treatment, observation or experiment. "Animal" includes cold- and warm-blooded vertebrates and invertebrates such as fish, shellfish, reptiles and, in particular, mammals. "Mammal" includes, without limitation, mice, rats, rabbits, guinea pigs, dogs, cats, sheep, goats, cows, horses, primates, such as monkeys, chimpanzees, and apes, and, in particular, humans. In some embodiments, the subject is human.

The term "effective amount" is used to indicate an amount of an active compound, or pharmaceutical agent, that elicits the biological or medicinal response indicated. For example, an effective amount of compound can be the amount needed to alleviate or ameliorate symptoms of disease or prolong the survival of the subject being treated. This response may occur in a tissue, system, animal or human and includes alleviation of the signs or symptoms of the disease being treated. Determination of an effective amount is well within the capability of those skilled in the art, in view of the disclosure provided herein. The effective amount of the compounds disclosed herein required as a dose will depend on the route of administration, the type of animal, including human, being treated, and the physical characteristics of the specific animal under consideration. The dose can be tailored to achieve a desired effect, but will depend on such factors as weight, diet, concurrent medication and other factors which those skilled in the medical arts will recognize.

In some embodiments, an effective amount of a compound, or a pharmaceutically acceptable salt thereof, as described herein is an amount that is effective to achieve a sustained virologic response, for example, a sustained viral response 12 month after completion of treatment.

Subjects who are clinically diagnosed with a HBV and/or HDV infection include "naïve" subjects (e.g., subjects not previously treated for HBV and/or HDV) and subjects who have failed prior treatment for HBV and/or HDV ("treatment failure" subjects). Treatment failure subjects include "non-responders" (subjects who did not achieve sufficient reduction in ALT (alanine aminotransferase) levels, for example, subject who failed to achieve more than 1 log 10 decrease from base-line within 6 months of starting an anti-HBV and/or anti-HDV therapy) and "relapsers" (subjects who were previously treated for HBV and/or HDV whose ALT levels have increased, for example, ALT>twice the upper normal limit and detectable serum HBV DNA by hybridization assays). Further examples of subjects include subjects with a HBV and/or HDV infection who are asymptomatic.

In some embodiments, a compound, or a pharmaceutically acceptable salt thereof, as described herein can be provided to a treatment failure subject suffering from HBV and/or HDV. In some embodiments, a compound, or a pharmaceutically acceptable salt thereof, as described herein can be provided to a non-responder subject suffering from HBV and/or HDV. In some embodiments, a compound, or a pharmaceutically acceptable salt thereof, as described herein can be provided to a relapser subject suffering from HBV and/or HDV. In some embodiments, the subject can have HBeAg positive chronic hepatitis B. In some embodiments, the subject can have HBeAg negative chronic hepatitis B. In some embodiments, the subject can have liver cirrhosis. In some embodiments, the subject can be asymptomatic, for example, the subject can be infected with HBV and/or HDV but does not exhibit any symptoms of the viral infection. In some embodiments, the subject can be immunocompromised. In some embodiments, the subject can be undergoing chemotherapy.

Examples of agents that have been used to treat HBV and/or HDV include immunomodulating agents, and nucleosides/nucleotides. Examples of immunomodulating agents include interferons (such as IFN-α and pegylated interferons that include PEG-IFN-α-2a); and examples of nucleosides/nucleotides include lamivudine, telbivudine, adefovir dipivoxil, clevudine, entecavir, tenofovir alafenamide and tenofovir disoproxil. However, some of the drawbacks associated with interferon treatment are the adverse side effects, the need for subcutaneous administration and high cost. Potential advantages of a compound of Formula (I), or a pharmaceutically acceptable salt of any of the foregoing, can be less adverse side effects, delay in the onset of an adverse side effect and/or reduction in the severity of an adverse side effect. A drawback with nucleoside/nucleotide treatment can be the development of resistance, including cross-resistance.

Resistance can be a cause for treatment failure. The term "resistance" as used herein refers to a viral strain displaying a delayed, lessened and/or null response to an anti-viral agent. In some embodiments, a compound, or a pharmaceutically acceptable salt thereof, as described herein can be provided to a subject infected with an HBV and/or HDV strain that is resistant to one or more anti-HBV and/or anti-HDV agents. Examples of anti-viral agents wherein resistance can develop include lamivudine, telbivudine, adefovir dipivoxil, clevudine, entecavir, tenofovir alafenamide and tenofovir disoproxil. In some embodiments, development of resistant HBV and/or HDV strains is delayed when a subject is treated with a compound, or a pharmaceutically acceptable salt thereof, as described herein compared to the development of HBV and/or HDV strains resistant to other HBV and/or HDV anti-viral agents, such as those described.

Previously known compounds, such as those provided in WO 2017/156255, were shown to form adducts with glutathione in in vitro assays. Formation of glutathione adducts can be a signal that a compound has the potential to induce liver injury. Thus, the formation of glutathione adducts can be used as a signal to predict safety. Unexpectedly, compounds described herein, such as many compounds of Formula (I), and pharmaceutically acceptable salts thereof, have been shown not to form adducts with glutathione in in vitro assays. Further, known compounds (for example, those described in WO 2017/156255), have demonstrated potency in a HepG2.2.15 cell based assay with an $EC_{50}$ of >1000 pM. Many compounds described herein, such as compounds of Formula (I), and pharmaceutically acceptable salts thereof, unexpectedly show improved potency in a HepG2.2.15 cell based assay with an $EC_{50}$<1000 pM range. Thus, compounds described herein, including compounds of Formula (I), and pharmaceutically acceptable salts thereof, can be at least 16 times more potent than previously known compounds. In some embodiments, improved potency can lead to a significantly lower dose requirement and therefore improve daily dose burden as well as lead to improved safety margins.

Combination Therapies

In some embodiments, a compound, or a pharmaceutically acceptable salt thereof, as described herein can be used in combination with one or more additional agent(s) for treating and/or inhibiting replication HBV and/or HDV. Additional agents include, but are not limited to, an interferon, nucleoside/nucleotide analogs, a sequence specific oligonucleotide (such as anti-sense oligonucleotide and siRNA), nucleic acid polymers (NAPs, such as nucleic acid polymers that reduce HBsAg levels) an entry inhibitor and/or a small molecule immunomodulator. Examples of additional agents include recombinant interferon alpha 2b, IFN-α, PEG-IFN-α-2a, lamivudine, telbivudine, adefovir dipivoxil, clevudine, entecavir, tenofovir alafenamide and tenofovir disoproxil. Examples of NAPs include, but are not limited to, REP 2139, REP 2165 and those described in U.S. Application No. 62/757,632, filed Nov. 8, 2018, which is hereby incorporated by reference for the purpose of the NAPs described therein.

In some embodiments, a compound, or a pharmaceutically acceptable salt thereof, as described herein can be administered with one or more additional agent(s) together in a single pharmaceutical composition. In some embodiments, a compound, or a pharmaceutically acceptable salt thereof, can be administered with one or more additional agent(s) as two or more separate pharmaceutical compositions. Further, the order of administration of a compound, or a pharmaceutically acceptable salt thereof, as described herein with one or more additional agent(s) can vary.

EXAMPLES

Additional embodiments are disclosed in further detail in the following examples, which are not in any way intended to limit the scope of the claims.

Example 1

Compound A

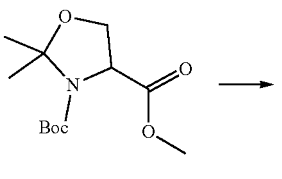

-continued

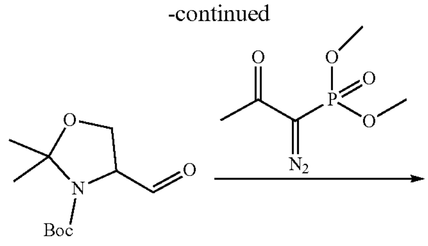

A1

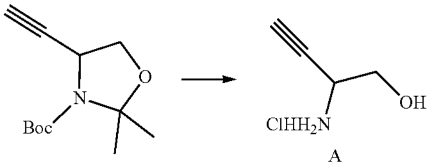

A2

A

A 250-mL 3-necked round-bottom flask purged and maintained with an inert atmosphere of $N_2$ was charged with 3-tert-butyl 4-methyl 2,2-dimethyl-1,3-oxazolidine-3,4-dicarboxylate (5.00 g, 19.3 mmol, 1.00 eq.), toluene (50 mL). Diisobutylaluminium hydride (38.6 mL, 38.6 mmol, 2.00 eq., 1M in toluene) was slowly added at −78° C. The rate of addition was adjusted so as to keep the internal temperature below −65° C. The resulting solution was stirred for 2 h at −78° C., and the reaction quenched by slowly adding cold $CH_3OH$ (10 mL). The mixture was slowly poured into ice-cold 1M HCl (100 mL), and the mixture was extracted with ethyl acetate (3×100 mL). The combined organic layer was washed with brine, dried over anhydrous sodium sulfate and concentrated under vacuum to afford tert-butyl 4-formyl-2,2-dimethyl-1,3-oxazolidine-3-carboxylate (4.20 g, crude) of as a colorless oil.

A 40-mL vial was charged with tert-butyl 4-formyl-2,2-dimethyl-1,3-oxazolidine-3-carboxylate (4.20 g, 18.3 mmol, 1.00 eq.), dimethyl (1-diazo-2-oxopropyl)phosphonate (4.22 g, 22.0 mmol, 1.20 eq.), $K_2CO_3$ (5.06 g, 36.6 mmol, 2.00 eq.) and methanol (20 mL). The resulting solution was stirred for overnight at room temperature (rt). The reaction was quenched by water (20 mL) and diluted with ethyl acetate (3×20 mL). The mixture was washed with brine (20 mL) and water (20 mL), dried over anhydrous sodium sulfate, filtered and concentrated under reduced pressure. The residue was chromatographed on a silica gel column with ethyl acetate (EA):petroleum ether (PE) (1:10) to provide 3.20 g (70% yield) of tert-butyl 4-ethynyl-2,2-dimethyl-1,3-oxazolidine-3-carboxylate as a yellow oil.

A solution of tert-butyl 4-ethynyl-2,2-dimethyl-1,3-oxazolidine-3-carboxylate (1.00 g, 4.44 mmol), 4M hydrochloric acid in 1,4-dioxane (5 mL) and ethanol (10 mL) was stirred overnight at 60° C. The mixture was concentrated under reduced pressure to provide 2-aminobut-3-yn-1-ol hydrochloride (538 mg, crude) as a yellow solid. $^1H$ NMR (300 MHz, Methanol-$d_4$) δ 4.14 (br, 1H), 3.89 (dd, J=11.6, 4.2 Hz, 1H), 3.75-3.68 (m, 1H), 3.25 (d, J=2.4 Hz, 1H). LCMS (ES) m/z=86 (M+H−HCl)$^+$.

Example 2

Compound B

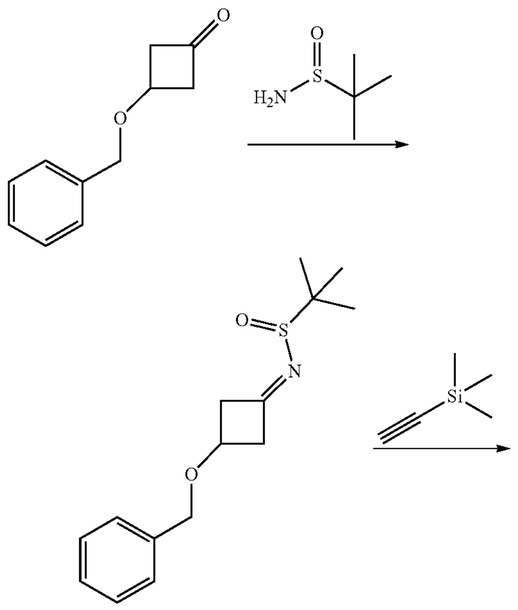

B1

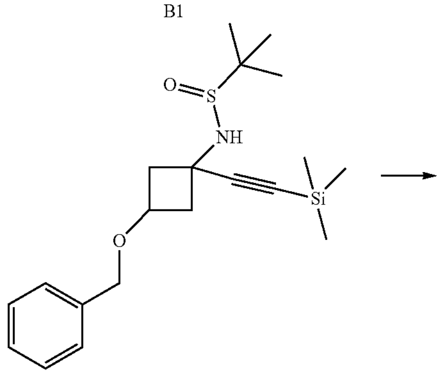

B2

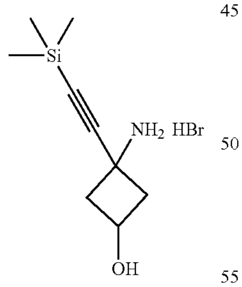

B

The mixture of 3-(benzyloxy)cyclobutan-1-one (5.00 g, 28.4 mmol, 1.00 eq.), titanium isopropylate (8.80 g, 30.9 mmol, 1.09 eq.), tert-butanesulfinamide (3.70 g, 30.5 mmol, 1.08 eq.) and dichloromethane (50 mL) was stirred overnight at 45° C. The mixture was cooled to rt. Sat. sodium bicarbonate solution (5 mL) was added. The mixture was stirred 30 min, and the solids were filtered off. The filtrate was concentrated under reduced pressure. The residue was purified by silica gel column chromatography, eluted with EA:PE (1:10) to afford N-[3-(benzyloxy)cyclobutylidene]-2-methylpropane-2-sulfinamide (4.50 g, 57% yield) as a light yellow oil.

To a stirred mixture of trimethylsilylacetylene (4.70 g, 47.8 mmol, 2.97 eq.) in diethyl ether (100 mL) was added n-BuLi (13.0 mL, 32.5 mmol, 2.02 eq., 2.5 M in hexane) dropwise −78° C. under $N_2$ atmosphere. The mixture was stirred for 1 h at −78° C. N-[3-(benzyloxy)cyclobutylidene]-2-methylpropane-2-sulfinamide (4.50 g, 16.1 mmol, 1.00 eq.) in $Et_2O$ (10 mL) was added dropwise at −78° C. The mixture was stirred for 2 h at −78° C. The reaction was quenched by water (100 mL). The mixture was extracted with EA (3×100 mL). The organic layers were combined, dried over with anhydrous sodium sulfate, filtered and concentrated under reduced pressure. The residue was purified by Prep-TLC (EA:PE=1:3) to afford N-[3-(benzyloxy)-1-[2-(trimethylsilyl)ethynyl]cyclobutyl]-2-methylpropane-2-sulfinamide (950 mg, 16% yield) as a colorless oil.

To a stirred mixture of N-[3-(benzyloxy)-1-[2-(trimethylsilyl)ethynyl]cyclobutyl]-2-methylpropane-2-sulfinamide (300 mg, 0.800 mmol, 1.00 eq.) in chloromethane (5 mL) was added $BBr_3$ (3.00 mL, 3.00 mmol, 3.70 eq., 1 M in DCM) at rt. The mixture was stirred for 2 h at rt. Water (0.1 ml) was added to the mixture and stirred for 0.5 h. The solids were filtered off. The filtrate was concentrated under reduced pressure to afford 3-amino-3-((trimethylsilyl)ethynyl)cyclobutan-1-ol hydrobromide salt (130 mg, 62% yield) as a light yellow solid. $^1H$ NMR (400 MHz, Methanol-$d_4$) δ 4.42-4.31 (m, 1H), 2.83 (ddt, J=9.1, 7.0, 2.5 Hz, 2H), 2.37 (ddt, J=11.6, 7.6, 2.2 Hz, 2H), 0.22 (s, 9H). LCMS (ESI, m/z): 184 $[M+H-HBr]^+$.

Example 3

Compound C

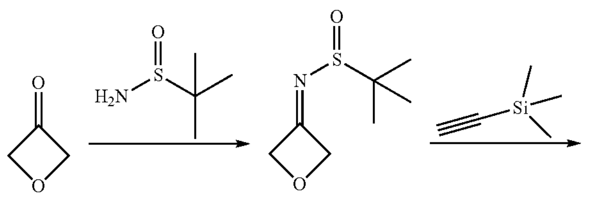

C1

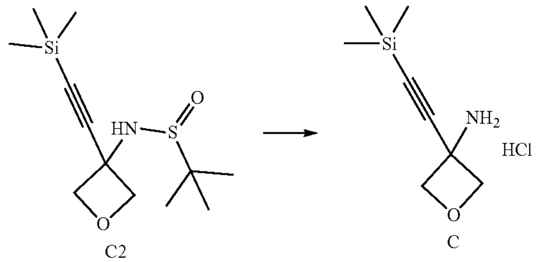

C2

C

The mixture of 3-oxetanone (5.00 g, 69.4 mmol, 1.00 eq.), tert-butanesulfinamide (9.20 g, 75.9 mmol, 1.10 eq.), titanium isopropylate (21.6 g, 76.0 mmol, 1.10 eq.) and dichloromethane (50.00 mL) was stirred overnight at 45° C. The reaction was cooled to rt and quenched with sat. sodium bicarbonate solution (5.0 mL). The mixture was stirred 30 min, and the solids were filtered off. The filtrate was concentrated under reduced pressure. The residue was purified by silica gel column chromatography, eluted with EA:PE (1:10) to afford 2-methyl-N-(oxetan-3-ylidene)propane-2-sulfinamide (5.00 g, 39% yield) as a light yellow oil. LCMS (ESI, m/z): 176 $[M+H]^+$.

To a stirred mixture of trimethylsilylacetylene (8.40 g, 85.5 mmol, 3.00 eq.) in THF (50.00 mL) was added n-BuLi (30.0 mL, 2.5 M in hexane, 75.0 mmol, 2.63 eq.) dropwise at −78° C. under atmosphere. The mixture was stirred for 1 h at −78° C. The mixture of 2-methyl-N-(oxetan-3-ylidene)propane-2-sulfinamide (5.00 g, 28.5 mmol, 1.00 eq.) in THF (10 mL) was added dropwise at −78° C. The reaction was stirred for 2 h at −78° C., and then quenched by water (100 mL). The mixture was extracted with EA (3×100 mL). The organic phase was washed with water, dried with anhydrous sodium sulfate, filtered and concentrated under reduced pressure. The residue was purified by silica gel column chromatography, eluted with EA:PE (1:10) to afford 2-methyl-N-[3-[2-(trimethylsilyl)ethynyl]oxetan-3-yl]propane-2-sulfinamide (7.00 g, 88% yield) as a yellow solid. LCMS (ESI, m/z): 274 $[M+H]^+$.

Hydrochloric acid (7.5 mL, 30.0 mmol, 2.05 eq., 4 M in 1,4-dioxane) was added to the mixture of 2-methyl-N-[3-[2-(trimethylsilyl)ethynyl]oxetan-3-yl]propane-2-sulfinamide (4.00 g, 14.6 mmol, 1.00 eq.) and 1,4-dioxane (50 mL). The mixture was stirred for 2 h at rt. The solid was collected by filtration, washed with PE and dried to afford 3-[2-(trimethylsilyl)ethynyl]oxetan-3-amine hydrochloride (2.70 g, 89% yield) as a light yellow solid. LCMS (ESI, m/z): 170 $[M+H-HCl]^+$.

Example 4

Compound D

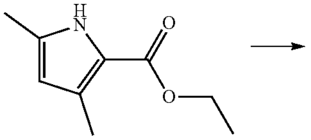

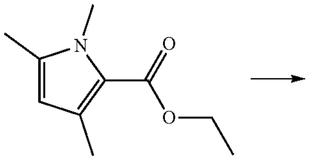

D1

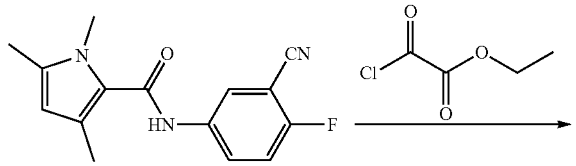

D2

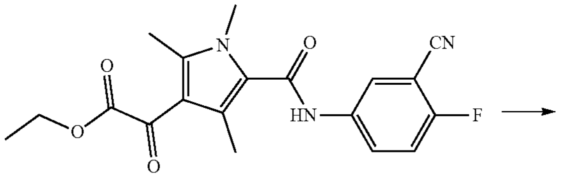

D3

-continued

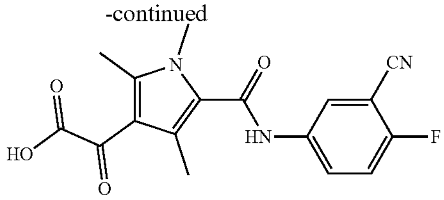

D

A 250 mL round bottom flask was charged with ethyl 3,5-dimethyl-1H-pyrrole-2-carboxylate (10.0 g, 59.8 mmol, 1.00 eq.) and dimethylsulfoxide (100 mL). KOH (5.03 g, 89.7 mmol, 1.50 eq.) was added in portions at 0° C. The mixture was stirred 30 min at rt. Methyl iodide (10.2 g, 71.8 mmol, 1.20 eq.) was added dropwise at rt. The resulting solution was stirred for 4 h at rt. The reaction was quenched by water (100 mL) and diluted with EA (500 mL). The mixture was washed with brine (200 mL) and water (5×100 mL), dried over anhydrous sodium sulfate, filtered and concentrated under reduced pressure to provide ethyl 1,3,5-trimethyl-1H-pyrrole-2-carboxylate (10.1 g, 92% yield) as a white solid. LCMS (ESI, m/z): 182 $[M+H]^+$.

A 100-mL three-necked round-bottom flask was placed ethyl 1,3,5-trimethylpyrrole-2-carboxylate (2.00 g, 11.0 mmol, 1.00 eq.), 5-amino-2-fluorobenzonitrile (3.00 g, 22.1 mmol, 2.00 eq.) and tetrahydrofuran (20 mL) under $N_2$. Lithium hexamethyldisilazide (33.0 mL, 33.0 mmol, 3.00 eq., 1M in THF) was added dropwise to above mixture at 0° C. The resulting solution was stirred overnight at rt, and the reaction quenched with a sat. ammonium chloride solution (50 mL). The mixture was extracted with EA (3×50 mL). The organic layers were combined, dried over anhydrous sodium sulfate and concentrated under vacuum. The residue was purified by trituration with EA:hexane (1:1), and the solid was collected by filtration and dried to afford N-(3-cyano-4-fluorophenyl)-1,3,5-trimethylpyrrole-2-carboxamide (2.50 g, 75% yield) as a white solid. LCMS (ESI, m/z): 272 $[M+H]^+$.

Into a 50-mL 3-necked round-bottom flask was placed ethyl 1,3,5-trimethyl-1H-pyrrole-2-carboxylate (2.50 g, 13.8 mmol, 1.00 eq.) and dichloromethane (100 mL). Ethyl oxalochloridate (2.82 g, 20.0 mmol, 1.50 eq.) in dichloromethane (20 mL) was added dropwise to the mixture at 0° C. Aluminium chloride (4.23 g, 31.7 mmol, 2.50 eq.) was added in portions at 0° C. The solution was stirred overnight at rt, and the reaction was quenched with water/ice. The solution was extracted dichloromethane (3×100 mL). The organic layers were combined, washed with sat. sodium bicarbonate solution (100 mL) and water (100 mL). The mixture was dried over anhydrous sodium sulfate and concentrated under vacuum. The residue was purified by trituration with EA:hexane (1:1), and the solid was collected by filtration and dried to afford ethyl 4-(2-ethoxy-2-oxoacetyl)-1,3,5-trimethyl-1H-pyrrole-2-carboxylate (2.00 g, 56% yield) as a white solid. LCMS (ESI, m/z): 372 $[M+H]^+$.

A 50 mL round bottom flask was charged with ethyl 4-(2-ethoxy-2-oxoacetyl)-1,3,5-trimethyl-1H-pyrrole-2-carboxylate (2.00 g, 5.39 mmol, 1.00 eq.), lithium hydroxide (21.6 mg, 10.8 mmol, 2.00 eq.), methanol (50 mL) and water (10 mL). The resulting solution was stirred overnight at rt. The methanol was removed under reduced pressure. The residue was dissolved with water (50 mL) and extracted by EA (3×20 mL). The pH value of the water layer was adjusted to 3 with hydrochloric acid (1 mol/L). The mixture was extracted EA (3×50 mL). The organic layers were combined, dried over anhydrous sulfate, filtered and concentrated under reduced pressure to provided desired product 2-(5-((3-cyano-4-fluorophenyl)carbamoyl)-1,2,4-trimethyl-1H-pyrrol-3-yl)-2-oxoacetic acid (1.50 g, 81% yield) as white solid. LCMS (ESI, m/z): 344 $[M+H]^+$.

Example 5

Compound E

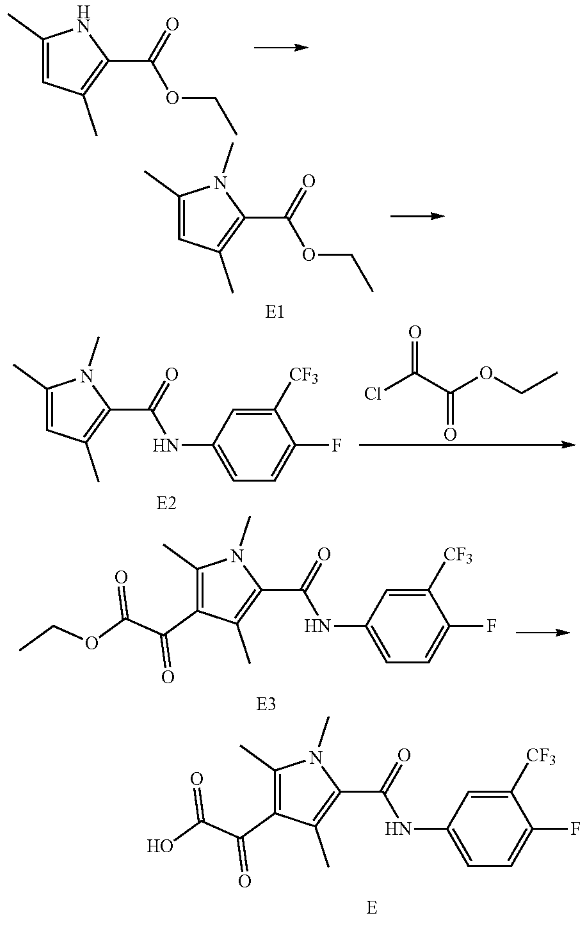
E1
E2
E3
E

A 250 mL round bottom flask was charged with ethyl 3,5-dimethyl-1H-pyrrole-2-carboxylate (10.0 g, 59.8 mmol, 1.00 eq.) and dimethylsulfoxide (100 mL). KOH (5.03 g, 89.7 mmol, 1.50 eq.) was added in portions at 0° C. The mixture was stirred 30 min at rt. Methyl iodide (10.2 g, 71.8 mmol, 1.20 eq.) was added dropwise to above mixture at rt. The resulting solution was stirred for 4 h at rt. The reaction was quenched by water (100 mL) and diluted with EA500 mL). The mixture was washed with brine (200 mL) and water (5×100 mL), dried over anhydrous sodium sulfate, filtered and concentrated under reduced pressure to provide ethyl 1,3,5-trimethyl-1H-pyrrole-2-carboxylate (10.1 g, 92% yield) as a white solid. LCMS (ESI, m/z): 182 $[M+H]^+$.

Into a 250-mL round-bottom flask purged and maintained with an inert atmosphere of $N_2$, was placed ethyl 1,3,5-trimethylpyrrole-2-carboxylate (5.00 g, 27.6 mmol, 1.00 eq.), 4-fluoro-3-(trifluoromethyl)aniline (7.40 g, 41.3 mmol, 1.50 eq.) and tetrahydrofuran (50.00 mL). LiHMDS (80.0 mL, 80.0 mmol, 2.90 eq., 1 mol/L in THF) was added dropwise to the mixture at 0° C. The resulting solution was stirred overnight at rt, and the reaction was quenched with a sat. ammonium chloride solution (100 mL). The solution was extracted with EA (3×100 mL). The organic layers were combined, dried over anhydrous sodium sulfate, filtered and concentrated under vacuum. The residue was purified by trituration with EA:hexane (1:1). The solids were collected by filtration and dried to provide N-[4-fluoro-3-(trifluoromethyl)phenyl]-1,3,5-trimethylpyrrole-2-carboxamide (9.00 g, 93% yield) as a white solid. LCMS (ESI, m/z): 315 $[M+H]^+$.

Into a 250-mL 3-necked round-bottom flask purged and maintained with an inert atmosphere of $N_2$, was placed N-[4-fluoro-3-(trifluoromethyl)phenyl]-1,3,5-trimethylpyrrole-2-carboxamide (3.00 g, 9.55 mmol, 1.00 eq.) and dichloromethane (100 mL). A solution of ethyl chloroglyoxylate (1.56 g, 11.5 mmol, 1.20 eq.) in dichloromethane (20 mL) was added dropwise to the mixture at 0° C. Aluminium chloride (1.90 g, 14.3 mmol, 1.50 eq.) was added to above mixture in portions at 0° C. The resulting solution was stirred overnight at rt, and the reaction quenched by ice/water (100 mL). The mixture was extracted with dichloromethane (3×100 mL). The organic layers were combined, washed with sat. sodium bicarbonate solution (100 mL) and water (100 mL), dried over anhydrous sodium, filtered and concentrated under reduced pressure. The residue was purified by silica gel column chromatography, eluted with EA:PE (1:2) to afford ethyl 2-(5-[[4-fluoro-3-(trifluoromethyl)phenyl]carbamoyl]-1,2,4-trimethylpyrrol-3-yl)-2-oxoacetate (2.00 g, 48% yield) as a white solid. LCMS (ESI, m/z): 415 $[M+H]^+$.

A 100 mL round bottom flask was charged with ethyl 2-(5-[[4-fluoro-3-(trifluoromethyl)phenyl]carbamoyl]-1,2,4-trimethylpyrrol-3-yl)-2-oxoacetate (2.00 g, 4.83 mmol, 1.00 eq.), LiOH (0.231 g, 9.65 mmol, 2.00 eq.), methanol (50.00 mL) and water (10.00 mL). The resulting solution was stirred overnight at rt and diluted with water (100 mL). The pH value of the mixture was adjusted to 3 with hydrochloric acid (1 mol/L). The mixture was extracted with EA (3×100 mL). The organic layers was combined, dried over anhydrous sodium sulfate, filtered and concentrated under reduced pressure to provide (5-[[4-fluoro-3-(trifluoromethyl)phenyl]carbamoyl]-1,2,4-trimethylpyrrol-3-yl)(oxo)acetic acid (1.85 g, 94% yield) as a white solid. LCMS (ESI, m/z): 387 $[M+H]^+$.

Example 6

Compound 26

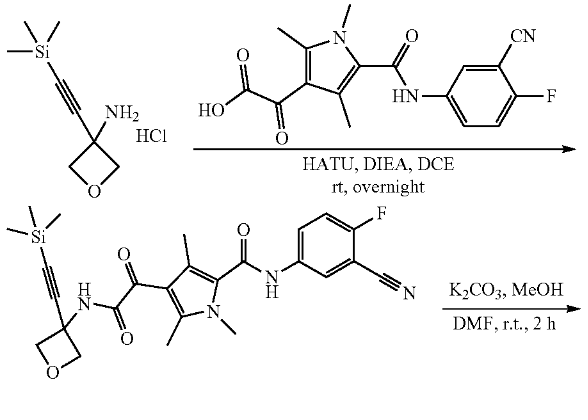

-continued

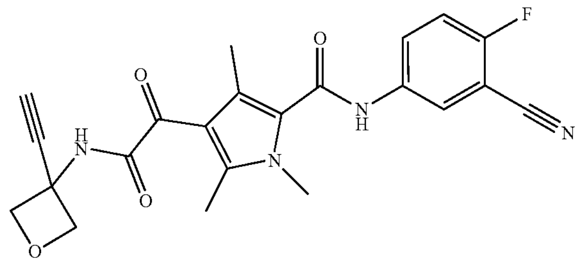

26

A mixture compound D (1.00 g, 2.91 mmol, 1.00 eq.), HATU (3.30 g, 8.68 mmol, 2.98 eq.), 1,2-dichloromethane (50 mL), N,N-diisopropylethylamine (1.50 mL, 8.61 mmol, 2.96 eq.) and compound C (0.900 g, 4.37 mmol, 1.50 eq.) was stirred overnight at rt. The reaction was quenched by water (200 mL). The mixture was extracted with dichloromethane (3×200 mL). The combined organic layers were washed with water (100 mL), dried over anhydrous sodium sulfate, filtered and concentrated under reduced pressure. The residue was purified by trituration with EA (50 mL), and the solid was collected by filtration and dried to afford N-(3-cyano-4-fluorophenyl)-1,3,5-trimethyl-4-[([3-[2-(trimethylsilyl)ethynyl]oxetan-3-yl]carbamoyl)carbonyl] pyrrole-2-carboxamide (1.30 g, 90% yield) as a white solid. LCMS (ESI, m/z): 495 $[M+H]^+$.

The mixture of N-(3-cyano-4-fluorophenyl)-1,3,5-trimethyl-4-[([3-[2-(trimethylsilyl)ethynyl]oxetan-3-yl]carbamoyl)carbonyl]pyrrole-2-carboxamide (1.30 g, 2.63 mmol, 1.00 eq.), potassium carbonate (1.10 g, 7.89 mmol, 3.00 eq.), methanol (5 mL) and N,N-dimethylformamide (20 mL) was stirred for 2 h at rt. The solids were filtrated off. The filtrate was concentrated under reduced pressure. The residue was trituration by water (100 mL), and the solid was collected by filtration and dried to afford N-(3-cyano-4-fluorophenyl)-4-[[(3-ethynyloxetan-3-yl)carbamoyl]carbonyl]-1,3,5-trimethylpyrrole-2-carboxamide (compound 26) (784.8 mg, 68% yield) as an off-white solid. $^1H$ NMR (400 MHz, DMSO-$d_6$) δ 10.53 (s, 1H), 9.75 (s, 1H), 8.20 (dd, J=5.8, 2.7 Hz, 1H), 7.95 (ddd, J=8.0, 4.7, 2.6 Hz, 1H), 7.53 (t, J=9.1 Hz, 1H), 4.72 (d, J=6.6 Hz, 4H), 3.65 (s, 1H), 3.59 (s, 3H), 2.41 (s, 3H), 2.25 (s, 3H). LCMS (ESI, m/z): 423 $[M+H]^+$.

Example 7

Compounds 31a and 31b

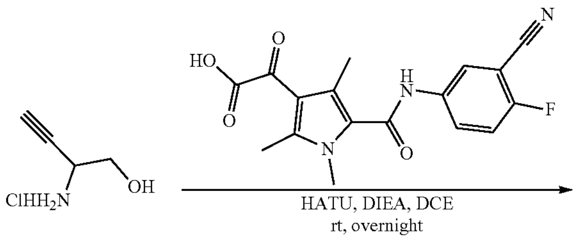

-continued

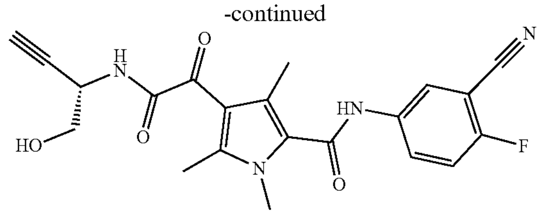

31b

+

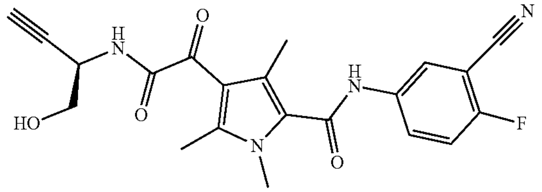

31a

A 40 mL vial was charged with Compound A (240 mg, 1.97 mmol, 1.00 eq.), 1,2-dichloroethane (10 mL), Compound D (678 mg, 1.97 mmol, 1.00 eq.), 1-[Bis(dimethylamino)methylene]-1H-1,2,3-triazolo[4,5-b]pyridinium 3-oxide hexafluorophosphate (751 mg, 1.97 mmol, 1.00 eq.) and N,N-diisopropylethylamine (766 mg, 5.92 mmol, 3.00 eq.). The resulting solution was stirred overnight at rt, and the reaction was quenched by water (10 mL). The mixture was extracted with EA (3×10 mL). The organic layers were combined, washed with brine (3×10 mL), dried over anhydrous sodium sulfate, filtered and concentrated under reduced pressure. The product mixture (360 mg) was separated by pre-Chiral-HPLC (Column: CHIRALPAK IG, 20*250 mm, 5 um; Mobile Phase A: Hex (8 mmol/L $NH_3$·MeOH)—HPLC, Mobile Phase B: EtOH—HPLC; Flow rate: 18 mL/min; Gradient: 50 B to 50 B in 22 min; 254/220 nm; RT1:12.491; RT2:17.162). The appropriate fractions were identified by UV absorbance (254 nm) to obtain pure the first eluting isomer N-(3-cyano-4-fluorophenyl)-4-([[(2S)-1-hydroxybut-3-yn-2-yl]carbamoyl]carbonyl)-1,3,5-trimethylpyrrole-2-carboxamide (125.6 mg, 0.306 mmol) as a white solid. LCMS (ES) m/z=411 $(M+H)^+$. $^1H$ NMR (300 MHz, DMSO-$d_6$) δ 10.52 (s, 1H), 9.05 (d, J=8.2 Hz, 1H), 8.19 (dd, J=5.8, 2.7 Hz, 1H), 7.92-7.98 (m, 1H), 7.53 (t, J=9.2 Hz, 1H), 5.13 (t, J=5.9 Hz, 1H), 4.58-4.65 (m, 1H), 3.66-3.46 (m, 5H), 3.22 (d, J=2.3 Hz, 1H), 2.39 (s, 3H), 2.24 (s, 3H).

The second eluting isomer N-(3-cyano-4-fluorophenyl)-4-([[(2R)-1-hydroxybut-3-yn-2-yl]carbamoyl]carbonyl)-1,3,5-trimethylpyrrole-2-carboxamide (133.5 mg, 0.326 mmol) as a white solid. LCMS (ES) m/z=411 (M+H)+. $^1H$ NMR (300 MHz, DMSO-$d_6$) δ 10.52 (d, J=3.5 Hz, 1H), 9.07 (d, J=8.2 Hz, 1H), 8.28-8.11 (m, 1H), 7.92-7.98 (m, 1H), 7.60-7.45 (m, 1H), 5.14 (s, 1H), 4.61 (s, 1H), 3.57 (s, 5H), 3.21-3.23 (m, 1H), 2.39 (d, J=4.0 Hz, 3H), 2.24 (d, J=4.1 Hz, 3H).

Example 8

Compound 32

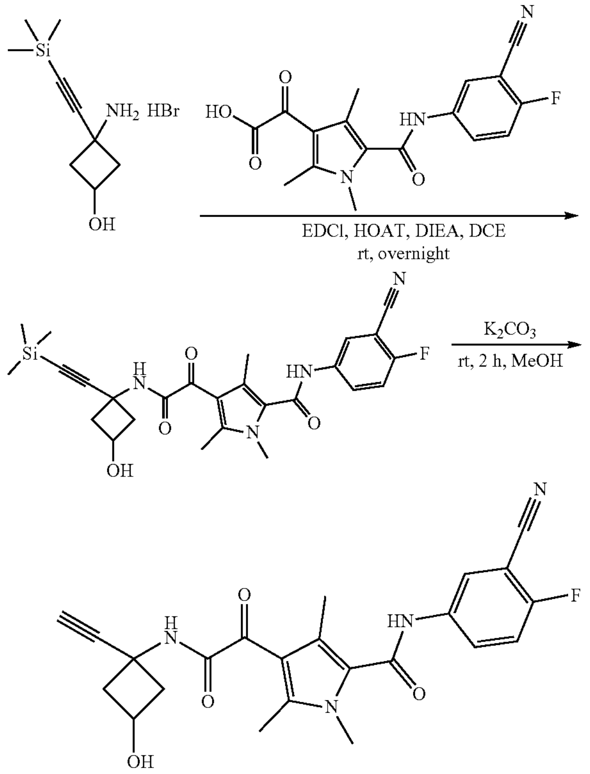

32

The mixture of Compound B (200 mg, 1.10 mmol, 1.00 eq.), Compound D (250 mg, 0.700 mmol, 0.67 eq.), ethyl-3-(3-dimethylaminopropyl)carbodiimide hydrochloride (320 mg, 1.70 mmol, 1.50 eq.), 1-hydroxy-7-azabenzotriazole (220 mg, 1.60 mmol, 1.50 eq.), N,N-diisopropylethylamine (220 mg, 1.70 mmol, 1.56 eq.) and 1,2-dichloroethane (10 mL) was stirred overnight at rt and concentrated in reduced pressure. The residue was dissolved in EA (50 mL) and washed with water (3x20 mL). The organic phase was dried over anhydrous sodium sulfate and concentrated under reduced pressure. The residue was purified by Prep-TLC (EA:PE=2:1) to afford N-(3-cyano-4-fluorophenyl)-4-[([3-hydroxy-1-[2-(trimethylsilyl)ethynyl]cyclobutyl]carbamoyl)carbonyl]-1,3,5-trimethylpyrrole-2-carboxamide (170 mg, 46% yield) as a yellow solid. $^1H$ NMR (400 MHz, DMSO-$d_6$) δ 10.55 (s, 1H), 9.29 (s, 1H), 8.22 (dd, J=5.8, 2.7 Hz, 1H), 7.98 (ddd, J=9.3, 4.9, 2.7 Hz, 1H), 7.56 (t, J=9.1 Hz, 1H), 5.33 (d, J=6.7 Hz, 1H), 4.14 (q, J=7.2 Hz, 1H), 3.60 (s, 3H), 2.77 (ddd, J=9.5, 6.9, 3.0 Hz, 2H), 2.43 (s, 3H), 2.28 (s, 3H), 2.22-2.10 (m, 2H), 0.14 (s, 9H). LCMS (ESI, m/z): 509 $[M+H]^+$.

The mixture of N-(3-cyano-4-fluorophenyl)-4-[([3-hydroxy-1-[2-(trimethylsilyl)ethynyl]cyclobutyl]carbamoyl)carbonyl]-1,3,5-trimethylpyrrole-2-carboxamide (170 mg, 0.30 mmol, 1.00 eq.), methanol (5 mL) and potassium carbonate (150 mg, 1.10 mmol, 3.22 eq.) was stirred for 2 h at rt. The solids were filtered off. The filtrate was concentrated under reduced pressure. The residue was purified by preparative HPLC using the following gradient conditions: Column: XBridge $C_{18}$ OBD Prep Column, 19 mm×250 mm; Mobile Phase A: Water (0.05% TFA), Mobile Phase B: THF—HPLC; Flow rate: 25 mL/min; Gradient: 25% to 55% in 7 min; 220 nm. Purification resulted in N-(3-cyano-4-fluorophenyl)-4-[[(1-ethynyl-3-hydroxycyclobutyl)carbamoyl]carbonyl]-1,3,5-trimethylpyrrole-2-carboxamide (26.1 mg, 18% yield) as a yellow solid. $^1H$ NMR (300 MHz, DMSO-$d_6$) δ 10.50 (s, 1H), 9.26 (s, 1H), 8.20 (dd, J=5.8, 2.7 Hz, 1H), 8.03-7.91 (m, 1H), 7.53 (t, J=9.2 Hz, 1H), 5.30 (d, J=6.7 Hz, 1H), 4.15 (q, J=7.3 Hz, 1H), 3.60 (s, 3H), 3.22 (s, 1H), 2.83-2.71 (m, 2H), 2.42 (s, 3H), 2.27 (s, 3H), 2.17 (t, J=10.1 Hz, 2H). LCMS (ESI, m/z): 437 $[M+H]^+$.

Example 9

Compound 54

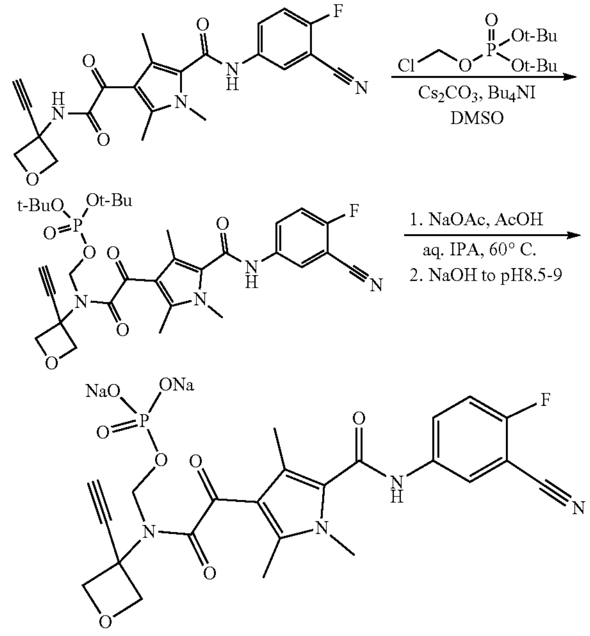

54

Cesium carbonate (9.78 g, 30 mmol, 3 eq.) was added to a stirred solution of Compound 26 (4.22 g, 10 mmol), di-tert-butyl chloromethyl phosphate (3.89 g, 15 mmol, 1.5 eq.) and tetrabutylammonium iodide (738 mg, 2 mmol, 0.2 eq.) in anhydrous DMSO (40 mL). The mixture stirred overnight at rt and then partitioned between water and ethyl acetate. The organic phase was separated and washed with diluted brine (2×). The aqueous phases were back-extracted with ethyl acetate. The combined organic solution was dried over sodium sulfate and concentrated under reduced pressure to a give a yellow-beige foam (9 g). The residue was purified by column chromatography in 40 to 100% ethyl acetate-hexane to give the bis-tert-butyl phosphate intermediate (1.72 g, 27%).

To solution of the bis-tert-butyl phosphate intermediate from previous step (1.7 g, 2.6 mmol) in IPA (10 mL) were added 0.2M aq. sodium acetate solution (6 mL, 1.2 mmol, 0.46 eq.) and 0.2M aqueous acetic acid (2 mL, 0.4 mmol, 0.15 eq.). The mixture was heated at 55-60° C. for 3 h. After cooling to rt, the mixture was made basic (pH 8.5) with 2N aq. NaOH (3.1 mL, 6.2 mmol). The resulting solution was concentrated under reduced pressure to ~8 mL. Some precipitate was filtered-off and discarded. The filtrate was diluted with acetone (40 mL), and resulting mixture was kept overnight at 4° C. A fine crystalline solid formed and was collected by filtration, rinsed with acetone and dried under vacuum to provide sodium (2-(5-((3-cyano-4-fluorophenyl)carbamoyl)-1,2,4-trimethyl-1H-pyrrol-3-yl)-N-(3-ethynyloxetan-3-yl)-2-oxoacetamido)methyl phosphate (1.15 g, 76%). LC-MS: (ES, m/z): 531 $[M-H]^-$. $^1H$ NMR (400 MHz, $D_2O$), δ 7.94 (m, 1H), 7.74 (m, 1H), 7.31 (dd, 1H), 5.16 (d, 2H), 5.0 (d, 2H), 4.82 (d, 2H), 3.56 (s, 3H), 2.45 (s, 3H), 2.28 (s, 3H).

Example 10

Compound 73

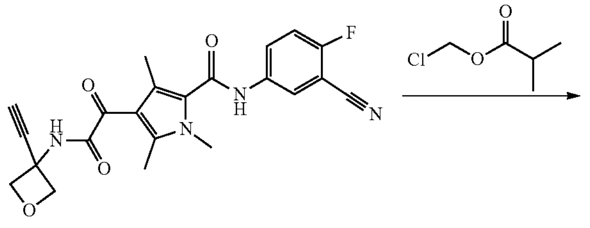

26

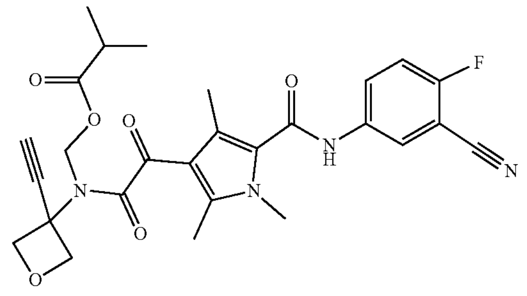

73

To a stirred at 0° C. solution of Compound 26 (844 mg, 2 mmol) and chloromethyl isobutyrate (0.379 mL, 3 mmol, 1.5 eq.) in DMF (15 ml) was added sodium hydride (176 mg as 60% dispersion in mineral oil, 4.4 mmol, 2.2 eq.). The mixture was stirred at rt for 2 h, and then partitioned between half-saturated aqueous solution of ammonium chloride and ethyl acetate. The organic phase was separated, dried over sodium sulfate and concentrated under reduced pressure. [[2-[5-[(3-cyano-4-fluoro-phenyl)carbamoyl]-1,2,4-trimethyl-pyrrol-3-yl]-2-oxo-acetyl]-(3-ethynyloxetan-3-yl)amino]methyl 2-methylpropanoate (Compound 73, 530 mg, 50.8%) was isolated by column chromatography (5 to 25% ethyl acetate in dichloromethane) followed by crystallization from isopropyl acetate. LC-MS: (ES, m/z): 523 $[M+H)]^+$. $^1H$ NMR (400 MHz, DMSO-$d_6$), δ 10.6 (bs, 1H), 8.22 (dd, 1H), 7.98 (m, 1H), 7.55 (dd, 1H), 5.47 (s, 2H), 4.93 (d, 2H), 4.65 (d, 2H), 3.71 (s, 1H), 3.62 (s, 3H), 2.48 (m, 1H), 2.45 (s, 3H), 2.28 (s, 3H), 1.05 (d, 6H).

Example 11

Compound 77

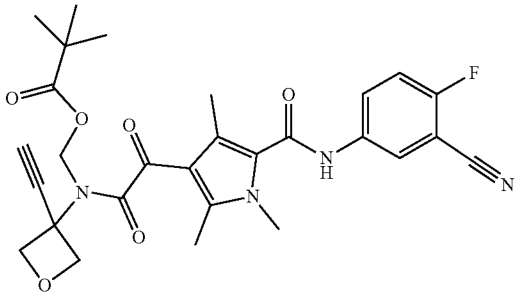 [SMILES: C#CC1(N(COC(=O)C(C)(C)C)C(=O)C(=O)c2c(C)c(C(=O)Nc3ccc(F)c(C#N)c3)n(C)c2C)COC1]

[[2-[5-[(3-cyano-4-fluoro-phenyl)carbamoyl]-1,2,4-trimethyl-pyrrol-3-yl]-2-oxo-acetyl]-(3-ethynyloxetan-3-yl)amino]methyl 2,2-dimethylpropanoate was synthesized as described in Example 10 using pivaloyl chloride in place of chloromethyl isobutyrate. Compound 77 (800 mg, 74.6%) was isolated by column chromatography (5-25% ethyl acetate in dichloromethane) followed by crystallization from ethyl acetate:hexane. LC-MS: (ES, m/z): 537 $[M+H)]^+$. $^1H$ NMR (400 MHz, DMSO-$d_6$), δ 10.6 (bs, 1H), 8.21 (dd, 1H), 7.97 (m, 1H), 7.55 (dd, 1H), 5.46 (s, 2H), 4.93 (d, 2H), 4.66 (d, 2H), 3.73 (s, 1H), 3.62 (s, 3H), 2.45 (s, 3H), 2.28 (s, 3H), 1.07 (s, 9H).

Example 12

Compound 78

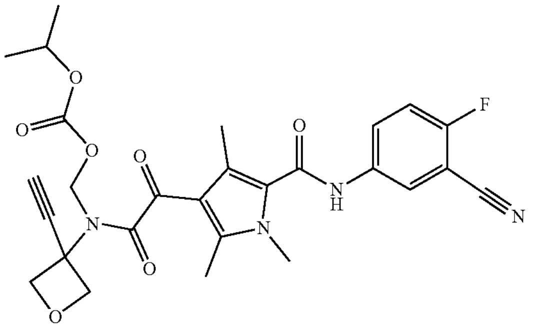 [SMILES: C#CC1(N(COC(=O)OC(C)C)C(=O)C(=O)c2c(C)c(C(=O)Nc3ccc(F)c(C#N)c3)n(C)c2C)COC1]

[[2-[5-[(3-cyano-4-fluoro-phenyl)carbamoyl]-1,2,4-trimethyl-pyrrol-3-yl]-2-oxo-acetyl]-(3-ethynyloxetan-3-yl)amino]methyl isopropyl carbonate was synthesized as described in Example 10 using chloromethyl isopropyl carbonate in place of chloromethyl isobutyrate. Compound 78 (770 mg, 71.6%) was isolated by column chromatography (5-30% ethyl acetate in dichloromethane) followed by crystallization from ethyl acetate:hexane. LC-MS: (ES, m/z): 539 $[M+H)]^+$. $^1H$ NMR (400 MHz, DMSO-$d_6$), δ 10.6 (bs, 1H), 8.22 (dd, 1H), 7.98 (m, 1H), 7.56 (dd, 1H), 5.49 (s, 2H), 4.92 (d, 2H), 4.71 (m, 1H), 4.65 (d, 2H), 3.71 (s, 1H), 3.62 (s, 3H), 2.44 (s, 3H), 2.27 (s, 3H), 1.20 (d, 6H).

Example 13

Compound 66b

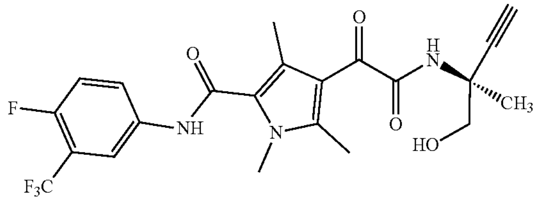

90% hydroxyacetone (16.59 g) and 4-dimethylaminopyridine (1.37 g, 0.05 eq.) were combined in a reactor and diluted with dichloromethane (100 mL). tert-butyldiphenylsilyl chloride (63.40 g, 1.03 eq.) was added, and then rinsed with dichloromethane (230 mL). The solution was cooled with a rt water bath and stirred while triethylamine (36 mL, 1.15 eq.) was added over 1 min. After 3 mins, the solids began to precipitate. After 18 h, the mixture was concentrated and hexane (350 mL) and water (200 mL) were added. The aqueous phase removed via a separatory funnel. The organic phase was washed water (2×150 mL), dried with sodium sulfate and concentrated to provide 1-((tert-butyldiphenylsilyl)oxy)propan-2-one (72.62 g). $^1$H NMR ($CDCl_3$, 400 MHz): δ 7.70 (4H, d), 7.47 (6H, m), 4.20 (2H, s), 2.22 (3H, s), 1.13 (9H, s).

(R)-(+)-2-Methyl-2-propanesulfinamide (18.47 g, 1.0 eq.), 1-((tert-butyldiphenylsilyl)oxy)propan-2-one (47.62 g, 1.0 eq.), and toluene (500 mL) were combined in a reactor under Ar. Titanium tetraisopropanoate (75.8 g, 1.75 eq.) was added, and then the mixture was rinsed with toluene (400 mL). The solution was heated at 100° C. for 23 h. After cooling to rt, sat. aq. sodium bicarbonate (50 mL) was added, and the mixture stirred for 2 mins. The resulting slurry was filtered through Celite, and the organic phase was dried with sodium sulfate. The solution was concentrated to a brown liquid that was purified by normal phase silica gel chromatography using an ethyl acetate-hexanes gradient to afford the product sulfinimine as a red oil (13.8 g). The product was dissolved in toluene (90 mL) and then loaded into an addition funnel above a reaction flask. The reaction flask was loaded with trimethylsilylacetylene (9.78 g, 3.0 eq.) and toluene (230 mL). An Ar atmosphere was established, and the mixture stirred and cooled with a dry ice-acetone bath. 2.5 M n-butyllithium in hexane (33.1 mL, 2.5 eq.) was added below an internal temperature of −61° C. After stirring for 1 h and 10 mins, the sulfinimine solution was added over 1 h, and the internal temperature remained below −67° C. during this time. The mixture was stirred for 1.5 h before the cooling bath was removed. The mixture was warmed slowly by the agency of the surrounding air until −20° C., when the reaction was warmed to 0° C. by immersion in a rt-water bath. Water (20 mL) was added, and the mixture was stirred for 2 mins. The mixture was then filtered through Celite. The organic phase was dried with sodium sulfate and concentrated to give a brown oil (16.8 g) that was purified by normal phase silica gel chromatography using a dichloromethane-ethyl acetate gradient to give (R)—N—((S)-1-((tert-butyldiphenylsilyl)oxy)-2-methyl-4-(trimethylsilyl)but-3-yn-2-yl)-2-methylpropane-2-sulfinamide (6.00 g) as an orange oil. $^1$H NMR ($CDCl_3$, 400 MHz): δ 7.75 (4H, m), 7.45 (6H, m), 3.90 (1H, s), 3.80 (1H, d), 3.60 (1H, d), 1.50 (3H, s), 1.25 (9H, s), 1.10 (9H, s), 0.20 (9H, s).

(R)—N—((S)-1-((tert-butyldiphenylsilyl)oxy)-2-methyl-4-(trimethylsilyl)but-3-yn-2-yl)-2-methylpropane-2-sulfinamide (6.00 g, 1.0 eq.) was dissolved with 1,4-dioxane (70 mL) then 4M HCl (12 mL) in 1,4-dioxane (4.1 eq.). The solution was stirred for 1 h, and then concentrated. Toluene (75 mL) was added, and the solution was concentrated. To the concentrate was added 2-(5-((4-fluoro-3-(trifluoromethyl)phenyl)carbamoyl)-1,2,4-trimethyl-1H-pyrrol-3-yl)-2-oxoacetic acid (4.50 g, 1.0 eq.), HATU (6.47 g, 1.46 eq.), N,N-dimethylformamide (250 mL), and N,N-diisopropylethylamine (17.8 mL, 9.0 eq.). The solution was stirred for 21 h, and then concentrated. Ethyl acetate (250 mL) was added. The resulting solution was washed with water (100 mL) and brine (50 mL), dried with sodium sulfate, concentrated and mixed with dichloromethane (60 mL). The slurry was filtered. The filtrate was concentrated and purified by normal phase silica gel chromatography using an ethyl acetate-hexane gradient to provide the product (7.58 g) as a yellow foam. $^1$H NMR ($CDCl_3$, 400 MHz): δ 7.90 (1H, m), 7.77 (5H, m), 7.63 (1H, s), 7.43 (6H, m), 7.25 (2H, m), 3.91 (1H, d), 3.85 (1H, d), 3.71 (3H, s), 2.41 (6H, s), 1.71 (3H, s), 1.12 (9H, s), 0.20 (9H, s). LC-MS: (ES, m/z): 778 [M+1].

The starting material (7.58 g) was dissolved in THF (75 mL), and 1.0 M tetrabutylammonium fluoride (24 mL, 2.5 eq.) in THF was added. The solution was stirred for 2 h, and then concentrated. The concentrate was dissolved with ethyl acetate (100 mL). The resulting solution was washed water (3×50 mL) and brine (30 mL), dried with sodium sulfate and concentrated to give a yellow oil (7.3 g). The oil was purified by normal phase silica gel chromatography using an ethyl acetate-hexane gradient to give a yellow foam (4.11 g) that was dissolved with DMF (30 mL). The mixture was stirred while slowly adding water (30 mL). Crystallization of white solids began after 3 minutes. Stirring of the developing slurry was continued for 1 h and then it was cooled in an ice bath for 0.5 h. The slurry was filtered, washed with 2:1 water:DMF (10 mL), and then with water (20 mL). The filter cake was dried under vacuum at 65° C. to give (S)—N-(4-fluoro-3-(trifluoromethyl)phenyl)-4-(2-((1-hydroxy-2-methylbut-3-yn-2-yl)amino)-2-oxoacetyl)-1,3,5-trimethyl-1H-pyrrole-2-carboxamide (3.46 g) as a white powder. $^1$H NMR ($CDCl_3$, 400 MHz): δ 10.50 (1H, s), 8.47 (1H, s), 8.22 (1H, m), 7.99 (1H, m), 7.51 (1H, t), 5.20 (1H, t), 3.70 (1H, m), 3.60 (3H, s), 3.58 (1H, m), 3.21 (1H, s), 2.42 (3H, s), 2.30 (3H, s), 1.51 (3H, s). LC-MS: (ES, m/z): 468 [M+1]. $\alpha_D^{20}$ 20.6° C. (c=1.03, MeOH).

Example 14

Compound 66a

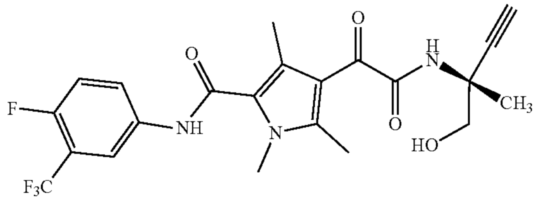 [SMILES: C#C[C@](C)(CO)NC(=O)C(=O)c1c(C)c(C(=O)Nc2ccc(F)c(C(F)(F)F)c2)n(C)c1C]

(S)-(+)-2-Methyl-2-propanesulfinamide (4.82 g, 1.0 eq.), 1-((tert-butyldiphenylsilyl)oxy)propan-2-one (12.43 g, 1.0 eq.), and toluene (310 mL) were combined in a reactor under Ar. Titanium tetraisopropanoate (13.57 g, 1.20 eq.) was added, and then the residue was rinsed with toluene (400 mL). The resulting solution was heated at 100° C. for 18 h. After cooling to rt, sat. aq. sodium bicarbonate (13 mL) was added, and the mixture stirred for 5 mins. The resulting slurry was filtered through Celite, and the organic phase was dried with sodium sulfate. The solution was concentrated to give a brown liquid (16.5 g) that was purified by normal phase silica gel chromatography using an ethyl acetate-hexanes gradient to afford the product sulfinimine (6.07 g) as an orange oil. The oil was dissolved in toluene (50 mL) and loaded into an addition funnel above a reaction flask. The reaction flask was loaded with trimethylsilylacetylene (4.30 g, 3.0 eq.) and toluene (195 mL), and an argon atmosphere established. The mixture was stirred and cooled with a dry ice-acetone bath. 2.5 M n-butyllithium in hexane (14.6 mL, 2.5 eq.) was added below internal temperature of −63° C. After stirring for 1 h and 10 minutes, the solution was warmed to −20° C. for 2 mins. The mixture was cooled below −67° C. while the sulfinimine solution was added over 14 mins. The mixture was stirred for 1 h from −73-(−67) ° C., and then the cooling bath was removed. The contents warmed slowly by the agency of the surrounding air until −40° C., and when the reaction was warmed to 0° C. using immersion in a room temperature-water bath. Water (10 mL) was added. The mixture was stirred for 5 mins, and then filtered through Celite. The organic phase was dried with sodium sulfate and concentrated to give an orange oil (7.55 g) that was partially purified using normal phase silica gel chromatography and an ethyl acetate-hexane gradient to give an orange oil (4.10 g). The oil was further purified using normal phase silica gel chromatography and an ethyl acetate-dichloromethane gradient to give —(S)—N—((R)-1-((tert-butyldiphenylsilyl)oxy)-2-methyl-4-(trimethylsilyl) but-3-yn-2-yl)-2-methylpropane-2-sulfinamide (1.93 g) as a yellow oil. $^1$H NMR ($CDCl_3$, 400 MHz): δ 7.75 (4H, m), 7.45 (6H, m), 3.90 (1H, s), 3.80 (1H, d), 3.60 (1H, d), 1.50 (3H, s), 1.25 (9H, s), 1.10 (9H, s), 0.20 (9H, s).

(S)—N—((R)-1-((tert-butyldiphenylsilyl)oxy)-2-methyl-4-(trimethylsilyl)but-3-yn-2-yl)-2-methylpropane-2-sulfinamide (1.93 g, 1.0 eq.) was dissolved with 1,4-dioxane (40 mL) then 4M hydrogen chloride in 1,4-dioxane (4 mL 4.3 eq.) was added. The solution was stirred for 3 h, and then concentrated. To the concentrate was added 2-(5-((4-fluoro-3-(trifluoromethyl)phenyl)carbamoyl)-1,2,4-trimethyl-1H-pyrrol-3-yl)-2-oxoacetic acid (1.21 g, 0.83 eq.), HATU (1.79 g, 1.25 eq.), N,N-dimethylformamide (75 mL) and N,N-diisopropylethylamine (4.2 mL, 6.42 eq.). The solution was stirred for 16 h, and then concentrated. Ethyl acetate (75 mL) was added. The solution was washed with water (30 mL) and brine (25 mL), dried with sodium sulfate and concentrated to a red solid (5.6 g) that was purified by normal phase silica gel chromatography using an ethyl acetate-hexane gradient to provide the product amide as a yellow foam (2.57 g). $^1$H NMR ($CDCl_3$, 400 MHz): δ 7.90 (1H, m), 7.77 (5H, m), 7.63 (1H, s), 7.43 (6H, m), 7.25 (2H, m), 3.91 (1H, d), 3.85 (1H, d), 3.71 (3H, s), 2.41 (6H, s), 1.71 (3H, s), 1.12 (9H, s), 0.20 (9H, s). LC-MS: (ES, m/z): 778 [M+1].

The starting material (2.57 g) was dissolved in THF (25 mL) and 1.0 M tetrabutylammonium fluoride in THF (8.2 mL, 2.5 eq.) was added. The solution was stirred for 1.5 h, and then concentrated. The concentrate was dissolved with ethyl acetate (30 mL). The solution was washed with water (3×20 mL) and then brine (15 mL). The solution was dried with sodium sulfate and concentrated to a yellow oil (2.6 g) that was purified by normal phase silica gel chromatography using an ethyl acetate-hexane gradient to give a yellow wax (1.4 g). The wax was dissolved with dichloromethane (80 mL), and then warmed to dissolve all solids. The mixture was removed from heat and then stirred while the solution slowly cooled. A slurry developed over 1.5 h. The mixture was cooled for 1 h in an ice bath, and then filtered. The filter cake was washed with ice-cold dichloromethane, and then dried under vacuum at 60° C. to provide (R)—N-(4-fluoro-3-(trifluoromethyl)phenyl)-4-(2-((1-hydroxy-2-methylbut-3-yn-2-yl)amino)-2-oxoacetyl)-1,3,5-trimethyl-1H-pyrrole-2-carboxamide (0.90 g) as a white powder. $^1$H NMR ($CDCl_3$, 400 MHz): δ 10.50 (1H, s), 8.47 (1H, s), 8.22 (1H, m), 7.99 (1H, m), 7.51 (1H, t), 5.20 (1H, t), 3.70 (1H, m), 3.60 (3H, s), 3.58 (1H, m), 3.21 (1H, s), 2.42 (3H, s), 2.30 (3H, s), 1.51 (3H, s). LC-MS: (ES, m/z): 468 [M+1]. $\alpha_D^{20}$ −22.4° C. (c=0.98, MeOH).

Example 15

Compounds 165a & 165b

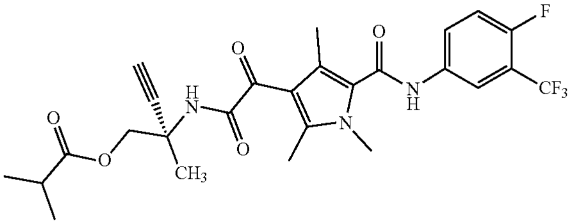

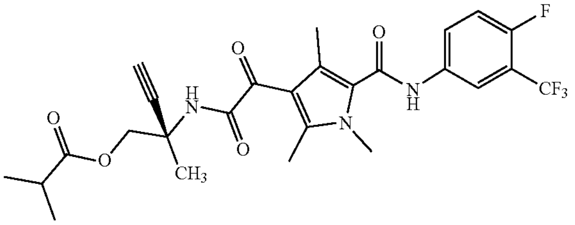

To a stirred solution of (R)—N-(4-fluoro-3-(trifluoromethyl)phenyl)-4-(2-((1-hydroxy-2-methylbut-3-yn-2-yl) amino)-2-oxoacetyl)-1,3,5-trimethyl-1H-pyrrole-2-carboxamide (233.5 mg, 0.5 mmol) in DCM (3 mL) and pyridine (0.2 mL) was added isobutyryl chloride (0.126 mL, 1.2 mmol). The mixture was warmed up to 40° C. and stirred overnight. After the reaction was quenched with methanol, the mixture was partitioned between isopropyl acetate and 1M sodium dihydrogen phosphate. The organic layer was separated, and the solvent was removed under reduced pressure. The residue was purified by column chromatography (20 to 50% ethyl acetate-hexane) to furnish 165a (192 mg, 71%) as a light-yellow foam. LC-MS: (ES, m/z): 538.4 [M+H]. $^1$H NMR ($CDCl_3$, 400 MHz): δ 7.91 (m, 1H), 7.77 (m, 1H), 7.65 (br. s, 1H), 7.22 (dd, 1H), 7.17 (br. s, 1H), 4.46 (dd, 2H), 3.73 (s, 3H), 2.65 (m, 1H), 2.46 (s, 1H), 2.42 (s., 3H), 2.41 (s, 3H), 1.75 (s, 3H), 1.22 (d, 6H).

The (S)-enantiomer was synthesized as described for the (R)-enantiomer using (S)—N-(4-fluoro-3-(trifluoromethyl) phenyl)-4-(2-((1-hydroxy-2-methylbut-3-yn-2-yl)amino)-2-oxoacetyl)-1,3,5-trimethyl-1H-pyrrole-2-carboxamide. LC-MS: (ES, m/z): 538.4 [M+H].

Example 16
Compounds 166a & 166b
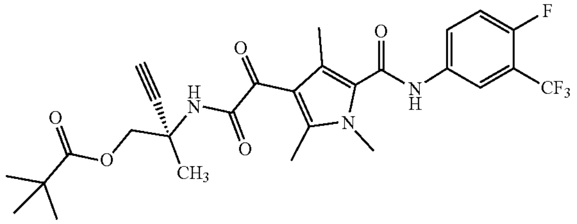
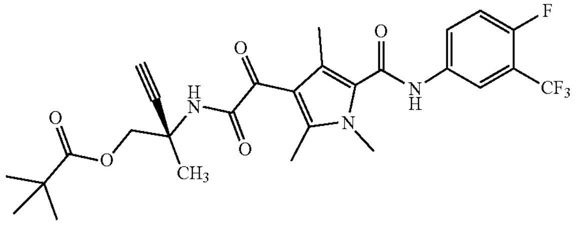
Compounds 166a and 166b were synthesized from the parent alcohol (233 mg, 0.5 mmol) following the procedure described in Example 15 using pivaloyl chloride in place of isobutyryl chloride. 166a (237 mg, 86%). LC-MS: (ES, m/z): 552.5 [M+H]. $^1$H NMR ($CDCl_3$, 400 MHz): δ 7.91 (m, 1H), 7.77 (m, 1H), 7.65 (br. s, 1H), 7.23 (dd, 1H), 7.16 (br. s, 1H), 7.44 (dd, 2H), 3.72 (s, 3H), 2.45 (s, 1H), 2.42 (s, 3H), 2.40 (s, 3H), 1.75 (s, 3H), 1.26 (s, 9H). 166b LC-MS: (ES, m/z): 552.5 [M+H].
Example 17
Compounds 167a & 167b
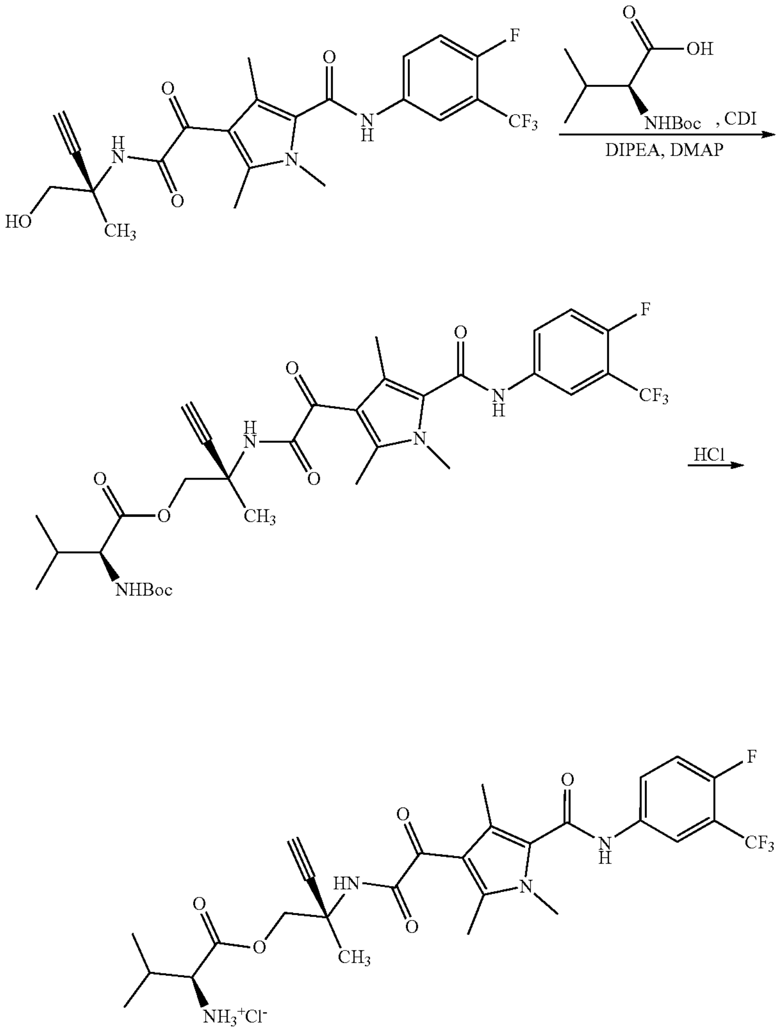

To a stirred solution of Boc-L-valine (214 mg, 0.99 mmol) in acetonitrile (3 mL) was added carbonyldiimidazole (160 mg, 0.99 mmol). After 1 h, a solution of the imidazolide was added to a solution of (S)—N-(4-fluoro-3-(trifluoromethyl) phenyl)-4-(2-((1-hydroxy-2-methylbut-3-yn-2-yl)amino)-2-oxoacetyl)-1,3,5-trimethyl-1H-pyrrole-2-carboxamide (307 mg, 0.66 mmol), DIPEA (0.343 mL, 1.97 mmol) and DMAP (16 mg, 0.13 mmol) in acetonitrile (2 mL). The reaction was allowed to proceed for 1 h at rt, and then the reaction was quenched with water. The solution was taken into isopropyl acetate and 1M sodium dihydrogen phosphate. The organic phase was separated, washed with sodium bicarbonate and concentrated under reduced pressure. The residue was purified by column chromatography (20 to 50% ethyl acetate-hexane) to afford the Boc-protected intermediate as a slight yellow foam that was then dissolved in ethyl acetate (4 mL). The solution was treated with 4M hydrogen chloride solution in dioxane (1.9 mL, 7.6 mmol). After 3.5 h the mixture was concentrated under reduced pressure, and the residue was triturated with MTBE (5 mL). The resulting solid was isolated by filtration. The filter cake was rinsed with MTBE and the product (370 mg, 93%) was dried under vacuum. LC-MS: (ES, m/z): 567.7 [M−HCl+H]. $^1$H NMR (400 MHz, DMSO-$d_6$) δ:10.58 (s, 1H), 9.00 (s, 1H), 8.45 (br. s, 3H), 8.23 (m, 1H), 7.98 (m, 1H), 7.53 (dd, 1H), 4.53 (dd, 2H), 3.53 (s, 3H), 3.48 (s, 1H), 2.43 (s, 3H), 2.26 (s, 3H), 1.60 (s, 3H), 1.03-0.93 (m, 7H).

The (R)-enantiomer was obtained as described for the (S)-enantiomer using (R)—N-(4-fluoro-3-(trifluoromethyl) phenyl)-4-(2-((1-hydroxy-2-methylbut-3-yn-2-yl)amino)-2-oxoacetyl)-1,3,5-trimethyl-1H-pyrrole-2-carboxamide. LC-MS: (ES, m/z): 567.7 [M−HCl+H].

Example 18

Compounds 168a & 168b

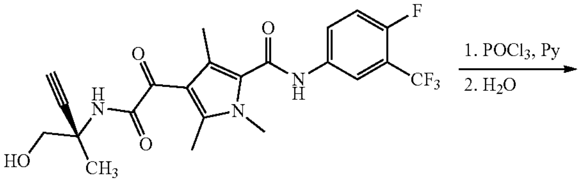

-continued

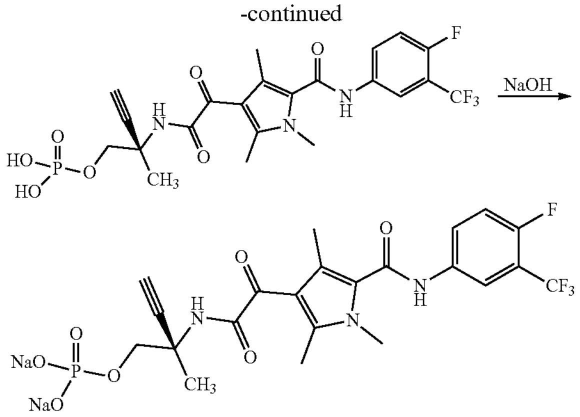

To a stirred at 0° C. solution of (S)—N-(4-fluoro-3-(trifluoromethyl)phenyl)-4-(2-((1-hydroxy-2-methylbut-3-yn-2-yl)amino)-2-oxoacetyl)-1,3,5-trimethyl-1H-pyrrole-2-carboxamide (4.82 g, 10.4 mmol) in THF (100 mL) and pyridine (2.44 mL, 31 mmol) was added phosphorus oxychloride (2.88 mL, 31 mmol). The mixture was stirred for 1 h at 0° C., and then the reaction was quenched with water (30 mL). The mixture was warmed to rt and stirred for 1 h. The mixture was diluted with ethyl acetate, and the solution was washed with water (3×). The organic phase was concentrated to dryness, and the residue was dissolved in isopropanol (100 mL). An aqueous solution (2M) of NaOH was added slowly until pH~8.5 (9.7 mL). A precipitate formed upon addition of NaOH and was isolated by filtration. The filter cake was rinsed with isopropanol and dried under vacuum to afford the product (5.19 g, 83%). LC-MS: (ES, m/z): 548.1 [M−2Na+3H]. $^1$H NMR (400 MHz, $D_2O$) δ: 7.83 (m, H), 7.66 (m, 1H), 7.31 (dd, 1H), 3.91 (split dd, 2H), 3.54 (s, 3H), 2.80 (s, 1H), 2.40 (s, 3H), 2.29 (s, 3H), 1.61 (s, 3H). $^{31}$P NMR (162 MHz, $D_2O$) δ: 4.08 (s).

The (R)-enantiomer was obtained as described for the (S)-enantiomer using (R)—N-(4-fluoro-3-(trifluoromethyl) phenyl)-4-(2-((1-hydroxy-2-methylbut-3-yn-2-yl)amino)-2-oxoacetyl)-1,3,5-trimethyl-1H-pyrrole-2-carboxamide. LC-MS: (ES, m/z): 548.1 [M−2Na+3H].

Example 19

The following compounds were made following similar procedures and starting materials as described in the Examples above.

| Compound Name | Compound No. | $^1$H NMR |
|---|---|---|
| N-(3-cyano-4-fluoro-phenyl)-3-fluoro-1-methyl-4-[2-oxo-2-(prop-2-ynylamino)acetyl]pyrrole-2-carboxamide | 6 | $^1$H NMR (400 MHz, DMSO-$d_6$) δ 10.36 (s, 1H), 9.22 (s, 1H), 8.21-8.15 (m, 1H), 8.12 (d, J = 4.2 Hz, 1H), 7.96 (s, 1H), 7.53 (t, J = 9.1 Hz, 1H), 4.00-3.93 (s, 2H), 3.85 (s, 3H), 3.14 (s, 1H) |
| 4-[2-(allylamino)-2-oxo-acetyl]-N-(3-cyano-4-fluoro-phenyl)-3-fluoro-1-methyl-pyrrole-2-carboxamide | 7 | $^1$H NMR (400 MHz, DMSO-$d_6$) δ 10.35 (s, 1H), 8.96 (t, J = 6.0 Hz, 1H), 8.18 (dd, J = 5.9, 2.7 Hz, 1H), 8.11 (d, J = 4.3 Hz, 1H), 7.96 (m, 1H), 7.54 (t, J = 9.1 Hz, 1H), 5.85 (m, 1H), 5.20-5.06 (m, 2H), 3.85 (s, 3H), 3.83 (d, J = 5.6 Hz, 2H) |
| N-(3-cyano-4-fluoro-phenyl)-1,3-dimethyl-4-[2-oxo-2-(prop-2-ynylamino)acetyl]pyrrole-2-carboxamide | 8 | $^1$H NMR (300 MHz, DMSO-$d_6$) δ 10.56-10.50 (m, 1H), 9.09 (d, J = 5.6 Hz, 1H), 8.20 (m, J = 5.8, 2.7 Hz, 1H), 8.14 (s, 1H), 8.03-7.91 (m, 1H), 7.55 (t, J = 9.2 Hz, |

-continued

| Compound Name | Compound No. | $^1$H NMR |
|---|---|---|
| | | 1H), 3.96 (m, J = 5.9, 2.5 Hz, 2H), 3.77 (s, 3H), 3.14 (t, J = 2.5 Hz, 1H), 2.40 (s, 3H) |
| 5-chloro-N-(3-cyano-4-fluoro-phenyl)-1,3-dimethyl-4-[2-oxo-2-(prop-2-ynylamino)acetyl]pyrrole-2-carboxamide | 9 | $^1$H NMR (300 MHz, DMSO-$d_6$) δ 10.67 (s, 1H), 9.21 (t, J = 5.7 Hz, 1H), 8.20 (m, 1H), 8.02-7.91 (m, 1H), 7.56 (t, J = 9.1 Hz, 1H), 4.01 (m 2H), 3.68 (s, 3H), 3.19 (t, J = 2.5 Hz, 1H), 2.29 (s, 3H) |
| 3-chloro-N-(3-cyano-4-fluoro-phenyl)-1-methyl-4-[2-oxo-2-(prop-2-ynylamino)acetyl]pyrrole-2-carboxamide | 10 | $^1$H NMR (300 MHz, DMSO-$d_6$) δ 10.76 (s, 1H), 9.24 (t, J = 5.8 Hz, 1H), 8.27 (s, 1H), 8.22 (m, 1H), 7.99 (m, 1H), 7.57 (t, J = 9.1 Hz, 1H), 3.98 (m, 2H), 3.87 (s, 3H), 3.17 (t, J = 2.5 Hz, 1H) |
| N-(3-cyano-4-fluoro-phenyl)-4-[2-(1,1-dimethylprop-2-ynylamino)-2-oxo-acetyl]-1,3,5-trimethyl-pyrrole-2-carboxamide | 11 | $^1$H NMR (400 MHz, DMSO-$d_6$) δ 10.52 (s, 1H), 8.76 (s, 1H), 8.22 (m, 1H), 7.98 (m, 1H), 7.54 (t, J = 9.1 Hz, 1H), 3.61 (s, 3H), 3.20 (s, 1H), 2.44 (s, 3H), 2.29 (s, 3H), 1.57 (s, 6H) |
| 5-chloro-N-(3-cyano-4-fluoro-phenyl)-3-fluoro-1-methyl-4-[2-oxo-2-(prop-2-ynylamino)acetyl]pyrrole-2-carboxamide | 12 | $^1$H NMR (400 MHz, DMSO-$d_6$) δ 10.57 (s, 1H), 9.30 (t, J = 5.6 Hz, 1H), 8.17 (m, 1H), 7.96 (m, 1H), 7.55 (t, J = 9.1 Hz, 1H), 4.02 (m, 2H), 3.81 (s, 3H), 3.21 (t, J = 2.5 Hz, 1H) |
| N-(3-cyano-4-fluoro-phenyl)-3-fluoro-1,5-dimethyl-4-[2-oxo-2-(prop-2-ynylamino)acetyl]pyrrole-2-carboxamide | 13 | $^1$H NMR (300 MHz, Methanol-$d_4$) δ 8.12 (dd, J = 5.7, 2.7 Hz, 1H), 7.88 (m, 1H), 7.34 (t, J = 9.0 Hz, 1H), 4.09 (d, J = 2.6 Hz, 2H), 3.81 (s, 3H), 2.65 (t, J = 2.6 Hz, 1H), 2.53 (s, 3H) |
| N-(3-cyano-4-fluoro-phenyl)-4-[2-[(1-ethynylcyclopropyl)amino]-2-oxo-acetyl]-1,3,5-trimethyl-pyrrole-2-carboxamide | 14 | $^1$H NMR (400 MHz, DMSO-$d_6$) δ 10.52 (s, 1H), 9.27 (s, 1H), 8.21 (dd, J = 5.8, 2.7 Hz, 1H), 7.97 (m, 1H), 7.54 (t, J = 9.2 Hz, 1H), 3.59 (s, 3H), 3.06 (s, 1H), 2.40 (s, 3H), 2.23 (s, 3H), 1.21-1.10 (m, 2H), 1.10-1.00 (m, 2H) |
| N-(3-cyano-4-fluoro-phenyl)-4-[2-[(1-ethynylcyclobutyl)amino]-2-oxo-acetyl]-1,3,5-trimethyl-pyrrole-2-carboxamide | 15 | $^1$H NMR (400 MHz, DMSO-$d_6$) δ 10.53 (s, 1H), 9.20 (s, 1H), 8.22 (m, 1H), 7.98 (m, 1H), 7.55 (t, J = 9.1 Hz, 1H), 3.61 (s, 3H), 3.23 (s, 1H), 2.46-2.37 (m, 7H), 2.28 (s, 3H), 1.97 (m, 2H) |
| 5-bromo-3-chloro-N-(3-cyano-4-fluoro-phenyl)-1-methyl-4-[2-oxo-2-(prop-2-ynylamino)acetyl]pyrrole-2-carboxamide | 16 | $^1$H NMR (400 MHz, DMSO-$d_6$) δ 10.93 (s, 1H), 9.31 (t, J = 4.8 Hz, 1H), 8.27 (s, 1H), 7.97 (s, 1H), 7.57 (t, J = 9.1 Hz, 1H), 4.02 (d, J = 2.4 Hz, 2H), 3.75 (s, 3H), 3.20 (s, 1H) |
| N-(3-cyano-4-fluoro-phenyl)-1,3,5-trimethyl-4-[2-oxo-2-[[(1R)-1-methylprop-2-ynyl]amino]acetyl]pyrrole-2-carboxamide | 17a | $^1$H NMR (300 MHz, DMSO-$d_6$) δ 10.54 (s, 1H), 9.18 (d, J = 7.9 Hz, 1H), 8.22 (m, 1H), 7.98 (m, 1H), 7.55 (t, J = 9.1 Hz, 1H), 4.76-4.64 (m, 1H), 3.60 (s, 3H), 3.25 (d, J = 2.3 Hz, 1H), 2.42 (s, 3H), 2.25 (s, 3H), 1.38 (d, J = 7.0 Hz, 3H) |
| N-(3-cyano-4-fluoro-phenyl)-1,3,5-trimethyl-4-[2-oxo-2-[[(1S)-1-methylprop-2-ynyl]amino]acetyl]pyrrole-2-carboxamide | 17b | $^1$H NMR (300 MHz, DMSO-$d_6$) δ 10.54 (s, 1H), 9.18 (d, J = 7.9 Hz, 1H), 8.22 (m, 1H), 7.98 (m, 1H), 7.55 (t, J = 9.1 Hz, 1H), 4.70 (m, 1H), 3.60 (s, 3H), 3.25 (d, J = 2.3 Hz, 1H), 2.42 (s, 3H), 2.25 (s, 3H), 1.38 (d, J = 7.0 Hz, 3H) |
| 4-[2-(allylamino)-2-oxo-acetyl]-N-(3-cyano-4-fluoro-phenyl)-3-fluoro-1,5-dimethyl-pyrrole-2-carboxamide | 18 | $^1$H NMR (300 MHz, DMSO-$d_6$) δ 10.36 (s, 1H), 8.88 (t, J = 5.9 Hz, 1H), 8.18 (dd, J = 5.8, 2.8 Hz, 1H), 8.00-7.87 (m, 1H), |

-continued

| Compound Name | Compound No. | $^1$H NMR |
|---|---|---|
| | | 7.54 (t, J = 9.2 Hz, 1H), 5.97-5.81 (m, 1H), 5.31-5.09 (m, 2H), 3.82 (t, J = 5.6 Hz, 2H), 3.72 (s, 3H), 2.55 (s, 3H) |
| 5-bromo-N-(3-cyano-4-fluoro-phenyl)-3-fluoro-1-methyl-4-[2-oxo-2-(prop-2-ynylamino)acetyl]pyrrole-2-carboxamide | 20 | $^1$H NMR (400 MHz, DMSO-$d_6$) δ 9.27 (s, 1H), 8.16 (m, 1H), 7.99-7.90 (m, 1H), 7.54 (t, J = 9.2 Hz, 1H), 4.01 (dd, J = 5.6, 2.6 Hz, 2H), 3.81 (s, 3H), 3.19 (t, J = 2.6 Hz, 1H) |
| 3-chloro-N-(3-cyano-4-fluoro-phenyl)-1,5-dimethyl-4-[2-oxo-2-(prop-2-ynylamino)acetyl]pyrrole-2-carboxamide | 21 | $^1$H NMR (300 MHz, DMSO-$d_6$) δ 10.76 (s, 1H), 9.20 (t, J = 5.6 Hz, 1H), 8.22 (dd, J = 5.8, 2.7 Hz, 1H), 7.99 (m, 1H), 7.56 (t, J = 9.1 Hz, 1H), 4.01 (dd, J = 5.6, 2.5 Hz, 2H), 3.66 (s, 3H), 3.18 (t, J = 2.5 Hz, 1H), 2.51 (s, 3H) |
| N-(3-cyano-4-fluoro-phenyl)-4-[2-(3-cyclopropylprop-2-ynylamino)-2-oxo-acetyl]-1,3,5-trimethyl-pyrrole-2-carboxamide | 22 | $^1$H NMR (300 MHz, DMSO-$d_6$) δ 10.55 (s, 1H), 9.05 (t, J = 5.6 Hz, 1H), 8.22 (dd, J = 5.8, 2.7 Hz, 1H), 7.97 (m, 1H), 7.55 (t, J = 9.1 Hz, 1H), 3.94 (dd, J = 5.6, 2.0 Hz, 2H), 3.61 (s, 3H), 2.40 (s, 3H), 2.24 (s, 3H), 1.36-1.20 (m, 1H), 0.83-0.65 (m, 2H), 0.64-0.49 (m, 2H) |
| N-(3-cyano-4-fluoro-phenyl)-1,3,5-trimethyl-4-[2-oxo-2-[[(1R)-1-cyclopropylprop-2-ynyl]amino]acetyl]pyrrole-2-carboxamide | 23a | $^1$H NMR (400 MHz, DMSO-$d_6$) δ 10.53 (s, 1H), 9.30 (d, J = 8.2 Hz, 1H), 8.21 (dd, J = 5.8, 2.7 Hz, 1H), 7.97 (ddd, J = 9.2, 4.9, 2.7 Hz, 1H), 7.54 (t, J = 9.1 Hz, 1H), 4.35 (td, J = 7.9, 2.4 Hz, 1H), 3.24 (d, J = 2.3 Hz, 1H), 2.42 (s, 3H), 2.26 (s, 3H), 1.25-1.15 (m, 1H), 0.69-0.14 (m, 4H) |
| 5-chloro-N-(3-cyano-4-fluoro-phenyl)-1-methyl-4-[2-oxo-2-(prop-2-ynylamino)acetyl]pyrrole-2-carboxamide | 25 | $^1$H NMR (300 MHz, DMSO-$d_6$) δ 10.58 (s, 1H), 9.28 (t, J = 5.7 Hz, 1H), 8.22 (m, 1H), 8.09-7.97 (m, 1H), 7.89 (s, 1H), 7.55 (t, J = 9.1 Hz, 1H), 4.02 (m, 2H), 3.93 (s, 3H), 3.18 (t, J = 2.5 Hz, 1H) |
| N-(3-cyano-4-fluoro-phenyl)-4-[2-[[(1S)-1-(methoxymethyl)prop-2-ynyl]amino]-2-oxo-acetyl]-1,3,5-trimethyl-pyrrole-2-carboxamide | 28a | $^1$H NMR (300 MHz, DMSO-$d_6$) δ 10.54 (s, 1H), 9.21 (d, J = 8.3 Hz, 1H), 8.22 (m, 1H), 7.98 (m, 1H), 7.55 (m, 1H), 4.91-4.78 (m, 1H), 3.61-3.54 (m, 5H), 3.36 (m, 3H), 2.52 (s, 1H), 2.42 (s, 3H), 2.26 (s, 3H) |
| N-(3-cyano-4-fluoro-phenyl)-4-[2-[[(1R)-1-(methoxymethyl)prop-2-ynyl]amino]-2-oxo-acetyl]-1,3,5-trimethyl-pyrrole-2-carboxamide | 28b | $^1$H NMR (300 MHz, DMSO-$d_6$) δ 10.54 (s, 1H), 9.21 (d, J = 8.3 Hz, 1H), 8.22 (m, 1H), 7.98 (m, 1H), 7.55 (m, 1H), 4.91-4.78 (m, 1H), 3.61 (m, 3H), 3.54 (m, 2H), 3.36 (m, 3H), 2.52 (s, 1H), 2.42 (s, 3H), 2.26 (s, 3H) |
| N-(3-cyano-4-fluoro-phenyl)-1,3,5-trimethyl-4-[2-oxo-2-[[3-(1H-triazol-4-yl)oxetan-3-yl]amino]acetyl]pyrrole-2-carboxamide | 29 | $^1$H NMR (400 MHz, DMSO-$d_6$) δ 15.01 (s, 1H), 10.52 (s, 1H), 9.90 (s, 1H), 8.21 (t, J = 8.4 Hz, 1H), 7.97 (s, 1H), 7.83 (s, 1H), 7.55 (t, J = 9.0 Hz, 1H), 4.92 (s, 4H), 3.59 (s, 3H), 2.35 (s, 3H), 2.20 (s, 3H) |
| N-(3-cyano-4-fluoro-phenyl)-1,3,5-trimethyl-4-[2-oxo-2-[[(1S)-1-tert-butylprop-2-ynyl]amino]acetyl]pyrrole-2-carboxamide | 30b | $^1$H NMR (300 MHz, DMSO-$d_6$) δ 10.54 (s, 1H), 9.03 (d, J = 9.3 Hz, 1H), 8.22 (dd, J = 5.8, 2.7 Hz, 1H), 7.95-8.01 (m, 1H), 7.55 (t, J = 9.1 Hz, 1H), 4.53 (dd, J = 9.2, 2.5 Hz, 1H), 3.61 (s, 3H), 3.26 (d, J = 2.4 Hz, 1H), 2.43 (s, 3H), 2.27 (s, 3H), 1.00 (s, 9H) |
| N-(3-cyano-4-fluoro-phenyl)-1,3,5-trimethyl-4-[2-oxo-2-[(3-vinyloxetan-3-yl)amino]acetyl]pyrrole-2-carboxamide | 33 | $^1$H NMR (400 MHz, DMSO-$d_6$) δ 10.52 (s, 1H), 9.42 (s, 1H), 8.20 (dd, J = 5.8, 2.7 Hz, 1H), 7.96 (ddd, J = 9.2, 4.9, 2.7 Hz, |

-continued

| Compound Name | Compound No. | $^1$H NMR |
|---|---|---|
| | | 1H), 7.53 (t, J = 9.1 Hz, 1H), 6.28 (dd, J = 17.2, 10.5 Hz, 1H), 5.31 (dd, J = 17.3, 1.1 Hz, 1H), 5.20 (dd, J = 10.5, 1.0 Hz, 1H), 4.71 (d, J = 6.6 Hz, 2H), 4.57 (d, J = 6.6 Hz, 2H), 3.59 (s, 3H), 2.42 (s, 3H), 2.27 (s, 3H) |
| 4-[2-[(3-ethynyloxetan-3-yl)amino]-2-oxo-acetyl]-N-[4-fluoro-3-(trifluoromethyl)phenyl]-1,3,5-trimethyl-pyrrole-2-carboxamide | 34 | $^1$H NMR (400 MHz, DMSO-$d_6$) δ 10.51 (s, 1H), 9.74 (s, 1H), 8.20 (dd, J = 6.6, 2.6 Hz, 1H), 7.99-7.90 (m, 1H), 7.50 (t, J = 9.8 Hz, 1H), 4.72 (d, J = 6.6 Hz, 4H), 3.65 (s, 1H), 3.59 (s, 3H), 2.41 (s, 3H), 2.25 (s, 3H) |
| 4-[2-(1,1-dimethylprop-2-ynylamino)-2-oxo-acetyl]-N-[4-fluoro-3-(trifluoromethyl)phenyl]-1,3,5-trimethyl-pyrrole-2-carboxamide | 35 | $^1$H NMR (300 MHz, DMSO-$d_6$) δ 10.52 (s, 1H), 8.77 (s, 1H), 8.22 (dd, J = 6.7, 2.6 Hz, 1H), 7.98 (dd, J = 9.0, 4.3 Hz, 1H), 7.53 (t, J = 9.8 Hz, 1H), 3.60 (s, 3H), 3.22 (s, 1H), 2.44 (s, 3H), 2.28 (s, 3H), 1.57 (s, 6H) |
| N-(3-cyano-4-fluoro-phenyl)-1,3,5-trimethyl-4-[2-oxo-2-[[(1R)-1-(trifluoromethyl)allyl]amino]acetyl]pyrrole-2-carboxamide | 36b | $^1$H NMR (300 MHz, DMSO-$d_6$) δ 10.57 (s, 1H), 9.66 (d, J = 9.1 Hz, 1H), 8.22 (dd, J = 5.8, 2.7 Hz, 1H), 7.95-8.01 (m, 1H), 7.55 (t, J = 9.1 Hz, 1H), 5.86-5.98 (m, 1H), 5.65 (d, J = 17.1 Hz, 1H), 5.51 (d, J = 10.4 Hz, 1H), 5.30 (q, J = 8.0 Hz, 1H), 2.41 (s, 3H), 2.23 (s, 3H) |
| N-(3-cyano-4-fluoro-phenyl)-1,3,5-trimethyl-4-[2-oxo-2-[[(1S)-1-(trifluoromethyl)allyl]amino]acetyl]pyrrole-2-carboxamide | 36a | $^1$H NMR (300 MHz, DMSO-$d_6$) δ 10.57 (s, 1H), 9.66 (d, J = 9.1 Hz, 1H), 8.22 (dd, J = 5.8, 2.7 Hz, 1H), 7.95-8.01 (m, 1H), 7.55 (t, J = 9.1 Hz, 1H), 5.86-5.98 (m, 1H), 5.65 (d, J = 17.1 Hz, 1H), 5.51 (d, J = 10.4 Hz, 1H), 5.30 (q, J = 8.0 Hz, 1H), 2.41 (s, 3H), 2.23 (s, 3H) |
| 4-[2-[(1-ethynyl-3,3-difluoro-cyclobutyl)amino]-2-oxo-acetyl]-N-[4-fluoro-3-(trifluoromethyl)phenyl]-1,3,5-trimethyl-pyrrole-2-carboxamide | 37 | $^1$H NMR (300 MHz, DMSO-$d_6$) δ 10.53 (s, 1H), 9.62 (s, 1H), 8.22 (dd, J = 6.7, 2.6 Hz, 1H), 7.97 (dt, J = 8.1, 3.8 Hz, 1H), 7.54 (d, J = 9.9 Hz, 1H), 3.61 (s, 3H), 3.53 (s, 1H), 3.13 (t, J = 12.1 Hz, 4H), 2.43 (s, 3H), 2.27 (s, 3H) |
| N-[4-fluoro-3-(trifluoromethyl)phenyl]-1,3,5-trimethyl-4-[2-oxo-2-[[(1R)-1-cyclopropylprop-2-ynyl]amino]acetyl]pyrrole-2-carboxamide | 38a | $^1$H NMR (400 MHz, DMSO-$d_6$) δ 10.52 (s, 1H), 9.30 (d, J = 8.2 Hz, 1H), 8.20 (dd, J = 6.7, 2.7 Hz, 1H), 7.98-7.90 (m, 1H), 7.50 (t, J = 9.8 Hz, 1H), 4.33 (td, J = 7.9, 2.4 Hz, 1H), 3.58 (s, 3H), 3.24 (d, J = 2.4 Hz, 1H), 2.41 (s, 3H), 2.25 (s, 3H), 1.18 (dt, J = 8.0, 6.5 Hz, 1H), 0.51 (dddd, J = 12.7, 7.0, 4.8, 3.2 Hz, 2H), 0.45-0.38 (m, 1H), 0.37-0.30 (m, 1H) |
| N-[4-fluoro-3-(trifluoromethyl)phenyl]-1,3,5-trimethyl-4-[2-oxo-2-[[(1S)-1-cyclopropylprop-2-ynyl]amino]acetyl]pyrrole-2-carboxamide | 38b | $^1$H NMR (400 MHz, DMSO-$d_6$) δ 10.52 (s, 1H), 9.30 (d, J = 8.2 Hz, 1H), 8.20 (dd, J = 6.6, 2.7 Hz, 1H), 7.94 (dt, J = 7.6, 3.5 Hz, 1H), 7.50 (t, J = 9.8 Hz, 1H), 4.33 (td, J = 7.9, 2.4 Hz, 1H), 3.58 (s, 3H), 3.24 (d, J = 2.3 Hz, 1H), 2.41 (s, 3H), 2.25 (s, 3H), 1.18 (dtd, J = 12.7, 7.9, 4.6 Hz, 1H), 0.56-0.46 (m, 2H), 0.42 (ddd, J = 10.8, 5.6, 3.1Hz, 1H), 0.34 (ddd, J = 10.7, 4.9, 2.3 Hz, 1H) |
| 5-chloro-N-(3-cyano-4-fluoro-phenyl)-4-[2-[(1-ethynyl-3,3-difluoro-cyclobutyl)amino]-2-oxo-acetyl]-1,3-dimethyl-pyrrole-2-carboxamide | 39 | $^1$H NMR (400 MHz, DMSO-$d_6$) δ 10.67 (s, 1H), 9.67 (s, 1H), 8.19 (dd, J = 5.8, 2.7 Hz, 1H), 7.95 (ddd, J = 9.3, 4.8, 2.7 Hz, |

-continued

| Compound Name | Compound No. | $^1$H NMR |
|---|---|---|
| | | 1H), 7.55 (t, J = 9.1 Hz, 1H), 3.68 (s, 3H), 3.52 (s, 1H), 3.12 (t, J = 12.0 Hz, 4H), 2.29 (s, 3H) |
| 5-chloro-N-(3-cyano-4-fluoro-phenyl)-4-[2-[(3-ethynyloxetan-3-yl)amino]-2-oxo-acetyl]-1,3-dimethyl-pyrrole-2-carboxamide | 40 | $^1$H NMR (300 MHz, DMSO-$d_6$) δ 10.70 (s, 1H), 9.84 (s, 1H), 8.21 (dd, J = 5.8, 2.7 Hz, 1H), 7.97 (ddd, J = 9.2, 4.9, 2.7 Hz, 1H), 7.57 (t, J = 9.1 Hz, 1H), 4.75 (d, J = 1.4 Hz, 4H), 3.70 (s, 3H), 3.68 (s, 1H), 2.32 (s, 3H) |
| 5-chloro-N-(3-cyano-4-fluoro-phenyl)-1,3-dimethyl-4-[2-oxo-2-[(3-vinyloxetan-3-yl)amino]acetyl]pyrrole-2-carboxamide | 41 | $^1$H NMR (300 MHz, DMSO-$d_6$) δ 10.69 (s, 1H), 9.52 (s, 1H), 8.22 (dd, J = 5.8, 2.6 Hz, 1H), 7.98 (ddd, J = 9.2, 4.9, 2.7 Hz, 1H), 7.57 (t, J = 9.1 Hz, 1H), 6.31 (dd, J= 17.2, 10.5 Hz, 1H), 5.38-5.17 (m, 2H), 4.77 (d, J = 6.6 Hz, 2H), 4.60 (d, J = 6.6 Hz, 2H), 3.71 (s, 3H), 2.33 (s, 3H) |
| N-(3-cyano-4-fluoro-phenyl)-1,3,5-trimethyl-4-[2-oxo-2-[[(1R)-1-(trifluoromethyl)prop-2-ynyl]amino]acetyl]pyrrole-2-carboxamide | 42a | $^1$H NMR (300 MHz, DMSO-$d_6$) δ 10.58 (s, 1H), 10.08 (d, J = 8.8 Hz, 1H), 8.22 (dd, J = 5.8, 2.7 Hz, 1H), 8.01-7.95 (m, 1H), 7.55 (t, J = 9.1 Hz, 1H), 5.99-5.58 (m, 1H), 3.81 (d, J = 2.5 Hz, 1H), 3.61 (s, 3H), 2.42 (s, 3H), 2.24 (s, 3H) |
| N-(3-cyano-4-fluoro-phenyl)-1,3,5-trimethyl-4-[2-oxo-2-[[(1S)-1-(trifluoromethyl)prop-2-ynyl]amino]acetyl]pyrrole-2-carboxamide | 42b | $^1$H NMR (300 MHz, DMSO-$d_6$) δ 10.58 (s, 1H), 10.08 (d, J = 8.8 Hz, 1H), 8.22 (dd, J = 5.8, 2.7 Hz, 1H), 8.01-7.95 (m, 1H), 7.55 (t, J = 9.1 Hz, 1H), 5.99-5.58 (m, 1H), 3.81 (d, J = 2.5 Hz, 1H), 3.61 (s, 3H), 2.42 (s, 3H), 2.24 (s, 3H) |
| N-(3-cyano-4-fluoro-phenyl)-4-[2-[[3-(2-cyclopropylethynyl)oxetan-3-yl]amino]-2-oxo-acetyl]-1,3,5-trimethyl-pyrrole-2-carboxamide | 43 | $^1$H NMR (300 MHz, DMSO-$d_6$) δ 10.54 (s, 1H), 9.65 (s, 1H), 8.24-8.21 (m, 1H), 8.00-7.95 (m, 1H), 7.55 (t, J = 9, 1H), 4.69 (s, 4H), 3.60 (s, 3H), 2.27 (s, 3H), 2.08 (s, 3H), 1.42-1.33 (m, 1H), 0.84-0.80 (m 2H), 0.62-0.59 (m, 2H) |
| 5-chloro-N-(3-cyano-4-fluoro-phenyl)-4-[2-[(3,3-difluoro-1-vinyl-cyclobutyl)amino]-2-oxo-acetyl]-1,3-dimethyl-pyrrole-2-carboxamide | 44 | $^1$H NMR (300 MHz, DMSO-$d_6$) δ 10.68 (s, 1H), 9.37 (s, 1H), 8.21 (dd, J = 5.8, 2.6 Hz, 1H), 8.04-7.90 (m, 1H), 7.57 (t, J = 9.2 Hz, 1H), 6.12 (dd, J = 17.2, 10.4 Hz, 1H), 5.34-5.01 (m, 2H), 3.70 (s, 3H), 3.00 (dt, J = 18.0, 13.1 Hz, 4H), 2.31 (s, 3H) |
| 3-chloro-N-(3-cyano-4-fluoro-phenyl)-4-[2-[(3-ethynyloxetan-3-yl)amino]-2-oxo-acetyl]-1,5-dimethyl-pyrrole-2-carboxamide | 45 | $^1$H NMR (300 MHz, DMSO-$d_6$) δ 10.77 (s, 1H), 9.80 (s, 1H), 8.22 (dd, J = 5.7, 2.7 Hz, 1H), 8.05-7.91 (m, 1H), 7.56 (t, J = 9.2 Hz, 1H), 4.74 (s, 4H), 3.67 (s, 3H), 3.66 (s, 1H), 2.48 (s, 3H) |
| 3-chloro-N-(3-cyano-4-fluoro-phenyl)-1,5-dimethyl-4-[2-oxo-2-[(3-vinyloxetan-3-yl)amino]acetyl]pyrrole-2-carboxamide | 46 | $^1$H NMR (400 MHz, DMSO-$d_6$) δ 10.75 (s, 1H), 9.47 (s, 1H), 8.21 (dd, J = 5.8, 2.7 Hz, 1H), 7.98 (ddd, J = 9.2, 4.8, 2.7 Hz, 1H), 7.54 (t, J = 9.1 Hz, 1H), 6.29 (dd, J = 17.3, 10.5 Hz, 1H), 3.65 (s, 3H), 2.47 (s, 3H) |
| N-(3-cyano-4-fluoro-phenyl)-1,3,5-trimethyl-4-[2-oxo-2-[[3-(3,3,3-trifluoroprop-1-ynyl)oxetan-3-yl]amino]acetyl]pyrrole-2-carboxamide | 47 | $^1$H NMR (400 MHz, DMSO-$d_6$) δ 10.59 (s, 1H), 8.22(dd, J = 5.6, 2.8 Hz, 1H), 8.00-7.96 (m, 1H), 7.56 (t, J = 8.8 Hz, 1H), 6.37-6.31 (m, 1H), 4.80-4.76 (m, 4H), 3.63 (s, 3H), 2.39 (s, 3H), 2.20 (s, 3H) |
| N-(3-cyano-4-fluoro-phenyl)-1,3,5-trimethyl-4-[2-[[3-(3-methylbut-1-ynyl)oxetan-3-yl]amino]-2-oxo-acetyl]pyrrole-2-carboxamide | 48 | $^1$H NMR (300 MHz, DMSO-$d_6$) δ 10.55 (s, 1H), 9.67 (s, 1H), 8.22 (dd, J = 5.8, 2.7 Hz, 1H), 8.00-7.94 (m, 1H), 7.55 (t, J = |

-continued

| Compound Name | Compound No. | $^1$H NMR |
|---|---|---|
| | | 9.2 Hz, 1H), 4.70 (s, 4H), 3.61 (s, 3H), 2.69-2.59 (m, 1H), 2.28 (s, 3H), 2.08 (s, 3H), 1.13 (d, J = 6.9 Hz, 6H) |
| 4-[2-[(1-ethynyl-3-hydroxy-cyclobutyl)amino]-2-oxo-acetyl]-N-[4-fluoro-3-(trifluoromethyl)phenyl]-1,3,5-trimethyl-pyrrole-2-carboxamide | 49 | $^1$H NMR (300 MHz, DMSO-$d_6$) δ 10.52 (s, 1H), 9.31 (s, 1H), 8.22 (dd, J = 6.5, 2.6 Hz, 1H), 7.97 (dt, J = 7.9, 3.8 Hz, 1H), 7.52 (t, J = 9.8 Hz, 1H), 5.34 (s, 1H), 4.15 (s, 1H), 3.60 (s, 3H), 3.26 (s, 1H), 2.78 (ddd, J = 9.5, 6.9, 2.8 Hz, 2H), 2.42 (s, 3H), 2.28 (s, 3H), 2.17 (t, J = 10.0 Hz, 2H) |
| N-(3-cyano-4-fluoro-phenyl)-1,3,5-trimethyl-4-[2-oxo-2-[(3-prop-1-ynyloxetan-3-yl)amino]acetyl]pyrrole-2-carboxamide | 50 | $^1$H NMR (400 MHz, DMSO-$d_6$) δ 10.54 (s, 1H), 9.68 (s, 1H), 8.21(dd, J = 5.6, 2.4 Hz, 1H), 7.99-7.95 (m, 1H), 7.55 (t, J = 9.2 Hz, 1H), 4.70 (s, 4H), 3.60(s, 3H), 2.41 (s, 3H), 2.27 (s, 3H), 1.86 (s, 3H) |
| 3-chloro-N-(3-cyano-4-fluoro-phenyl)-4-[2-[(3,3-difluoro-1-vinyl-cyclobutyl)amino]-2-oxo-acetyl]-1,5-dimethyl-pyrrole-2-carboxamide | 51 | $^1$H NMR (400 MHz, DMSO-$d_6$) δ 10.75 (s, 1H), 9.32 (s, 1H), 8.20 (dd, J = 5.8, 2.7 Hz, 1H), 7.97 (ddd, J = 9.2, 4.9, 2.7 Hz, 1H), 7.54 (t, J = 9.1 Hz, 1H), 6.09 (dd, J = 17.2, 10.4 Hz, 1H), 5.23 (dd, J = 17.1, 0.9 Hz, 1H), 5.13 (dd, J = 10.5, 0.9 Hz, 1H), 3.64 (s, 3H), 2.97 (dq, J = 46.6, 13.5 Hz, 4H), 2.46 (s, 3H) |
| 3-chloro-N-(3-cyano-4-fluoro-phenyl)-4-[2-[(1-ethynyl-3,3-difluoro-cyclobutyl)amino]-2-oxo-acetyl]-1,5-dimethyl-pyrrole-2-carboxamide | 52 | $^1$H NMR (300 MHz, DMSO-$d_6$) δ 10.74 (s, 1H), 9.63 (s, 1H), 8.21 (dd, J = 5.8, 2.7 Hz, 1H), 7.98 (ddd, J = 9.2, 4.9, 2.7 Hz, 1H), 7.55 (t, J = 9.1 Hz, 1H), 3.66 (s, 3H), 3.50 (s, 1H), 3.14 (t, J = 12.1 Hz, 4H), 2.47 (s, 3H) |
| N-(3-cyano-4-fluoro-phenyl)-4-[2-[(3,3-difluoro-1-vinyl-cyclobutyl)amino]-2-oxo-acetyl]-1,3,5-trimethyl-pyrrole-2-carboxamide | 53 | $^1$H NMR (400 MHz, DMSO-$d_6$) δ 10.52 (s, 1H), 9.27 (s, 1H), 8.20 (dd, J = 5.8, 2.7 Hz, 1H), 7.96 (ddd, J = 9.2, 4.9, 2.7 Hz, 1H), 7.53 (t, J = 9.1 Hz, 1H), 6.09 (dd, J = 17.2, 10.5 Hz, 1H), 5.25 (dd, J = 17.2, 0.9 Hz, 1H), 5.13 (dd, J = 10.4, 0.9 Hz, 1H), 3.59 (s, 3H), 3.10-2.80 (m, 4H), 2.41 (s, 3H), 2.25 (s, 3H) |
| N-(3-cyano-4-fluoro-phenyl)-4-[2-[(3-ethynyloxetan-3-yl)amino]-2-oxo-acetyl]-3-fluoro-1,5-dimethyl-pyrrole-2-carboxamide | 55 | $^1$H NMR (400 MHz, DMSO-$d_6$) δ 10.44 (s, 1H), 9.82 (s, 1H), 8.17 (dd, J = 5.8, 2.7 Hz, 1H), 7.97 (ddd, J = 9.3, 4.9, 2.7 Hz, 1H), 7.54 (t, J = 9.1 Hz, 1H), 4.78 C 4.68 (m, 4H), 3.73 (s, 3H), 3.66 (s, 1H), 2.52 (s, 3H) |
| N-(3-cyano-4-fluoro-phenyl)-4-[2-[(1-ethynyl-3,3-difluoro-cyclobutyl)amino]-2-oxo-acetyl]-3-fluoro-1,5-dimethyl-pyrrole-2-carboxamide | 56 | $^1$H NMR (400 MHz, DMSO-d6) δ 10.45 (s, 1H), 9.67 (s, 1H), 8.17 (dd, J = 5.8, 2.7 Hz, 1H), 7.96 (ddd, J = 9.2, 4.9, 2.7 Hz, 1H), 7.54 (t, J = 9.1 Hz, 1H), 3.72 (s, 3H), 3.52 (s, 1H), 3.18 C 3.04 (m, 4H), 2.50 (s, 3H) |
| N-(3-cyano-4-fluoro-phenyl)-1,3,5-trimethyl-4-[2-oxo-2-[[1R)-1-(oxetan-3-yl)prop-2-ynyl]amino]acetyl]pyrrole-2-carboxamide | 57 | $^1$H NMR (300 MHz, DMSO-$d_6$) δ 10.55 (s, 1H), 9.27 (d, J = 8.1 Hz, 1H), 8.22 (dd, J = 5.8, 2.7 Hz, 1H), 7.98 (ddd, J = 9.2, 4.9, 2.7 Hz, 1H), 7.55 (t, J = 9.1 Hz, 1H), 4.96 (td, J = 8.0, 2.4 Hz, 1H), 4.63 (ddd, J = 9.5, 7.8, 6.3 Hz, 2H), 4.47 (t, J = 6.2 Hz, 1H), 4.36 (t, J = 6.2 Hz, 1H), 3.61 (s, 3 H), 3.37 (d, J = 2.3 Hz, 1H), 3.30-3.21 (m, 1H), 2.41 (s, 3H), 2.25 (s, 3H) |

-continued

| Compound Name | Compound No. | $^1$H NMR |
|---|---|---|
| N-(3-cyano-4-fluoro-phenyl)-1,3,5-trimethyl-4-[2-oxo-2-[[(1S)-1-(oxetan-3-yl)prop-2-ynyl]amino]acetyl]pyrrole-2-carboxamide | 58 | $^1$H NMR (300 MHz, DMSO-$d_6$) δ 10.54 (s, 1H), 9.27 (d, J = 8.1 Hz, 1H), 8.21 (dd, J = 5.8, 2.7 Hz, 1H), 8.05-7.87 (m, 1H), 7.55 (t, J = 9.1 Hz, 1H), 5.03-4.88 (m, 1H), 4.71-4.55 (m, 2H), 4.47 (t, J = 6.3 Hz, 1H), 4.36 (t, J = 6.2 Hz, 1H), 3.61 (s, 3H), 3.37 (d, J = 2.3 Hz, 1H), 3.30-3.22 (m, 1H), 2.41 (s, 3H), 2.25 (s, 3H) |
| 5-chloro-N-(3-cyano-4-fluoro-phenyl)-4-[2-[(1-ethynyl-3-hydroxy-cyclobutyl)amino]-2-oxo-acetyl]-1,3-dimethyl-pyrrole-2-carboxamide | 59 | $^1$H NMR (300 MHz, DMSO-$d_6$) δ 10.68 (s, 1H), 9.37 (s, 1H), 8.21 (dd, J = 5.8, 2.7 Hz, 1H), 7.98 (ddd, J = 9.2, 4.9, 2.8 Hz, 1H), 7.57 (t, J = 9.1 Hz, 1H), 5.34 (d, J = 6.8 Hz, 1H), 4.15 (q, J = 7.3 Hz, 1H), 3.70 (s, 3H), 3.26 (s, 1H), 2.84 C 2.72 (m, 2H), 2.31 (s, 3H), 2.21 (s, 2H) |
| 3-chloro-N-(3-cyano-4-fluoro-phenyl)-4-[2-[(1-ethynyl-3-hydroxy-cyclobutyl)amino]-2-oxo-acetyl]-1,5-dimethyl-pyrrole-2-carboxamide | 60 | $^1$H NMR (300 MHz, DMSO-$d_6$) δ 10.75 (s, 1H), 9.34 (s, 1H), 8.23 (dd, J = 5.8, 2.7 Hz, 1H), 8.00 (ddd, J = 9.2, 4.9, 2.7 Hz, 1H), 7.56 (t, J = 9.1 Hz, 1H), 5.32 (d, J = 6.8 Hz, 1H), 4.14 (q, J = 7.2 Hz, 1H), 3.66 (s, 3H), 3.25(s, 1H), 2.83 C 2.73 (m, 2H), 2.47 (s, 3H), 2.21 (s, 2H) |
| N-(3-cyano-4-fluoro-phenyl)-1,3,5-trimethyl-4-[2-oxo-2-[[(1R)-1-(2-hydroxyethyl)prop-2-ynyl]amino]acetyl]pyrrole-2-carboxamide | 61a | $^1$H NMR (300 MHz, DMSO-$d_6$) δ 10.55 (s, 1H), 9.12 (d, J = 8.2 Hz, 1H), 8.22 (dd, J = 5.8, 2.7 Hz, 1H), 8.03-7.92 (m, 1H), 7.55 (t, J = 9.1 Hz, 1H), 4.77 (d, J = 6.1 Hz, 1H), 4.63 (t, J = 4.9 Hz, 1H), 3.60 (s, 3H), 3.53 (q, J = 5.9 Hz, 2H), 3.25 (d, J = 2.3 Hz, 1H), 2.42 (s, 3H), 2.26 (s, 3H), 1.82 (q, J = 6.6 Hz, 2H) |
| N-(3-cyano-4-fluoro-phenyl)-1,3,5-trimethyl-4-[2-oxo-2-[[(1S)-1-(2-hydroxyethyl)prop-2-ynyl]amino]acetyl]pyrrole-2-carboxamide | 61b | $^1$H NMR (300 MHz, DMSO-$d_6$) δ 10.55 (s, 1H), 9.12 (d, J = 8.2 Hz, 1H), 8.22 (dd, J = 5.8, 2.7 Hz, 1H), 7.98 (ddd, J = 9.3, 4.9, 2.7 Hz, 1H), 7.55 (t, J = 9.1 Hz, 1H), 4.77 (d, J = 7.1 Hz, 1H), 4.63 (t, J = 4.9 Hz, 1H), 3.60 (s, 3H), 3.53 (q, J = 5.8 Hz, 2H), 3.25 (d, J = 2.3 Hz, 1H), 2.42 (s, 3H), 2.26 (s, 3H), 1.86-1.78 (m, 2H) |
| N-(3-cyano-4-fluoro-phenyl)-4-[2-[[3-hydroxy-1-(3,3,3-trifluoroprop-1-ynyl)cyclobutyl]amino]-2-oxo-acetyl]-1,3,5-trimethyl-pyrrole-2-carboxamide | 62 | $^1$H NMR (300 MHz, Methanol-$d_4$) δ 8.16 (dd, J = 5.7, 2.7 Hz, 1H), 7.93 (ddd, J = 9.2, 4.7, 2.8 Hz, 1H), 7.39 (t, J = 9.0 Hz, 1H), 4.37 (t, J = 7.5 Hz, 1H), 3.69 (s, 3H), 3.05 (td, J = 6.9, 3.5 Hz, 2H), 2.49 (s, 3H), 2.37 (s, 5H) |
| N-(3-cyano-4-fluoro-phenyl)-1,3,5-trimethyl-4-[2-oxo-2-[[(1R)-1-cyclopropyl-1-(hydroxymethyl)prop-2-ynyl]amino]acetyl]pyrrole-2-carboxamide | 63a | $^1$H NMR (300 MHz, DMSO-$d_6$) δ 10.52 (s, 1H), 8.53 (s, 1H), 8.21 (dd, J = 5.8, 2.7 Hz, 1H), 8.03 C 7.91 (m, 1H), 7.54 (t, J = 9.1 Hz, 1H), 5.17 (t, J = 6.0 Hz, 1H), 3.94 (dd, J = 10.5, 6.4 Hz, 1H), 3.68 C 3.58 (m, 1H), 3.59 (s, 3H), 3.20 (s, 1H), 2.43 (s, 3H), 2.28 (s, 3H), 1.41 C 1.31 (m, 1H), 0.70-0.60 (m, 1H), 0.50 C 0.41 (m, 3H) |
| N-(3-cyano-4-fluoro-phenyl)-1,3,5-trimethyl-4-[2-oxo-2-[[(1S)-1-cyclopropyl-1-(hydroxymethyl)prop-2-ynyl]amino]acetyl]pyrrole-2-carboxamide | 63b | $^1$H NMR (300 MHz, DMSO-$d_6$) δ 10.52 (s, 1H), 8.53 (s, 1H), 8.21 (dd, J = 5.8, 2.7 Hz, 1H), 8.03 C 7.91 (m, 1H), 7.54 (t, J = 9.1 Hz, 1H), 5.17 (t, J = 6.0 Hz, 1H), 3.94 (dd, J = 10.5, 6.4 Hz, 1H), 3.68 C 3.58 (m, 1H), 3.59 (s, 3H), 3.20 (s, 1H), 2.43 (s, |

-continued

| Compound Name | Compound No. | $^1$H NMR |
|---|---|---|
| | | 3H), 2.28 (s, 3H), 1.41 C 1.31 (m, 1H), 0.70-0.60 (m, 1H), 0.50 C 0.41 (m, 3H) |
| N-(3-cyano-4-fluoro-phenyl)-1,3,5-trimethyl-4-[2-oxo-2-[[(1R)-1-(hydroxymethyl)-1-methyl-prop-2-ynyl]amino]acetyl]pyrrole-2-carboxamide | 64a | $^1$H NMR (300 MHz, DMSO-$d_6$) δ 10.52 (s, 1H), 8.48 (s, 1H), 8.21 (dd, J = 5.8, 2.6 Hz, 1H), 8.02-7.91 (m, 1H), 7.54 (t, J = 9.1 Hz, 1H), 5.18 (t, J = 6.1 Hz, 1H), 3.69 (dd, J = 10.7, 6.3 Hz, 1H), 3.59 (s, 3H), 3.57-3.50 (m, 1H), 3.21 (s, 1H), 2.42 (s, 3H), 2.27 (s, 3H), 1.50 (s, 3H) |
| N-(3-cyano-4-fluoro-phenyl)-1,3,5-trimethyl-4-[2-oxo-2-[[(1S)-1-(hydroxymethyl)-1-methyl-prop-2-ynyl]amino]acetyl]pyrrole-2-carboxamide | 64b | $^1$H NMR (300 MHz, DMSO-$d_6$) δ 10.52 (s, 1H), 8.48 (s, 1H), 8.21 (dd, J = 5.8, 2.7 Hz, 1H), 8.05-7.90 (m, 1H), 7.54 (t, J = 9.1 Hz, 1H), 5.18 (t, J = 6.1 Hz, 1H), 3.69 (dd, J = 10.6, 6.3 Hz, 1H), 3.59 (s, 3H), 3.57-3.52 (m, 1H), 3.21 (s, 1H), 2.42 (s, 3H), 2.27 (s, 3H), 1.50 (s, 3H) |
| N-[4-fluoro-3-(trifluoromethyl)phenyl]-1,3,5-trimethyl-4-[2-oxo-2-[[(1R)-1-cyclopropyl-1-(hydroxymethyl)prop-2-ynyl]amino]acetyl]pyrrole-2-carboxamide | 65a | $^1$H NMR (400 MHz, DMSO-$d_6$) δ 10.51 (s, 1H), 8.53 (s, 1H), 8.23 (dd, J = 6.6, 2.7 Hz, 1H), 8.01-7.93 (m, 1H), 7.53 (t, J = 9.8 Hz, 1H), 5.18 (t, J = 6.1 Hz, 1H), 3.95 (dd, J = 10.6, 6.4 Hz, 1H), 3.65-3.55 (m, 4H), 3.21 (s, 1H), 2.44 (s, 3H), 2.30 (s, 3H), 1.37 (ddd, J = 13.6, 8.0, 5.4 Hz, 1H), 0.64 (q, J = 4.8 Hz, 1H), 0.46 (ddd, J = 9.0, 6.4, 3.2 Hz, 3H) |
| N-[4-fluoro-3-(trifluoromethyl)phenyl]-1,3,5-trimethyl-4-[2-oxo-2-[[(1S)-1-cyclopropyl-1-(hydroxymethyl)prop-2-ynyl]amino]acetyl]pyrrole-2-carboxamide | 65b | $^1$H NMR (400 MHz, DMSO-$d_6$) δ 10.51 (s, 1H), 8.53 (s, 1H), 8.23 (dd, J = 6.6, 2.7 Hz, 1H), 8.01-7.93 (m, 1H), 7.53 (t, J = 9.8 Hz, 1H), 5.18 (t, J = 6.1 Hz, 1H), 3.95 (dd, J = 10.6, 6.4 Hz, 1H), 3.65-3.55 (m, 4H), 3.21 (s, 1H), 2.44 (s, 3H), 2.30 (s, 3H), 1.37 (ddd, J = 13.6, 8.0, 5.4 Hz, 1H), 0.64 (q, J = 4.8 Hz, 1H), 0.46 (ddd, J = 9.0, 6.4, 3.2 Hz, 3H) |
| N-(3-bromo-2-fluoro-4-pyridyl)-4-[2-[(3-ethynyloxetan-3-yl)amino]-2-oxo-acetyl]-1,3,5-trimethyl-pyrrole-2-carboxamide | 67 | $^1$H NMR (400 MHz, DMSO-$d_6$) δ 9.97 (s, 1H), 9.79 (s, 1H), 8.19 (d, J = 5.5 Hz, 1H), 7.96 (d, J = 5.5 Hz, 1H), 4.79-4.69 (m, 4H), 3.67 (d, J = 2.7 Hz, 4H), 2.43 (d, J = 5.9 Hz, 6H) |
| N-(3-bromo-2-fluoro-4-pyridyl)-4-[2-[(1-ethynyl-3,3-difluoro-cyclobutyl)amino]-2-oxo-acetyl]-1,3,5-trimethyl-pyrrole-2-carboxamide | 68 | $^1$H NMR (400 MHz, DMSO-$d_6$) δ 9.97 (s, 1H), 9.64 (s, 1H), 8.19 (dd, J = 5.6, 2.3 Hz, 1H), 7.95 (dd, J = 5.5, 2.3 Hz, 1H), 3.67 (d, J = 2.3 Hz, 3H), 3.54 (d, J = 2.3 Hz, 1H), 3.14 (t, J = 12.3 Hz, 4H), 2.42 (dd, J = 7.3, 2.4 Hz, 6H) |
| N-[4-fluoro-3-(trifluoromethyl)phenyl]-1,3,5-trimethyl-4-[2-oxo-2-[[(1R)-1-(hydroxymethyl)-1-methyl-allyl]amino]acetyl]pyrrole-2-carboxamide | 69a | $^1$H NMR (300 MHz, DMSO-$d_6$) δ 10.49 (s, 1H), 8.21 (dd, J = 6.6, 2.6 Hz, 1H), 8.15 (s, 1H), 8.01-7.91 (m, 1H), 7.52 (t, J = 9.8 Hz, 1H), 6.01 (dd, J = 17.5, 10.8 Hz, 1H), 5.22-5.04 (m, 2H), 4.95 (t, J = 5.9 Hz, 1H), 3.59 (s, 3H), 3.56-3.51 (m, 1H), 3.46 (dd, J = 10.8, 5.9 Hz, 1H), 2.41 (s, 3H), 2.26 (s, 3H), 1.39 (s, 3H) |
| N-[4-fluoro-3-(trifluoromethyl)phenyl]-1,3,5-trimethyl-4-[2-oxo-2-[[(1S)-1-(hydroxymethyl)-1-methyl-allyl]amino]acetyl]pyrrole-2-carboxamide | 69b | $^1$H NMR (300 MHz, DMSO-$d_6$) δ 10.49 (s, 1H), 8.21 (dd, J = 6.6, 2.7 Hz, 1H), 8.15 (s, 1H), 8.00-7.91 (m, 1H), 7.52 (t, J = 9.8 Hz, 1H), 6.01 (dd, J = 17.6, 10.8 Hz, 1H), 5.22-5.03 (m, 2H), 4.95 (t, J = 5.9 Hz, 1H), 3.59 (s, 3H), |

-continued

| Compound Name | Compound No. | $^1$H NMR |
|---|---|---|
| | | 3.55-3.42 (m, 2H), 2.41 (s, 3H), 2.26 (s, 3H), 1.39 (s, 3H) |
| N-(3-cyano-4-fluoro-phenyl)-1,3,5-trimethyl-4-[2-[[1-methyl-1-(1-methylpyrazol-4-yl)ethyl]amino]-2-oxo-acetyl]pyrrole-2-carboxamide | 70 | $^1$H NMR (400 MHz, $CDCl_3$) δ 8.02 (dd, J = 2.7, 5.4 Hz, 1H), 7.76-7.61 (m, 2H), 7.49 (s, 1H), 7.41 (s, 1H), 7.20 (t, J = 8.6 Hz, 1H), 7.00-6.92 (m, 1H), 3.87 (s, 3H), 3.69 (s, 3H), 2.34 (d, J = 8.3 Hz, 6H), 1.78 (s, 6H), 1.25 (s, 1H) |
| N-(3-cyano-4-fluoro-phenyl)-1,3,5-trimethyl-4-[2-oxo-2-[[(1R)-1-(hydroxymethyl)-1-(trifluoromethyl)prop-2-ynyl]amino]acetyl]pyrrole-2-carboxamide | 71a | $^1$H NMR (400 MHz, $CDCl_3$) δ 8.02 (dd, J = 5.2, 2.8 Hz, 1H), 7.75-7.71(m,, 1H), 7.58 (s, 1H), 7.51 (s, 1H), 7.24-7.20 (m, 1H), 4.39-4.34(m, 1H), 4.15-4.12 (m, 1H), 3.72 (s, 3H), 3.71-3.68 (m, 1H), 2.72 (s, 1H), 2.40 (d, J = 7.2 Hz, 6H). |
| N-(3-cyano-4-fluoro-phenyl)-1,3,5-trimethyl-4-[2-oxo-2-[[(1S)-1-(hydroxymethyl)-1-(trifluoromethyl)prop-2-ynyl]amino]acetyl]pyrrole-2-carboxamide | 71b | $^1$H NMR (400 MHz, $CDCl_3$) δ 8.02 (dd, J = 5.2, 2.4 Hz, 1H), 7.75-7.71 (m, 1H), 7.60 (s, 1H), 7.51 (s, 1H), 7.24-7.20 (m, 1H), 4.36 (d, J = 12.4 Hz, 1H), 4.16 (d, J = 12.8 Hz, 1H), 3.72 (s, 3H), 3.37-3.68(m, 1H), 2.74 (s, 1H), 2.40 (d, J = 7.2 Hz, 6H) |
| N-(3-cyano-4-fluoro-phenyl)-1,3,5-trimethyl-4-[2-oxo-2-[[(1R)-1-(hydroxymethyl)-1-methyl-allyl]amino]acetyl]pyrrole-2-carboxamide | 72a | $^1$H NMR (300 MHz, DMSO-$d_6$) δ 10.51 (s, 1H), 8.25-8.19 (m, 1H), 8.15 (s, 1H), 7.98 (dddd, J = 9.2, 4.8, 2.7, 1.5 Hz, 1H), 7.55 (t, J = 9.1 Hz, 1H), 6.02 (dd, J = 17.6, 10.8 Hz, 1H), 5.22-5.06 (m, 2H), 4.95 (t, J = 5.8 Hz, 1H), 3.60 (s, 3H), 3.57-3.43 (m, 2H), 2.42 (s, 3H), 2.27 (s, 3H), 1.39 (s, 3H). |
| N-(3-cyano-4-fluoro-phenyl)-1,3,5-trimethyl-4-[2-oxo-2-[[(1S)-1-(hydroxymethyl)-1-methyl-allyl]amino]acetyl]pyrrole-2-carboxamide | 72b | $^1$H NMR (300 MHz, DMSO-$d_6$) δ 10.51 (s, 1H), 8.25-8.11 (m, 2H), 7.98 (ddd, J = 9.2, 4.8, 2.7 Hz, 1H), 7.55 (t, J = 9.1 Hz, 1H), 6.02 (dd, J = 17.6, 10.8 Hz, 1H), 5.23-5.05 (m, 2H), 4.95 (t, J = 5.9 Hz, 1H), 3.65-3.41 (m, 5H), 2.42 (s, 3H), 2.27 (s, 3H), 1.39 (s, 3H) |
| N-(3-cyano-4-fluoro-phenyl)-1,3,5-trimethyl-4-[2-oxo-2-[[(1R)-1-(hydroxymethyl)-1-(trifluoromethyl)allyl]amino]acetyl]pyrrole-2-carboxamide | 74a | $^1$H NMR (300 MHz, $CDCl_3$) δ 8.04 (dd, J = 5.4, 2.7 Hz, 1H), 7.79-7.73 (m, 1H), 7.67 (s, 1H), 7.35 (s, 1H), 7.25 (dd, J = 12.0, 3.6 Hz, 1H), 6.03 (dd, J = 17.4, 10.8 Hz, 1H), 5.62 C 5.55 (m, 2H), 4.47 (s, 1H), 4.23 (d, J = 12.6 Hz, 1H), 3.96 (d, J = 13.2 Hz, 1H), 3.75 (s, 3H), 2.43 (d, J = 6.6 Hz, 6H) |
| N-(3-cyano-4-fluoro-phenyl)-1,3,5-trimethyl-4-[2-oxo-2-[[(1S)-1-(hydroxymethyl)-1-(trifluoromethyl)allyl]amino]acctyl]pyrrole-2-carboxamide | 74b | $^1$H NMR (400 MHz, $CDCl_3$) δ 8.02 (dd, J = 5.2, 2.8 Hz, 1H), 7.76-7.72 (m, 1H), 7.65 (s, 1H), 7.33 (s, 1H), 7.23 (dd, J = 15.6, 7.2 Hz, 1H), 6.00 (dd, J = 17.6, 10.8 Hz, 1H), 5.59 C 5.53 (m, 2H), 4.46 (t, J = 7.6 Hz, 1H), 4.21 (dd, J = 12.8, 8.4 Hz, 1H), 3.94 (dd, J = 12.8, 6.4 Hz, 1H), 3.73 (s, 3H), 2.41 (d, J = 8.8 Hz, 6H) |
| N-[4-fluoro-3-(trifluoromethyl)phenyl]-1,3,5-trimethyl-4-[2-oxo-2-[[(1R)-1-(hydroxymethyl)-1-(trifluoromethyl)prop-2-ynyl]amino]acetyl]pyrrole-2-carboxamide | 75a | $^1$H NMR (400 MHz, $CDCl_3$) δ 7.88 (dd, J = 6.0, 2.4 Hz, 1H), 7.76-7.72 (m, 1H), 7.51 (d, J = 6.4 Hz, 2H), 7.24 (t, J = 9.2 Hz, 1H), 4.38 (d, J = 12.4 Hz, 1H), 4.15 (d, J = 11.6 Hz, 1H), 3.73 (s, 3H), 2.71 (s, 1H), 2.41 (d, J = 3.6 Hz, 6H) |
| N-[4-fluoro-3-(trifluoromethyl)phenyl]-1,3,5-trimethyl-4-[2-oxo-2-[[(1S)-1- | 75b | $^1$H NMR (400 MHz, $CDCl_3$) δ 7.88 (dd, J = 6.4, 2.8 Hz, 1H), |

-continued

| Compound Name | Compound No. | $^1$H NMR |
|---|---|---|
| (hydroxymethyl)-1-(trifluoromethyl)prop-2-ynyl]amino]acetyl]pyrrole-2-carboxamide | | 7.76-7.72 (m, 1H), 7.50 (d, J = 5.2 Hz, 2H), 7.21 (t, J = 9.6 Hz, 1H), 4.37 (d, J = 12.4 Hz, 1H), 4.15 (d, J = 12.4 Hz, 1H), 3.73 (s, 3H), 2.71 (s, 1H), 2.40 (d, J = 4.8 Hz, 6H) |
| N-(3-cyano-4-fluoro-phenyl)-4-[2-[[3-(3-hydroxyprop-1-ynyl)oxetan-3-yl]amino]-2-oxo-acetyl]-1,3,5-trimethyl-pyrrole-2-carboxamide | 76 | $^1$H NMR (400 MHz, DMSO-$d_6$) δ 10.55 (s, 1H), 9.74 (s, 1H), 8.22 (dd, J = 5.8, 2.7 Hz, 1H), 7.98 (ddd, J = 9.2, 4.8, 2.7 Hz, 1H), 7.55 (t, J = 9.1 Hz, 1H), 5.26 (t, J = 5.9 Hz, 1H), 4.74 (s, 4H), 4.14 (d, J = 5.9 Hz, 2H), 3.61 (s, 3H), 2.43 (s, 3H), 2.28 (s, 3H) |
| N-(3-cyano-4-fluoro-phenyl)-1,3,5-trimethyl-4-[2-oxo-2-[[(1R)-1-methyl-1-(trifluoromethyl)prop-2-ynyl]amino]acetyl]pyrrole-2-carboxamide | 79a | $^1$H NMR (300 MHz, Methanol-$d_4$) δ 8.16 (dd, J = 5.6, 2.7 Hz, 1H), 7.94 (ddd, J = 9.2, 4.8, 2.8 Hz, 1H), 7.39 (t, J = 9.0 Hz, 1H), 3.69 (s, 3H), 3.24 (s, 1H), 2.51 (s, 3H), 2.39 (s, 3H), 1.90 (s, 3H) |
| N-(3-cyano-4-fluoro-phenyl)-1,3,5-trimethyl-4-[2-oxo-2-[[(1S)-1-methyl-1-(trifluoromethyl)prop-2-ynyl]amino]acetyl]pyrrole-2-carboxamide | 79b | $^1$H NMR (300 MHz, Methanol-$d_4$) δ 8.16 (dd, J = 5.7, 2.7 Hz, 1H), 7.94 (ddd, J = 9.2, 4.7, 2.7 Hz, 1H), 7.39 (t, J = 9.0 Hz, 1H), 3.69 (s, 3H), 3.24 (s, 1H), 2.51 (s, 3H), 2.39 (s, 3H), 1.90 (s, 3H) |
| N-[4-fluoro-3-(trifluoromethyl)phenyl]-1,3,5-trimethyl-4-[2-oxo-2-[[(1R)-1-(hydroxymethyl)-1-(trifluoromethyl)allyl]amino]acetyl]pyrrole-2-carboxamide | 80a | $^1$H NMR (400 MHz, $CDCl_3$) δ 7.88 (dd, J = 6.0, 2.4 Hz, 1H), 7.76-7.72 (m, 1H), 7.34 (s, 1H), 7.22 (t, J = 9.2 Hz, 1H), 6.01 (dd, J = 17.6, 10.8 Hz, 1H), 5.60 C 5.54 (m, 2H), 4.23 (d, J = 12.8 Hz, 1H), 3.96 (d, J = 12.8 Hz, 1H), 3.74 (s, 3H), 2.43 (d, J = 3.6 Hz, 6H) |
| N-[4-fluoro-3-(trifluoromethyl)phenyl]-1,3,5-trimethyl-4-[2-oxo-2-[[(1S)-1-(hydroxymethyl)-1-(trifluoromethyl)allyl]amino]acetyl]pyrrole-2-carboxamide | 80b | $^1$H NMR (400 MHz, $CDCl_3$) δ 7.98 (dd, J = 6.0, 2.8 Hz, 1H), 7.76-7.73 (m, 1H), 7.51 (s, 1H), 7.34 (s, 1H), 7.22 (t, J = 9.2 Hz, 1H), 6.01 (dd, J = 17.2, 10.8 Hz, 1H), 5.60 C 5.54 (m, 2H), 4.23 (d, J = 12.8 Hz, 1H), 3.95 (d, J = 13.2 Hz, 1H), 3.73 (s, 3H), 2.42 (d, J = 4.8 Hz, 6H) |
| 5-chloro-N-[3-(difluoromethyl)-4-fluoro-phenyl]-4-[2-[(1-ethynyl-3,3-difluoro-cyclobutyl)amino]-2-oxo-acetyl]-1,3-dimethyl-pyrrole-2-carboxamide | 81 | $^1$H NMR (400 MHz, DMSO-$d_6$) δ 10.59 (s, 1H), 9.69 (s, 1H), 8.20-8.01 (m, 1H), 7.83 (s, 1H), 7.48-7.07 (m, 2H), 3.70 (s, 3H), 3.54 (s, 1H), 3.15 (t, J = 11.9 Hz, 4H), 2.31 (s, 3H) |
| N-[3-(difluoromethyl)-4-fluoro-phenyl]-4-[2-[(1-ethynyl-3,3-difluoro-cyclobutyl)amino]-2-oxo-acetyl]-1,3,5-trimethyl-pyrrole-2-carboxamide | 82 | $^1$H NMR (400 MHz, DMSO-$d_6$) δ 10.45 (s, 1H), 9.62 (s, 1H), 8.08 (dd, J = 6.4, 2.6 Hz, 1H), 7.88-7.79 (m, 1H), 7.41-7.09 (m, 2H), 3.61 (s, 3H), 3.53 (s, 1H), 3.20-3.05 (m, 4H), 2.43 (s, 3H), 2.26 (s, 3H). |
| N-(2-bromo-3-fluoro-4-pyridyl)-4-[2-[(3-ethynyloxetan-3-yl)amino]-2-oxo-acetyl]-1,3,5-trimethyl-pyrrole-2-carboxamide | 83 | $^1$H NMR (300 MHz, DMSO-$d_6$) δ 10.56 (s, 1H), 9.77 (s, 1H), 8.19 (d, J = 5.3 Hz, 1H), 8.05 (t, J = 5.4 Hz, 1H), 4.73 (q, J = 6.6 Hz, 4H), 3.66 (s, 1H) , 3.63 (s, 3H), 2.42 (s, 3H), 2.30 (s, 3H) |
| N-(2-bromo-3-fluoro-4-pyridyl)-4-[2-[(1-ethynyl-3,3-difluoro-cyclobutyl)amino]-2-oxo-acetyl]-1,3,5-trimethyl-pyrrole-2-carboxamide | 84 | $^1$H NMR (300 MHz, DMSO-$d_6$) δ 10.54 (s, 1H), 9.62 (s, 1H), 8.19 (d, J = 5.3 Hz, 1H), 8.05 (t, J = 5.4 Hz, 1H), 3.63 (s, 3H), 3.52 (s, 1H), 3.12(t, J = 12.2 Hz, 4H), 2.42 (s, 3H), 2.30 (s, 3H) |
| N-(3-cyano-4-fluoro-phenyl)-1,3,5-trimethyl-4-[2-[(1-methyl-1-thiazol-2-yl-ethyl)amino]-2-oxo-acetyl]pyrrole-2-carboxamide | 85 | $^1$H NMR (400 MHz, DMSO-$d_6$) δ 10.53 (s, 1H), 9.21 (s, 1H), 8.22 (dd, J = 5.8, 2.7 Hz, 1H), 7.98 (ddd, J = 9.2, 4.8, 2.7 Hz, |

-continued

| Compound Name | Compound No. | $^1$H NMR |
|---|---|---|
| | | 1H), 7.69 (d, J = 3.3 Hz, 1H), 7.62 (d, J = 3.3 Hz, 1H), 7.55 (t, J = 9.2 Hz, 1H), 3.59 (s, 3H), 2.40 (s, 3H), 2.24 (s, 3H), 1.74 (s, 6H) |
| N-(3-cyano-4-fluoro-phenyl)-1,3,5-trimethyl-4-[2-[[1-methyl-1-(2-pyridyl)ethyl]amino]-2-oxo-acetyl]pyrrole-2-carboxamide | 91 | $^1$H NMR (400 MHz, DMSO-$d_6$) δ 10.49 (s, 1H), 8.98 (s, 1H), 8.51 (d, J = 4.0 Hz, 1H), 8.20 (dd, J = 2.7, 5.8 Hz, 1H), 7.97 (ddd, J = 2.6, 4.9, 9.2 Hz, 1H), 7.78 (dt, J = 1.8, 7.8 Hz, 1H), 7.57-7.48 (m, 2H), 7.25 (dd, J = 5.3, 7.0 Hz, 1H), 3.58 (s, 3H), 2.39 (s, 3H), 2.25 (s, 3H), 1.71-1.59 (m, 6H) |
| N-(3-cyano-4-fluoro-phenyl)-1,3,5-trimethyl-4-[2-[[1-methyl-1-(3-pyridyl)ethyl]amino]-2-oxo-acetyl]pyrrole-2-carboxamide | 92 | $^1$H NMR (400 MHz, DMSO-$d_6$) δ 10.49 (s, 1H), 9.00 (s, 1H), 8.66 (d, J = 2.3 Hz, 1H), 8.42 (dd, J = 1.4, 4.7 Hz, 1H), 8.19 (dd, J = 2.6, 5.8 Hz, 1H), 7.96 (ddd, J = 2.8, 4.8, 9.2 Hz, 1H), 7.86-7.71 (m, 1H), 7.53 (t, J = 9.1 Hz, 1H), 7.35 (dd, J = 4.8, 8.0 Hz, 1H), 3.58 (s, 3H), 2.37 (s, 3H), 2.22 (s, 3H), 1.67 (s, 6H) |
| N-(3-cyano-4-fluoro-phenyl)-1,3,5-trimethyl-4-[2-[[1-methyl-1-(4-pyridyl)ethyl]amino]-2-oxo-acetyl]pyrrole-2-carboxamide | 93 | $^1$H NMR (400 MHz, DMSO-$d_6$) δ 10.50 (s, 1H), 9.03 (s, 1H), 8.58-8.42 (m, 2H), 8.20 (dd, J = 2.6, 5.8 Hz, 1H), 8.02-7.89 (m, 1H), 7.53 (t, J = 9.1 Hz, 1H), 7.44-7.30 (m, 2H), 3.58 (s, 3H), 2.39 (s, 2H), 2.24 (s, 3H), 1.63 (s, 6H) |
| N-(3-cyano-4-fluoro-phenyl)-1,3,5-trimethyl-4-[2-oxo-2-[[3-[(3R)-3-hydroxybut-1-ynyl]oxetan-3-yl]amino]acetyl]pyrrole-2-carboxamide | 94a | $^1$H NMR (400 MHz, Methanol-$d_4$) δ 8.14 (t, J = 2.8 Hz, 1H), 7.93-7.89 (m, 1H), 7.36 (t, J = 8.8 Hz, 1H), 4.85-4.84 (m, 4H), 4.54 (q, J = 6.8 Hz, 1H), 3.88 (s, 3H), 2.48 (s, 3H), 2.37(s, 3H), 1.40 (d, J = 6.8 Hz, 3H). |
| N-(3-cyano-4-fluoro-phenyl)-1,3,5-trimethyl-4-[2-oxo-2-[[3-[(3S)-3-hydroxybut-1-ynyl]oxetan-3-yl]amino]acetyl]pyrrole-2-carboxamide | 94b | $^1$H NMR (400 MHz, Methanol-$d_4$) δ 8.14 (t, J = 2.8 Hz, 1H), 7.93-7.89 (m, 1H), 7.36 (t, J = 8.8 Hz, 1H), 4.85-4.84 (m, 4H), 4.54 (q, J = 6.8 Hz, 1H), 3.88 (s, 3H), 2.48 (s, 3H), 2.37(s, 3H), 1.40 (d, J = 6.8 Hz, 3H). |
| N-(3-cyano-4-fluoro-phenyl)-1,3,5-trimethyl-4-[2-oxo-2-[[(1R)-1-methyl-1-(trifluoromethyl)allyl]amino]acetyl]pyrrole-2-carboxamide | 95a | $^1$H NMR (300 MHz, DMSO-$d_6$) δ 10.54 (s, 1H), 9.03 (s, 1H), 8.22 (dd, J = 5.8, 2.7 Hz, 1H), 7.98 (ddd, J = 9.2, 4.9, 2.7 Hz, 1H), 7.55 (t, J = 9.1 Hz, 1H), 6.32 (dd, J = 17.5, 10.9 Hz, 1H), 5.80 C 5.28 (m, 2H), 3.61 (s, 3H), 2.43 (s, 3H), 2.26 (s, 3H), 1.70 (s, 3H). |
| N-(3-cyano-4-fluoro-phenyl)-1,3,5-trimethyl-4-[2-oxo-2-[[(1S)-1-methyl-1-(trifluoromethyl)allyl]amino]acetyl]pyrrole-2-carboxamide | 95b | $^1$H NMR (300 MHz, DMSO-$d_6$) δ 10.54 (s, 1H), 9.03 (s, 1H), 8.22 (dd, J = 5.8, 2.7 Hz, 1H), 7.98 (ddd, J = 9.2, 4.9, 2.7 Hz, 1H), 7.55 (t, J = 9.1 Hz, 1H), 6.32 (dd, J = 17.5, 10.9 Hz, 1H), 5.80 C 5.28 (m, 2H), 3.61 (s, 3H), 2.43 (s, 3H), 2.26 (s, 3H), 1.70 (s, 3H). |
| N-(3-cyano-4-fluoro-phenyl)-1,3,5-trimethyl-4-[2-[[1-methyl-1-(1H-pyrazol-4-yl)ethyl]amino]-2-oxo-acetyl]pyrrole-2-carboxamide | 96 | $^1$H NMR (400 MHz, DMSO-$d_6$) δ 12.57 (br s, 1H), 10.48 (s, 1H), 8.49 (s, 1H), 8.20 (dd, J = 2.6, 5.8 Hz, 1H), 7.96 (ddd, J = 2.8, 4.9, 9.1 Hz, 1H), 7.53 (br t, J = 9.1 Hz, 3H), 3.57 (s, 3H), 2.35-2.32 (m, 2H), 2.32-2.32 (m, 1H), 2.20 (s, 3H), 1.65 (s, 6H) |
| N-[4-fluoro-3-(trifluoromethyl)phenyl]-1,3,5-trimethyl-4-[2-[[1-methyl-1-(1H-pyrazol-4-yl)ethyl]amino]-2-oxo-acetyl]pyrrole-2-carboxamide | 97 | $^1$H NMR (400 MHz, DMSO-$d_6$) δ 12.57 (br s, 1H), 10.46 (s, 1H), 8.49 (s, 1H), 8.20 (dd, J = 2.4, 6.4 Hz, 1H), 8.01-7.90 (m, 1H), |

-continued

| Compound Name | Compound No. | $^1$H NMR |
|---|---|---|
| | | 7.63-7.41 (m, 3H), 3.57 (s, 3H), 2.34 (s, 3H), 2.21 (s, 3H), 1.66 (s, 6H) |
| N-[4-fluoro-3-(trifluoromethyl)phenyl]-1,3,5-trimethyl-4-[2-[[1-methyl-1-(1-methylpyrazol-4-yl)ethyl]amino]-2-oxo-acetyl]pyrrole-2-carboxamide | 98 | $^1$H NMR (400 MHz, DMSO-$d_6$) δ 10.47 (s, 1H), 8.51 (s, 1H), 8.20 (dd, J = 2.6, 6.6 Hz, 1H), 7.98-7.92 (m, 1H), 7.60 (s, 1H), 7.51 (t, J = 9.8 Hz, 1H), 7.38 (d, J = 0.6 Hz, 1H), 3.78 (s, 3H), 3.57 (s, 3H), 2.36-2.33 (m, 3H), 2.21 (s, 3H), 1.63 (s, 6H) |
| N-[4-fluoro-3-(trifluoromethyl)phenyl]-1,3,5-trimethyl-4-[2-[[1-methyl-1-(2-pyridyl)ethyl]amino]-2-oxo-acetyl]pyrrole-2-carboxamide | 99 | $^1$H NMR (400 MHz, DMSO-$d_6$) δ 10.48 (s, 1H), 8.98 (s, 1H), 8.51 (d, J = 3.9 Hz, 1H), 8.21 (br d, J = 3.9 Hz, 1H), 7.99-7.92 (m, 1H), 7.79 (br d, J = 1.6 Hz, 1H), 7.52 (d, J = 8.4 Hz, 2H), 7.25 (br d, J = 1.9 Hz, 1H), 3.59 (s, 3H), 2.39 (s, 3H), 2.25 (s, 3H), 1.67 (s, 6H) |
| N-[4-fluoro-3-(trifluoromethyl)phenyl]-1,3,5-trimethyl-4-[2-[[1-methyl-1-(3-pyridyl)ethyl]amino]-2-oxo-acetyl]pyrrole-2-carboxamide | 100 | $^1$H NMR (400 MHz, DMSO-$d_6$) δ 10.48 (s, 1H), 9.01 (s, 1H), 8.66 (d, J = 2.4 Hz, 1H), 8.43 (dd, J = 1.4, 4.7 Hz, 1H), 8.20 (dd, J = 2.6, 6.6 Hz, 1H), 7.95 (br dd, J = 4.1, 7.6 Hz, 1H), 7.80 (td, J = 1.9, 8.0 Hz, 1H), 7.51 (t, J = 9.8 Hz, 1H), 7.35 (dd, J = 4.8, 8.0 Hz, 1H), 3.58 (s, 3H), 2.38 (s, 3H), 2.23 (s, 3H), 1.68 (s, 6H) |
| N-[4-fluoro-3-(trifluoromethyl)phenyl]-1,3,5-trimethyl-4-[2-[[1-methyl-1-(4-pyridyl)ethyl]amino]-2-oxo-acetyl]pyrrole-2-carboxamide | 101 | $^1$H NMR (400 MHz, DMSO-$d_6$) δ 10.49 (s, 1H), 9.04 (s, 1H), 8.57-8.45 (m, 2H), 8.21 (dd, J = 2.5, 6.6 Hz, 1H), 7.96 (td, J = 3.7, 8.5 Hz, 1H), 7.52 (t, J = 9.8 Hz, 1H), 7.45-7.34 (m, 2H), 3.59 (s, 3H), 2.40 (s, 3H), 2.25 (s, 3H), 1.64 (s, 6H) |
| N-(3-cyano-4-fluoro-phenyl)-4-[2-[[3-[2-(1-hydroxycyclopropyl)ethynyl]oxetan-3-yl]amino]-2-oxo-acetyl]-1,3,5-trimethyl-pyrrole-2-carboxamide | 102 | $^1$H NMR (300 MHz, Methanol-$d_4$) δ 8.16 (dd, J = 5.6, 2.7 Hz, 1H), 7.94 (ddd, J = 9.2, 4.7, 2.7 Hz, 1H), 7.39 (t, J = 9.0 Hz, 1H), 4.86 (s, 4H), 3.69 (s, 3H), 2.51 (s, 3H), 2.39 (s, 3H), 1.01 (t, J = 2.8 Hz, 2H), 0.97 (t, J = 2.8 Hz, 2H). |
| N-[4-fluoro-3-(trifluoromethyl)phenyl]-1,3,5-trimethyl-4-[2-[(1-methyl-1-thiazol-2-yl-ethyl)amino]-2-oxo-acetyl]pyrrole-2-carboxamide | 103 | $^1$H NMR (400 MHz, DMSO-$d_6$) δ 10.49 (s, 1H), 9.17 (s, 1H), 8.21 (dd, J = 2.2, 6.4 Hz, 1H), 8.02-7.89 (m, 1H), 7.68 (d, J = 3.3 Hz, 1H), 7.61 (d, J = 3.3 Hz, 1H), 7.51 (t, J = 9.8 Hz, 1H), 3.59 (s, 3H), 2.39 (s, 3H), 2.24 (s, 3H), 1.74 (s, 6H) |
| [[2-[5-[(3-cyano-4-fluoro-phenyl)carbamoyl]-1,2,4-trimethyl-pyrrol-3-yl]-2-oxo-acetyl]-(3-ethynyloxetan-3-yl)amino]methyl-(2S)-2-amino-3-methyl-butanoate | 105 | $^1$H NMR (400 MHz, DMSO-$d_6$) δ 10.60 (s, 1H), 8.19 (dd, J = 5.7, 2.6 Hz, 1H), 7.99 C 7.91 (m, 1H), 7.54 (t, J = 9.2 Hz, 1H), 5.51 C 5.38 (m, 2H), 4.91 (dd, J = 6.9, 5.2 Hz, 2H), 4.64 (dd, J = 6.3, 2.7 Hz, 2H), 3.65 (d, J = 50.3 Hz, 4H), 3.09 (s, 1H), 2.42 (s, 3H), 2.25 (s, 3H), 1.80 (dd, J = 12.4, 6.1Hz, 1H), 0.83 (d, J = 6.8 Hz, 3H), 0.74 (d, J = 6.8 Hz, 2H). |
| N-(3-cyano-4-fluoro-phenyl)-4-[2-[(4-ethynyltetrahydropyran-4-yl)amino]-2-oxo-acetyl]-1,3,5-trimethyl-pyrrole-2-carboxamide | 107 | $^1$H NMR (400 MHz, DMSO-$d_6$) δ 10.54 (s, 1H), 8.89 (s, 1H), 8.22 (dd, J = 2.7, 5.8 Hz, 1H), 7.98 (ddd, J = 2.8, 4.9, 9.1 Hz, 1H), 7.55 (t, J = 9.1 Hz, 1H), 3.81-3.71 (m, 2H), 3.64 (br s, 1H), 3.60 (s, 4H), 3.43 (s, 1H), |

-continued

| Compound Name | Compound No. | $^1$H NMR |
|---|---|---|
| | | 2.45 (s, 3H), 2.29 (s, 3H), 2.10 (br d, J = 14.4 Hz, 2H), 1.96-1.83 (m, 2H) |
| N-(3-cyano-4-fluoro-phenyl)-4-[2-[(1-ethynylcyclopentyl)amino]-2-oxo-acetyl]-1,3,5-trimethyl-pyrrole-2-carboxamide | 109 | $^1$H NMR (400 MHz, DMSO-$d_6$) δ 10.54 (s, 1H), 8.83 (s, 1H), 8.21 (dd, J = 2.7, 5.8 Hz, 1H), 7.97 (ddd, J = 2.8, 4.8, 9.2 Hz, 1H), 7.54 (t, J = 9.2 Hz, 1H), 3.59 (s, 3H), 3.20 (s, 1H), 2.43 (s, 3H), 2.27 (s, 3H), 2.22-2.12 (m, 2H), 2.06-1.94 (m, 2H), 1.77-1.63 (m, 4H) |
| 4-[2-[[3,3-difluoro-1-(1-methyltriazol-4-yl)cyclobutyl]amino]-2-oxo-acetyl]-N-[4-fluoro-3-(trifluoromethyl)phenyl]-1,3,5-trimethyl-pyrrole-2-carboxamide | 110 | $^1$H NMR (400 MHz, DMSO-$d_6$) δ 10.52 (s, 1H), 9.74 (s, 1H), 8.21 (dd, J = 2.5, 6.5 Hz, 1H), 8.04-7.86 (m, 2H), 7.53 (t, J = 9.8 Hz, 1H), 4.04 (s, 3H), 3.59 (s, 3H), 3.30-3.19 (m, 4H), 2.34 (s, 3H), 2.20 (s, 3H) |
| N-(3-cyano-4-fluoro-phenyl)-4-[2-[[1-(1H-imidazol-2-yl)-1-methyl-ethyl]amino]-2-oxo-acetyl]-1,3,5-trimethyl-pyrrole-2-carboxamide | 131 | $^1$H NMR (400 MHz, DMSO-$d_6$) δ 10.45 (s, 1H), 9.61 (s, 1H), 8.22 (d, J = 2.4 Hz, 1H), 7.72-7.65 (m, 1H), 7.63-7.57 (m, 1H), 3.60 (s, 3H), 3.52 (s, 1H), 3.13 (br t, J = 11.9 Hz, 4H), 2.42 (s, 3H), 2.28-2.22 (m, 3H) |
| N-[4-fluoro-3-(trifluoromethyl)phenyl]-4-[2-[[1-(1H-imidazol-2-yl)-1-methyl-ethyl]amino]-2-oxo-acetyl]-1,3,5-trimethyl-pyrrole-2-carboxamide | 132 | $^1$H NMR (400 MHz, $CDCl_3$) δ 10.64-10.35 (m, 1H), 7.88 (dd, J = 2.7, 6.1 Hz, 1H), 7.76 (td, J = 3.5, 8.7 Hz, 1H), 7.61 (s, 1H), 7.22 (t, J = 9.3 Hz, 1H), 6.98 (s, 2H), 3.72 (s, 3H), 2.36 (d, J = 8.1 Hz, 6H), 1.89 (s, 6H) |
| N-(3-bromo-4-chloro-phenyl)-4-[2-[(1-ethynyl-3,3-difluoro-cyclobutyl)amino]-2-oxo-acetyl]-1,3,5-trimethyl-pyrrole-2-carboxamide | 133 | $^1$H NMR (400 MHz, DMSO-$d_6$) δ 10.45 (s, 1H), 9.61 (s, 1H), 8.22 (d, J = 2.4 Hz, 1H), 7.72-7.65 (m, 1H), 7.63-7.57 (m, 1H), 3.60 (s, 3H), 3.52 (s, 1H), 3.13 (br t, J = 11.9 Hz, 4H), 2.42 (s, 3H), 2.28-2.22 (m, 3H) |
| N-(4-bromo-3-chloro-phenyl)-4-[2-[(1-ethynyl-3,3-difluoro-cyclobutyl)amino]-2-oxo-acetyl]-1,3,5-trimethyl-pyrrole-2-carboxamide | 134 | $^1$H NMR (400 MHz, $CDCl_3$) δ 7.87 (d, J = 2.5 Hz, 1H), 7.58 (d, J = 8.6 Hz, 1H), 7.43 (s, 1H), 7.35-7.29 (m, 2H), 3.72 (s, 3H), 3.22 (br t, J = 11.4 Hz, 4H), 2.53 (s, 1H), 2.40 (d, J = 11.9 Hz, 6H) |
| N-(3-cyano-4-fluoro-phenyl)-4-[2-[[1-(1-cyclopropylpyrazol-4-yl)-1-methyl-ethyl]amino]-2-oxo-acetyl]-1,3,5-trimethyl-pyrrole-2-carboxamide | 135 | $^1$H NMR (400 MHz, DMSO-$d_6$) δ 10.49 (s, 1H), 8.50 (s, 1H), 8.20 (dd, J = 2.8, 5.8 Hz, 1H), 7.97 (ddd, J = 2.7, 4.9, 9.2 Hz, 1H), 7.69 (s, 1H), 7.54 (t, J = 9.1 Hz, 1H), 7.38 (s, 1H), 3.69-3.62 (m, 1H), 3.57 (s, 3H), 2.33 (s, 3H), 2.19 (s, 3H), 1.63 (s, 6H), 1.01-0.95 (m, 2H), 0.95-0.88 (m, 2H) |
| 4-[2-[[1-(1-cyclopropylpyrazol-4-yl)-1-methyl-ethyl]amino]-2-oxo-acetyl]-N-[4-fluoro-3-(trifluoromethyl)phenyl]-1,3,5-trimethyl-pyrrole-2-carboxamide | 136 | $^1$H NMR (400 MHz, DMSO-$d_6$) δ 10.47 (s, 1H), 8.49 (s, 1H), 8.20 (dd, J = 2.5, 6.5 Hz, 1H), 7.99-7.93 (m, 1H), 7.69 (s, 1H), 7.51 (t, J = 9.8 Hz, 1H), 7.38 (s, 1H), 3.68-3.61 (m, 1H), 3.57 (s, 3H), 3.44-3.20 (m, 58H), 2.34 (s, 3H), 2.19 (s, 3H), 1.63 (s, 6H), 1.00-0.95 (m, 2H), 0.94-0.88 (m, 2H) |
| N-(3-cyano-4-fluoro-phenyl)-1,3,5-trimethyl-4-[2-[[1-methyl-1-(2-methylpyrazol-3-yl)ethyl]amino]-2-oxo-acetyl]pyrrole-2-carboxamide | 137 | $^1$H NMR (400 MHz, $CDCl_3$) δ 8.04 (dd, J = 2.6, 5.4 Hz, 1H), 7.85 (s, 1H), 7.71 (ddd, J = 2.9, 4.3, 9.0 Hz, 1H), 7.38 (d, J = 1.6 Hz, 1H), 7.20 (t, J = 8.7 Hz, 1H), 7.14-7.14 (m, 1H), 7.12 (s, 1H), |

-continued

| Compound Name | Compound No. | $^1$H NMR |
|---|---|---|
| | | 6.22 (d, J = 1.8 Hz, 1H), 3.91 (s, 3H), 3.69 (s, 3H), 2.39 (s, 3H), 2.30 (s, 3H), 1.82 (s, 6H), 1.59 (s, 10H) |
| N-[4-fluoro-3-(trifluoromethyl)phenyl]-1,3,5-trimethyl-4-[2-[[1-methyl-1-(2-methylpyrazol-3-yl)ethyl]amino]-2-oxo-acetyl]pyrrole-2-carboxamide | 138 | $^1$H NMR (400 MHz, $CDCl_3$) δ 7.88 (dd, J = 2.6, 6.0 Hz, 1H), 7.78-7.67 (m, 1H), 7.62 (s, 1H), 7.38 (d, J = 1.9 Hz, 1H), 7.20 (t, J = 9.4 Hz, 1H), 7.12 (s, 1H), 6.23 (d, J = 1.9 Hz, 1H), 3.94 (s, 3H), 3.70 (s, 3H), 2.40-2.29 (m, 6H), 1.83 (s, 6H) |
| N-(3-cyano-4-fluoro-phenyl)-1,3,5-trimethyl-4-[2-[[1-methyl-1-(1,3,4-oxadiazol-2-yl)ethyl]amino]-2-oxo-acetyl]pyrrole-2-carboxamide | 139 | $^1$H NMR (400 MHz, $CDl_3$) δ 8.37 (s, 1H), 8.05 (dd, J = 2.8, 5.5 Hz, 1H), 7.76-7.70 (m, 2H), 7.40 (s, 1H), 7.21 (t, J = 8.7 Hz, 1H), 3.70 (s, 3H), 2.38 (s, 3H), 2.33 (s, 3H), 1.88 (s, 6H) |
| N-(3-cyano-4-fluoro-phenyl)-1,3,5-trimethyl-4-[2-[(1-methyl-1-thiazol-4-yl-ethyl)amino]-2-oxo-acetyl]pyrrole-2-carboxamide | 140 | $^1$H NMR (400 MHz, $CDCl_3$) δ 10.50 (s, 1H), 9.01 (d, J = 1.9 Hz, 1H), 8.79 (s, 1H), 8.20 (dd, J = 2.7, 5.8 Hz, 1H), 7.96 (ddd, J = 2.8, 4.9, 9.2 Hz, 1H), 7.54 (t, J = 9.1 Hz, 1H), 7.47 (d, J = 1.9 Hz, 1H), 3.57 (s, 3H), 2.34 (s, 3H), 2.20 (s, 3H), 2.07 (s, 1H), 1.71 (s, 6H) |
| N-[4-fluoro-3-(trifluoromethyl)phenyl]-1,3,5-trimethyl-4-[2-[(1-methyl-1-thiazol-4-yl-ethyl)amino]-2-oxo-acetyl]pyrrole-2-carboxamide | 141 | $^1$H NMR (400 MHz, DMSO-$d_6$) δ 10.48 (s, 1H), 9.01 (d, J = 1.9 Hz, 1H), 8.79 (s, 1H), 8.21 (dd, J = 2.5, 6.5 Hz, 1H), 7.95 (td, J = 3.6, 8.8 Hz, 1H), 7.57-7.42 (m, 2H), 3.57 (s, 3H), 2.36-2.33 (m, 3H), 2.21 (s, 3H), 1.71 (s, 6H) |
| 4-[2-[[1-(2-cyclopropyltriazol-4-yl)-3,3-difluoro-cyclobutyl]amino]-2-oxo-acetyl]-N-[4-fluoro-3-(trifluoromethyl)phenyl]-1,3,5-trimethyl-pyrrole-2-carboxamide | 142 | $^1$H NMR (400 MHz, $CDCl_3$) δ 7.88 (dd, J = 2.6, 6.0 Hz, 1H), 7.77-7.69 (m, 1H), 7.63-7.54 (m, 2H), 7.49 (s, 1H), 7.22 (t, J = 9.3 Hz, 1H), 3.97 (tt, J = 3.8, 7.5 Hz, 1H), 3.72 (s, 3H), 3.44-3.23 (m, 4H), 2.38 (d, J = 8.9 Hz, 6H), 1.38-1.29 (m, 2H), 1.16-1.06 (m, 2H) |
| N-[4-fluoro-3-(trifluoromethyl)phenyl]-1,3,5-trimethyl-4-[2-[[1-methyl-1-(1,3,4-oxadiazol-2-yl)ethyl]amino]-2-oxo-acetyl]pyrrole-2-carboxamide | 143 | $^1$H NMR (400 MHz, $CDCl_3$) δ 8.29 (s, 1H), 7.82 (dd, J = 2.6, 6.1 Hz, 1H), 7.66 (td, J = 3.5, 8.9 Hz, 1H), 7.50 (s, 1H), 7.32 (s, 1H), 7.13 (t, J = 9.3 Hz, 1H), 3.63 (s, 3H), 2.29 (d, J = 13.4 Hz, 6H), 1.81 (s, 6H) |
| N-(3-cyano-4-fluoro-phenyl)-1,3,5-trimethyl-4-[2-[(1-methyl-1-pyrimidin-5-yl-ethyl)amino]-2-oxo-acetyl]pyrrole-2-carboxamide | 144 | $^1$H NMR (400 MHz, DMSO-$d_6$) δ 10.53 (s, 1H), 9.17 (s, 1H), 9.08 (s, 1H), 8.85 (s, 2H), 8.21 (dd, J = 2.8, 5.7 Hz, 1H), 7.97 (br dd, J = 3.4, 8.8 Hz, 1H), 7.55 (t, J = 9.1 Hz, 1H), 3.59 (s, 3H), 2.38 (s, 3H), 2.22 (s, 3H), 1.71 (s, 6H) |
| N-(3-cyano-4-fluoro-phenyl)-4-[2-[[1-(5-fluoro-2-pyridyl)-1-methyl-ethyl]amino]-2-oxo-acetyl]-1,3,5-trimethyl-pyrrole-2-carboxamide | 145 | $^1$H NMR (400 MHz, DMSO-$d_6$) δ 10.51 (br s, 1H), 9.01 (s, 1H), 8.49 (d, J = 2.9 Hz, 1H), 8.21 (dd, J = 2.6, 5.8 Hz, 1H), 7.97 (ddd, J = 2.7, 4.9, 9.1 Hz, 1H), 7.72 (dt, J = 3.0, 8.8 Hz, 1H), 7.61-7.48 (m, 2H), 3.59 (s, 3H), 2.38 (s, 3H), 2.24 (s, 3H), 1.66 (s, 6H) |
| 4-[2-[[1-(1-cyclopropyltriazol-4-yl)-3,3-difluoro-cyclobutyl]amino]-2-oxo-acetyl]-N-[4-fluoro-3-(trifluoromethyl)phenyl]-1,3,5-trimethyl-pyrrole-2-carboxamide | 146 | $^1$H NMR (400 MHz, $CDl_3$) δ 7.90 (dd, J = 2.5, 5.9 Hz, 1H), 7.80 (br dd, J = 3.6, 9.0 Hz, 1H), 7.73-7.62 (m, 3H), 7.22 (t, J = 9.4 Hz, 1H), 3.80-3.67 (m, 4H), 3.44-3.21 (m, 4H), 2.36 (d, J = 15.4 Hz, 6H), 1.31-1.12 (m, 4H) |

-continued

| Compound Name | Compound No. | $^1$H NMR |
|---|---|---|
| 4-[2-[[l-(5-fluoro-2-pyridyl)-1-methyl-ethyl]amino]-2-oxo-acetyl]-N-[4-fluoro-3-(trifluoromethyl)phenyl]-1,3,5-trimethyl-pyrrole-2-carboxamide | 147 | $^1$H NMR (400 MHz, DMSO-$d_6$) δ 10.49 (s, 1H), 9.01 (s, 1H), 8.49 (d, J = 2.9 Hz, 1H), 8.21 (dd, J = 2.3, 6.4 Hz, 1H), 8.02-7.88 (m, 1H), 7.72 (dt, J = 3.0, 8.8 Hz, 1H), 7.61-7.45 (m, 2H), 3.58 (s, 3H), 2.38 (s, 3H), 2.24 (s, 3H), 2.07 (s, 1H), 1.65 (s, 6H) |
| N-[4-fluoro-3-(trifluoromethyl)phenyl]-1,3,5-trimethyl-4-[2-[(1-methyl-1-pyrimidin-5-yl-ethyl)amino]-2-oxo-acetyl]pyrrole-2-carboxamide | 148 | $^1$H NMR (400 MHz, DMSO-$d_6$) δ 10.50 (s, 1H), 9.16 (s, 1H), 9.07 (s, 1H), 8.85 (s, 2H), 8.21 (dd, J = 2.4, 6.5 Hz, 1H), 8.02-7.89 (m, 1H), 7.52 (t, J = 9.8 Hz, 1H), 3.58 (s, 3H), 2.38 (s, 3H), 2.21 (s, 3H), 1.70 (s, 6H) |
| N-[4-fluoro-3-(trifluoromethyl)phenyl]-1,3,5-trimethyl-4-[2-[[1-methyl-1-(1-methylimidazol-4-yl)ethyl]amino]-2-oxo-acetyl]pyrrole-2-carboxamide | 149 | $^1$H NMR (400 MHz, DMSO-$d_6$) δ 10.64-10.26 (m, 1H), 8.74 (s, 1H), 8.21 (br d, J = 3.8 Hz, 1H), 7.95 (br d, J = 3.4 Hz, 1H), 7.50 (br t, J = 9.6 Hz, 1H), 7.30-6.82 (m, 1H), 3.88 (br s, 2H), 3.57-3.46 (m, 3H), 2.35-2.27 (m, 3H), 1.82-1.71 (m, 2H), 1.29-1.13 (m, 5H) |
| 4-[2-[[3,3-difluoro-1-(4-pyridyl)cyclobutyl]amino]-2-oxo-acetyl]-N-[4-fluoro-3-(trifluoromethyl)phenyl]-1,3,5-trimethyl-pyrrole-2-carboxamide | 150 | $^1$H NMR (400 MHz, $CDCl_3$) δ 8.69-8.62 (m, 2H), 7.87 (dd, J = 2.6, 6.1 Hz, 1H), 7.75-7.68 (m, 1H), 7.53 (s, 1H), 7.42 (s, 1H), 7.40-7.36 (m, 2H), 7.22 (t, J = 9.4 Hz, 1H), 3.71 (s, 3H), 3.28 (dd, J = 10.3, 12.8 Hz, 4H), 2.34 (d, J = 12.6 Hz, 6H) |
| N-(3-cyano-4-fluoro-phenyl)-1,3,5-trimethyl-4-[2-oxo-2-[[3-(1H-pyrazol-4-yl)oxetan-3-yl]amino]acetyl]pyrrole-2-carboxamide | 151 | $^1$H NMR (400 MHz, DMSO-$d_6$) δ 12.79 (br s, 1H), 10.54 (s, 1H), 9.67 (s, 1H), 8.21 (dd, J = 2.6, 5.8 Hz, 1H), 7.96 (dt, J = 2.7, 4.5 Hz, 1H), 7.67 (br s, 2H), 7.54 (t, J = 9.1 Hz, 1H), 4.90 (d, J = 6.5 Hz, 2H), 4.75 (d, J = 6.5 Hz, 2H), 3.59 (s, 3H), 2.37 (s, 3H), 2.22 (s, 3H) |
| N-(3-cyano-4-fluoro-phenyl)-1,3,5-trimethyl-4-[2-[(1-methyl-1-pyrimidin-4-yl-ethyl)amino]-2-oxo-acetyl]pyrrole-2-carboxamide | 152 | $^1$H NMR (400 MHz, DMSO-$d_6$) δ 10.53 (s, 1H), 9.23-9.08 (m, 2H), 8.77 (d, J = 5.4 Hz, 1H), 8.21 (dd, J = 2.6, 5.8 Hz, 1H), 7.96 (ddd, J = 2.7, 4.9, 9.1 Hz, 1H), 7.63-7.48 (m, 2H), 3.59 (s, 3H), 2.40 (s, 3H), 2.24 (s, 3H), 1.63 (s, 6H) |
| N-[4-fluoro-3-(trifluoromethyl)phenyl]-1,3,5-trimethyl-4-[2-[(1-methyl-1-pyrimidin-4-yl-ethyl)amino]-2-oxo-acetyl]pyrrole-2-carboxamide | 153 | $^1$H NMR (400 MHz, $CDCl_3$) δ 9.19 (d, J = 0.9 Hz, 1H), 8.74 (d, J = 5.5 Hz, 1H), 8.22 (s, 1H), 7.87 (dd, J = 2.6, 6.1 Hz, 1H), 7.72 (td, J = 3.5, 8.6 Hz, 1H), 7.50 (s, 1H), 7.44 (dd, J = 1.2, 5.4 Hz, 1H), 7.20 (t, J = 9.3 Hz, 1H), 3.70 (s, 3H), 2.38 (d, J = 5.9 Hz, 6H), 1.81 (s, 6H) |
| N-(3-cyano-4-fluoro-phenyl)-4-[2-[[3-(1H-imidazol-2-yl)oxetan-3-yl]amino]-2-oxo-acetyl]-1,3,5-trimethyl-pyrrole-2-carboxamide | 154 | $^1$H NMR (400 MHz, $CDCl_3$) δ 8.09-7.96 (m, 2H), 7.81-7.68 (m, 1H), 7.54 (d, J 12.4 Hz, 1H), 7.23 (d, J = 8.9 Hz, 1H), 7.06 (s, 2H), 5.28 (d, J = 6.8 Hz, 2H), 5.06 (d, J = 6.9 Hz, 2H), 3.74 (s, 3H), 2.40 (d, J = 9.6 Hz, 6H), 1.26 (s, 1H) |
| N-[4-fluoro-3-(trifluoromethyl)phenyl]-4-[2-[[3-(1H-imidazol-2-yl)oxetan-3-yl]amino]-2-oxo-acetyl]-1,3,5-trimethyl-pyrrole-2-carboxamide | 155 | $^1$H NMR (400 MHz, $CDCl_3$) δ 7.99 (s, 1H), 7.88 (dd, J = 2.3, 6.1 Hz, 1H), 7.76 (br d, J = 8.5 Hz, 1H), 7.55-7.41 (m, 1H), 7.25-7.17 (m, 2H), 7.06 (s, 2H), 5.29 (d, J = 6.8 Hz, 2H), 5.05 (d, J = 6.6 Hz, 2H), 3.74 (s, 3H), 2.40 (d, J = 5.1 Hz, 6H) |

-continued

| Compound Name | Compound No. | $^1$H NMR |
|---|---|---|
| N-[4-fluoro-3-(trifluoromethyl)phenyl]-4-[2-[[3-(1H-imidazol-4-yl)oxetan-3-yl]amino]-2-oxo-acetyl]-1,3,5-trimethyl-pyrrole-2-carboxamide | 156 | $^1$H NMR (400 MHz, Methanol-$d_4$) δ 8.09 (dd, J = 2.6, 6.3 Hz, 1H), 7.93-7.84 (m, 1H), 7.73 (s, 1H), 7.33 (t, J = 9.6 Hz, 1H), 7.17 (s, 1H), 5.11-5.00 (m, 4H), 3.65 (s, 3H), 2.41 (s, 3H), 2.34-2.21 (m, 3H) |
| N-(3-cyano-4-fluoro-phenyl)-4-[2-[[3-(1H-imidazol-4-yl)oxetan-3-yl]amino]-2-oxo-acetyl]-1,3,5-trimethyl-pyrrole-2-carboxamide | 157 | $^1$H NMR (300 MHz, Methanol-$d_4$) δ 8.09 (dd, J = 2.6, 6.3 Hz, 1H), 7.93-7.84 (m, 1H), 7.73 (s, 1H), 7.33 (t, J = 9.6 Hz, 1H), 7.17 (s, 1H), 5.11-5.00 (m, 4H), 3.65 (s, 3H), 2.41 (s, 3H), 2.34-2.21 (m, 3H) |
| N-[4-fluoro-3-(trifluoromethyl)phenyl]-1,3,5-trimethyl-4-[2-oxo-2-[[3-(1H-pyrazol-4-yl)oxetan-3-yl]amino]acetyl]pyrrole-2-carboxamide | 158 | $^1$H NMR (300 MHz, Methanol-$d_4$) δ 8.40 (s, 1H), 8.13 (dd, J = 2.8, 5.6 Hz, 1H), 7.92 (ddd, J = 2.8, 4.7, 9.2 Hz, 1H), 7.46 (d, J = 0.9 Hz, 1H), 7.37 (t, J = 8.9 Hz, 1H), 5.11-4.96 (m, 4H), 3.66 (s, 3H), 2.44 (s, 3H), 2.32 (s, 3H) |
| N-[4-fluoro-3-(trifluoromethyl)phenyl]-1,3,5-trimethyl-4-[2-[[1-methyl-1-(2-oxo-1H-pyridin-3-yl)ethyl]amino]-2-oxo-acetyl]pyrrole-2-carboxamide | 159 | $^1$H NMR (400 MHz, DMSO-$d_6$) δ 12.79 (brs, 1H), 10.50 (s, 1H), 9.65 (s, 1H), 8.21 (dd, J = 2.5, 6.5 Hz, 1H), 8.02-7.89 (m, 1H), 7.78 (s, 1H), 7.63-7.43 (m, 2H), 4.91 (d, J = 6.5 Hz, 2H), 4.75 (d, J = 6.5 Hz, 2H), 3.59 (s, 3H), 3.37-3.28 (m, 47H), 2.37 (s, 3H), 2.23 (s, 3H) |
| 4-[2-[[1-(1H-benzimidazol-5-yl)-1-methyl-ethyl]amino]-2-oxo-acetyl]-N-(3-cyano-4-fluoro-phenyl)-1,3,5-trimethyl-pyrrole-2-carboxamide | 160 | $^1$H NMR (400 MHz, DMSO-$d_6$) δ 11.55 (br d, J = 1.6 Hz, 1H), 10.49 (s, 1H), 8.69 (s, 1H), 8.21 (dd, J = 2.4, 6.5 Hz, 1H), 7.99-7.91 (m, 1H), 7.52 (t, J = 9.8 Hz, 1H), 7.42 (dd, J = 2.0, 7.0 Hz, 1H), 7.30 (br d, J = 5.0 Hz, 1H), 6.19 (t, J = 6.8 Hz, 1H), 3.58 (s, 3H), 2.40 (s, 3H), 2.25 (s, 3H), 1.71 (s, 6H) |
| N-(3-cyano-4-fluoro-phenyl)-1,3,5-trimethyl-4-[2-[[1-methyl-1-(2-oxo-1H-pyridin-3-yl)ethyl]amino]-2-oxo-acetyl]pyrrole-2-carboxamide | 161 | $^1$H NMR (400 MHz, DMSO-$d_6$) δ 12.57-12.27 (m, 1H), 10.52 (br s, 1H), 8.89 (s, 1H), 8.21 (dd, J = 2.4, 5.6 Hz, 1H), 8.18 (s, 1H), 8.03-7.90 (m, 1H), 7.67-7.46 (m, 3H), 7.30 (br d, J = 8.8 Hz, 1H), 3.61-3.53 (m, 3H), 2.38 (s, 3H), 2.29-2.23 (m, 3H), 1.71 (s, 6H) |
| 4-[2-[[1-(1H-benzimidazol-5-yl)-1-methyl-ethyl]amino]-2-oxo-acetyl]-N-(4-fluoro-3-methyl-phenyl)-1,3,5-trimethyl-pyrrole-2-carboxamide | 162 | $^1$H NMR (400 MHz, DMSO-$d_6$) δ 11.68-11.42 (m, 1H), 10.51 (br s, 1H), 8.70 (s, 1H), 8.21 (dd, J = 2.7, 5.8 Hz, 1H), 7.97 (ddd, J = 2.8, 4.8, 9.2 Hz, 1H), 7.54 (t, J = 9.1 Hz, 1H), 7.42 (dd, J = 2.0, 7.0 Hz, 1H), 7.30 (dd, J = 1.8, 6.3 Hz, 1H), 6.19 (t, J = 6.7 Hz, 1H), 3.58 (s, 3H), 2.40 (s, 3H), 2.25 (s, 3H), 1.71 (s, 6H) |

Example 20

Additional Compounds

The foregoing syntheses are exemplary and can be used as a starting point to prepare a large number of additional compounds. Examples of compounds of Formula (I) that can be prepared in various ways, including those synthetic schemes shown and described herein, are provided below. Those skilled in the art will be able to recognize modifications of the disclosed syntheses and to devise routes based on the disclosures herein; all such modifications and alternate routes are within the scope of the claims.

| Structure | Name | Compound No. |
|---|---|---|
| 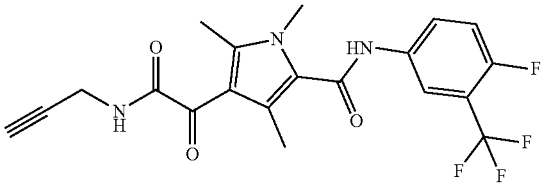 [SMILES: C#CCNC(=O)C(=O)c1c(C)c(C(=O)Nc2ccc(F)c(C(F)(F)F)c2)n(C)c1C] | N-[4-fluoro-3-(trifluoromethyl)phenyl]-1,3,5-trimethyl-4-[2-oxo-2-(prop-2-ynylamino)acetyl]pyrrole-2-carboxamide | 1 |
| 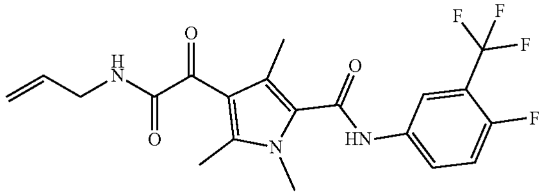 [SMILES: C=CCNC(=O)C(=O)c1c(C)c(C(=O)Nc2ccc(F)c(C(F)(F)F)c2)n(C)c1C] | 4-[2-(allylamino)-2-oxo-acetyl]-N-[4-fluoro-3-(trifluoromethyl)phenyl]-1,3,5-trimethyl-pyrrole-2-carboxamide | 2 |
| 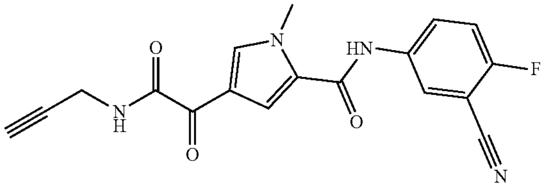 [SMILES: C#CCNC(=O)C(=O)c1cc(C(=O)Nc2ccc(F)c(C#N)c2)n(C)c1] | N-(3-cyano-4-fluoro-phenyl)-1-methyl-4-[2-oxo-2-(prop-2-ynylamino)acetyl]pyrrole-2-carboxamide | 3 |
| 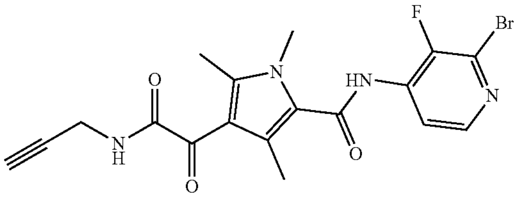 [SMILES: C#CCNC(=O)C(=O)c1c(C)c(C(=O)Nc2ccnc(Br)c2F)n(C)c1C] | N-(2-bromo-3-fluoro-4-pyridyl)-1,3,5-trimethyl-4-[2-oxo-2-(prop-2-ynylamino)acetyl]pyrrole-2-carboxamide | 4 |
| 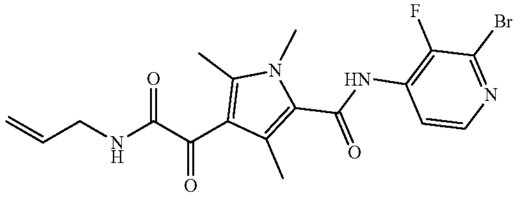 [SMILES: C=CCNC(=O)C(=O)c1c(C)c(C(=O)Nc2ccnc(Br)c2F)n(C)c1C] | 4-[2-(allylamino)-2-oxo-acetyl]-N-(2-bromo-3-fluoro-4-pyridyl)-1,3,5-trimethyl-pyrrole-2-carboxamide | 5 |
| 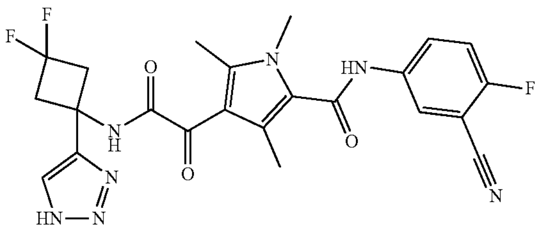 [SMILES: Cc1c(C(=O)C(=O)NC2(c3c[nH]nn3)CC(F)(F)C2)c(C)n(C)c1C(=O)Nc1ccc(F)c(C#N)c1] | N-(3-cyano-4-fluoro-phenyl)-4-[2-[[3,3-difluoro-1-(1H-triazol-4-yl)cyclobutyl]amino]-2 oxo-acetyl]-1,3,5-trimethyl-pyrrole-2-carboxamide | 19 |

-continued

| Structure | Name | Compound No. |
|---|---|---|
| 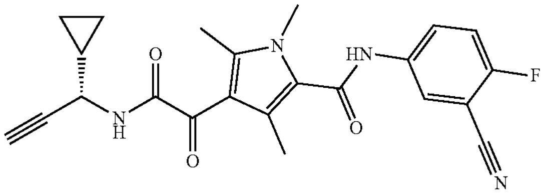 [SMILES: C#C[C@@H](NC(=O)C(=O)c1c(C)c(C(=O)Nc2ccc(F)c(C#N)c2)n(C)c1C)C1CC1] | N-(3-cyano-4-fluoro-phenyl)-1,3,5-trimethyl-4-[2-oxo-2-[[(1S)-1-cyclopropylprop-2-ynyl]amino]acetyl]pyrrole-2-carboxamide | 23b |
| 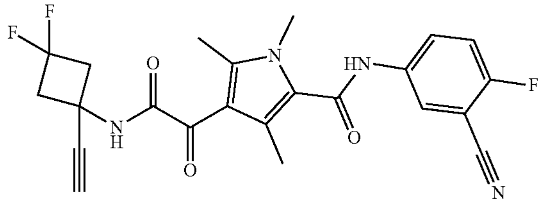 [SMILES: C#CC1(NC(=O)C(=O)c2c(C)c(C(=O)Nc3ccc(F)c(C#N)c3)n(C)c2C)CC(F)(F)C1] | N-(3-cyano-4-fluoro-phenyl)-4-[2-[(1-ethynyl-3,3-difluoro-cyclobutyl)amino]-2-oxo-acetyl]-1,3,5-trimethyl-pyrrole-2-carboxamide | 24 |
| 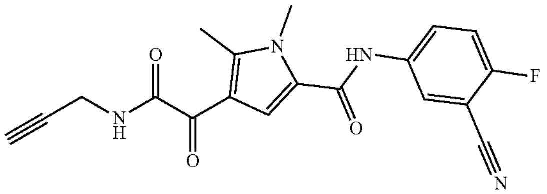 [SMILES: C#CCNC(=O)C(=O)c1cc(C(=O)Nc2ccc(F)c(C#N)c2)n(C)c1C] | N-(3-cyano-4-fluoro-phenyl)-1,5-dimethyl-4-[2-oxo-2-(prop-2-ynylamino)acetyl]pyrrole-2-carboxamide | 27 |
| 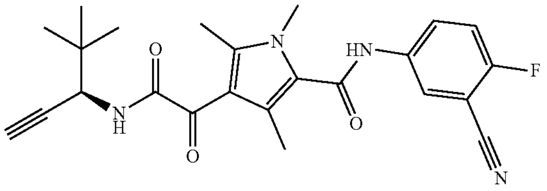 [SMILES: C#C[C@H](NC(=O)C(=O)c1c(C)c(C(=O)Nc2ccc(F)c(C#N)c2)n(C)c1C)C(C)(C)C] | N-(3-cyano-4-fluoro-phenyl)-1,3,5-trimethyl-4-[2-oxo-2-[[(1R)-1-tert-butylprop-2-ynyl]amino]acetyl]pyrrole-2-carboxamide | 30a |
| 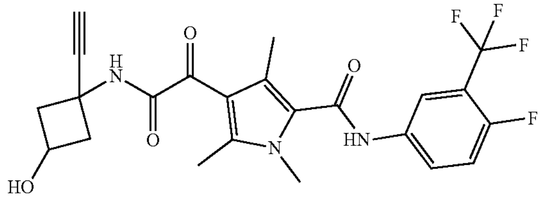 [SMILES: C#CC1(NC(=O)C(=O)c2c(C)c(C(=O)Nc3ccc(F)c(C(F)(F)F)c3)n(C)c2C)CC(O)C1] | 4-[2-[(1-ethynyl-3-hydroxy-cyclobutyl)amino]-2-oxo-acetyl]-N-[4-fluoro-3-(trifluoromethyl)phenyl]-1,3,5-trimethyl-pyrrole-2-carboxamide | 49 |
| 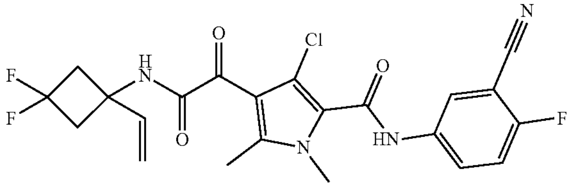 [SMILES: C=CC1(NC(=O)C(=O)c2c(Cl)c(C(=O)Nc3ccc(F)c(C#N)c3)n(C)c2C)CC(F)(F)C1] | 3-chloro-N-(3-cyano-4-fluoro-phenyl)-4-[2-[(3,3-difluoro-1-vinyl-cyclobutyl)amino]-2-oxo-acetyl]-1,5-dimethyl-pyrrole-2-carboxamide | 51 |
| 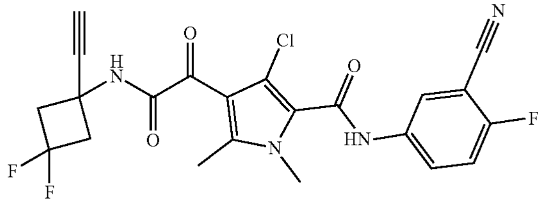 [SMILES: C#CC1(NC(=O)C(=O)c2c(Cl)c(C(=O)Nc3ccc(F)c(C#N)c3)n(C)c2C)CC(F)(F)C1] | 3-chloro-N-(3-cyano-4-fluoro-phenyl)-4-[2-[(1-ethynyl-3,3-difluoro-cyclobutyl)amino]-2-oxo-acetyl]-1,5-dimethyl-pyrrole-2-carboxamide | 52 |

-continued

| Structure | Name | Compound No. |
|---|---|---|
| 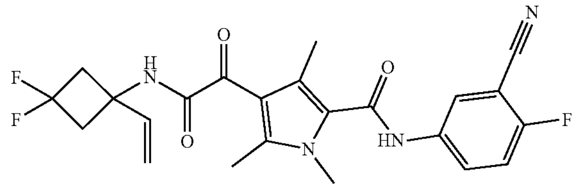 [SMILES: C=CC1(NC(=O)C(=O)c2c(C)c(C(=O)Nc3ccc(F)c(C#N)c3)n(C)c2C)CC(F)(F)C1] | N-(3-cyano-4-fluoro-phenyl)-4-[2-[(3,3-difluoro-1-vinyl-cyclobutyl)amino]-2-oxo-acetyl]-1,3,5-trimethyl-pyrrole-2-carboxamide | 53 |
| 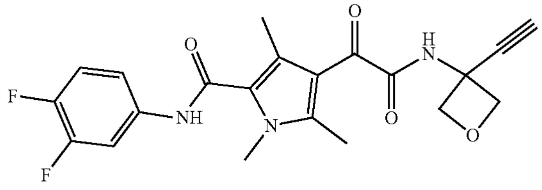 [SMILES: C#CC1(NC(=O)C(=O)c2c(C)c(C(=O)Nc3ccc(F)c(F)c3)n(C)c2C)COC1] | N-(3,4-difluorophenyl)-4-[2-[(3-ethynyloxetan-3-yl)amino]-2-oxo-acetyl]-1,3,5-trimethyl-pyrrole-2-carboxamide | 86 |
| 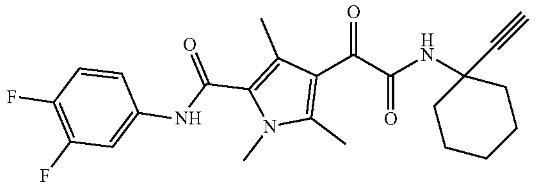 [SMILES: C#CC1(NC(=O)C(=O)c2c(C)c(C(=O)Nc3ccc(F)c(F)c3)n(C)c2C)CCCCC1] | N-(3,4-difluorophenyl)-4-[2-[(1-ethynylcyclohexyl)amino]-2-oxo-acetyl]-1,3,5-trimethyl-pyrrole-2-carboxamide | 87 |
| 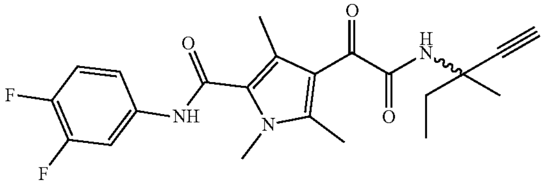 [SMILES: C#CC(C)(CC)NC(=O)C(=O)c1c(C)c(C(=O)Nc2ccc(F)c(F)c2)n(C)c1C] | N-(3,4-difluorophenyl)-4-[2-[(1-ethyl-1-methyl-prop-2-ynyl)amino]-2-oxo-acetyl]-1,3,5-trimethyl-pyrrole-2-carboxamide | 88 |
| 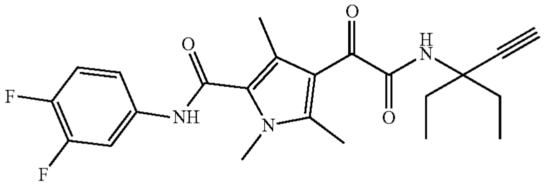 [SMILES: C#CC(CC)(CC)NC(=O)C(=O)c1c(C)c(C(=O)Nc2ccc(F)c(F)c2)n(C)c1C] | 4-[2-(1,1-diethylprop-2-ynylamino)-2-oxo-acetyl]-N-(3,4-difluorophenyl)-1,3,5-trimethyl-pyrrole-2-carboxamide | 89 |
| 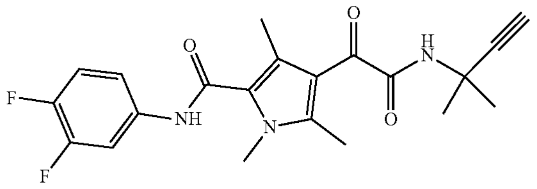 [SMILES: C#CC(C)(C)NC(=O)C(=O)c1c(C)c(C(=O)Nc2ccc(F)c(F)c2)n(C)c1C] | N-(3,4-difluorophenyl)-4-[2-(1,1-dimethylprop-2-ynylamino)-2-oxo-acetyl]-1,3,5-trimethyl-pyrrole-2-carboxamide | 90 |
| 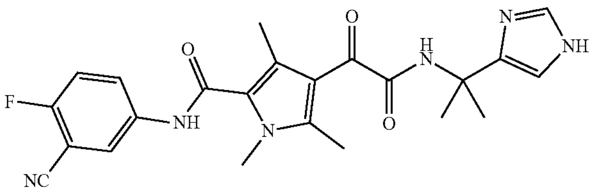 [SMILES: Cc1c(C(=O)C(=O)NC(C)(C)c2c[nH]cn2)c(C)n(C)c1C(=O)Nc1ccc(F)c(C#N)c1] | N-(3-cyano-4-fluoro-phenyl)-4-[2-[[1-(1H-imidazol-4-yl)-1-methyl-ethyl]amino]-2-oxo-acetyl]-1,3,5-trimethyl-pyrrole-2-carboxamide | 104 |
| 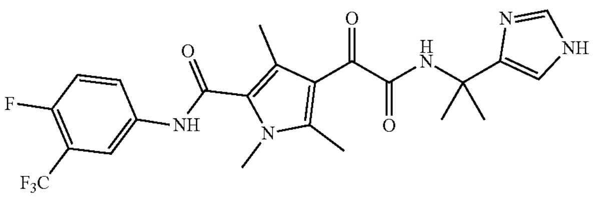 [SMILES: Cc1c(C(=O)C(=O)NC(C)(C)c2c[nH]cn2)c(C)n(C)c1C(=O)Nc1ccc(F)c(C(F)(F)F)c1] | N-[4-fluoro-3-(trifluoromethyl)phenyl]-4-[2-[[1-(1H-imidazol-4-yl)-1-methyl-ethyl]amino]-2-oxo-acetyl]-1,3,5-trimethyl-pyrrole-2-carboxamide | 106 |

-continued

| Structure | Name | Compound No. |
|---|---|---|
| 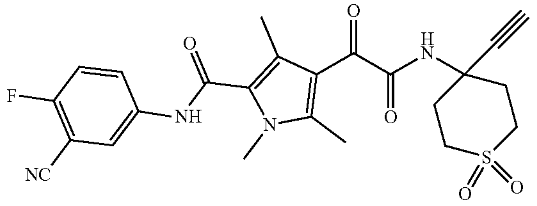 [SMILES: C#CC1(NC(=O)C(=O)c2c(C)c(C(=O)Nc3ccc(F)c(C#N)c3)n(C)c2C)CCS(=O)(=O)CC1] | N-(3-cyano-4-fluoro-phenyl)-4-[2-[(4-ethynyl-1,1-dioxo-thian-4-yl)amino]-2-oxo-acetyl]-1,3,5-trimethyl-pyrrole-2-carboxamide | 108 |
| 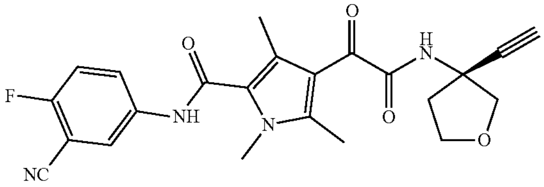 [SMILES: C#C[C@]1(NC(=O)C(=O)c2c(C)c(C(=O)Nc3ccc(F)c(C#N)c3)n(C)c2C)CCOC1] | N-(3-cyano-4-fluoro-phenyl)-1,3,5-trimethyl-4-[2-oxo-2-[[(3R)-3-ethynyltetrahydrofuran-3-yl]amino]acetyl]pyrrole-2-carboxamide | 111 |
| 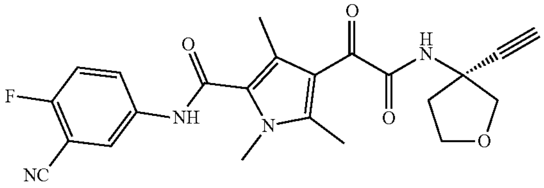 [SMILES: C#C[C@@]1(NC(=O)C(=O)c2c(C)c(C(=O)Nc3ccc(F)c(C#N)c3)n(C)c2C)CCOC1] | N-(3-cyano-4-fluoro-phenyl)-1,3,5-trimethyl-4-[2-oxo-2-[[(3S)-3-ethynyltetrahydrofuran-3-yl]amino]acetyl]pyrrole-2-carboxamide | 112 |
| 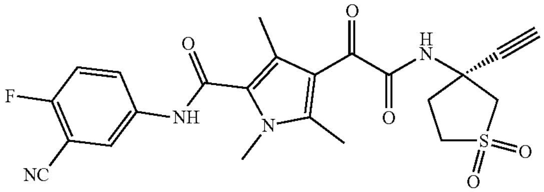 [SMILES: C#C[C@@]1(NC(=O)C(=O)c2c(C)c(C(=O)Nc3ccc(F)c(C#N)c3)n(C)c2C)CCS(=O)(=O)C1] | N-(3-cyano-4-fluoro-phenyl)-1,3,5-trimethyl-4-[2-oxo-2-[[(3S)-3-ethynyl-1,1-dioxo-thiolan-3-yl]amino]acetyl]pyrrole-2-carboxamide | 113a |
| 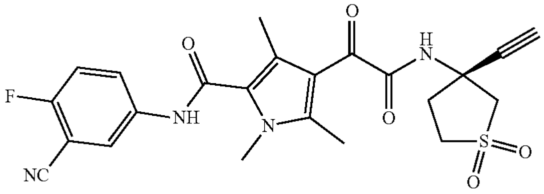 [SMILES: C#C[C@]1(NC(=O)C(=O)c2c(C)c(C(=O)Nc3ccc(F)c(C#N)c3)n(C)c2C)CCS(=O)(=O)C1] | N-(3-cyano-4-fluoro-phenyl)-1,3,5-trimethyl-4-[2-oxo-2-[[(3R)-3-ethynyl-1,1-dioxo-thiolan-3-yl]amino]acetyl]pyrrole-2-carboxamide | 113b |
| 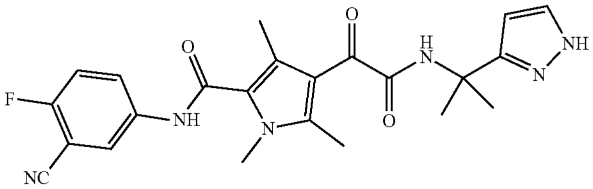 [SMILES: Cc1c(C(=O)C(=O)NC(C)(C)c2cc[nH]n2)c(C)n(C)c1C(=O)Nc1ccc(F)c(C#N)c1] | N-(3-cyano-4-fluoro-phenyl)-1,3,5-trimethyl-4-[2-[[1-methyl-1-(1H-pyrazol-3-yl)ethyl]amino]-2-oxo-acetyl]pyrrole-2-carboxamide | 114 |
| 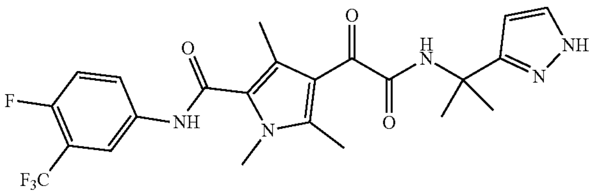 [SMILES: Cc1c(C(=O)C(=O)NC(C)(C)c2cc[nH]n2)c(C)n(C)c1C(=O)Nc1ccc(F)c(C(F)(F)F)c1] | N-[4-fluoro-3-(trifluoromethyl)phenyl]-1,3,5-trimethyl-4-[2-[[1-methyl-1-(1H-pyrazol-3-yl)ethyl]amino]-2-oxo-acetyl]pyrrole-2-carboxamide | 115 |

-continued

| Structure | Name | Compound No. |
|---|---|---|
| 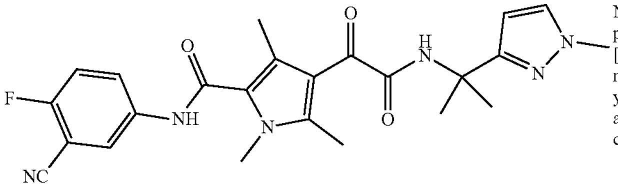 | N-(3-cyano-4-fluoro-phenyl)-1,3,5-trimethyl-4-[2-[[1-methyl-1-(1-methylpyrazol-3-yl)ethyl]amino]-2-oxo-acetyl]pyrrole-2-carboxamide | 116 |
| 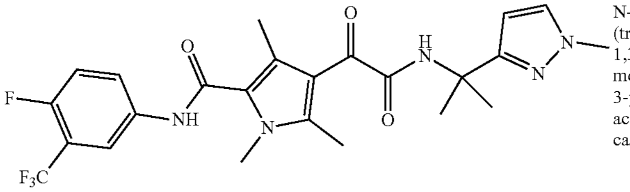 | N-[4-fluoro-3-(trifluoromethyl)phenyl]-1,3,5-trimethyl-4-[2-[[1-methyl-1-(1-methylpyrazol-3-yl)ethyl]amino]-2-oxo-acetyl]pyrrole-2-carboxamide | 117 |
| 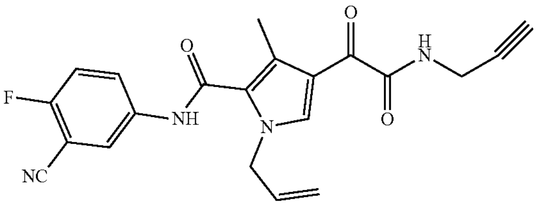 [SMILES: C#CCNC(=O)C(=O)c1cn(CC=C)c(C(=O)Nc2ccc(F)c(C#N)c2)c1C] | 1-allyl-N-(3-cyano-4-fluoro-phenyl)-3-methyl-4-[2-oxo-2-(prop-2-ynylamino)acetyl]pyrrole-2-carboxamide | 118 |
| 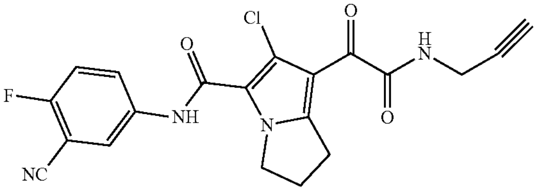 [SMILES: C#CCNC(=O)C(=O)c1c(Cl)c(C(=O)Nc2ccc(F)c(C#N)c2)n2c1CCC2] | 2-chloro-N-(3-cyano-4-fluoro-phenyl)-1-[2-oxo-2-(prop-2-ynylamino)acetyl]-6,7-dihydro-5H-pyrrolizine-3-carboxamide | 119 |
| 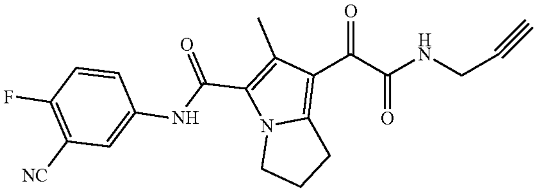 [SMILES: C#CCNC(=O)C(=O)c1c(C)c(C(=O)Nc2ccc(F)c(C#N)c2)n2c1CCC2] | N-(3-cyano-4-fluoro-phenyl)-2-methyl-1-[2-oxo-2-(prop-2-ynylamino)acetyl]-6,7-dihydro-5H-pyrrolizine-3-carboxamide | 120 |
| 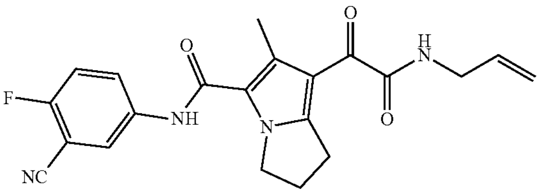 [SMILES: C=CCNC(=O)C(=O)c1c(C)c(C(=O)Nc2ccc(F)c(C#N)c2)n2c1CCC2] | 1-[2-(allylamino)-2-oxo-acetyl]-N-(3-cyano-4-fluoro-phenyl)-2-methyl-6,7-dihydro-5H-pyrrolizine-3-carboxamide | 121 |
| 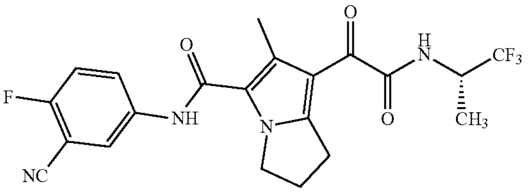 [SMILES: Cc1c(C(=O)C(=O)N[C@@H](C)C(F)(F)F)c2n(c1C(=O)Nc1ccc(F)c(C#N)c1)CCC2] | N-(3-cyano-4-fluoro-phenyl)-2-methyl-1-[2-oxo-2-[[(1S)-2,2,2-trifluoro-1-methyl-ethyl]amino]acetyl]-6,7-dihydro-5H-pyrrolizine-3-carboxamide | 122 |

(including pharmaceutically acceptable salts of any of the foregoing).

Example A

HBV-DNA Antiviral Assay Using HepG2.2.15 Cells

The following assay procedure describes the HBV antiviral assay. This assay uses HepG2.2.15 cells, which have been transfected with HBV genome, and extracellular HBV DNA quantification as endpoint. Cell viability is assessed in parallel by measuring the intracellular ATP content using the CellTiter-Glo® reagent from Promega.

On day 0, HepG2.2.15 cells were seeded in 96-well plates at a density of $6.0\times10^4$ cells/well (0.1 mL/well). The cells were incubated at 37° C. and 5% $CO_2$.

On day 1, the test articles were diluted and added to cell culture wells (8 concentrations, 4-fold dilution, in duplicate). GLS4, Tenofovir and Sorafenib were used as reference compounds. 100 μL of culture medium containing the compounds was added to the plate, and the final total volume per well was 200 μL. The final concentration of DMSO in the culture medium was 0.5%. The plate map of compound treatment is shown below. The cells were cultured at 37° C. and 5% $CO_2$ for 3 days. The plate map of compound treatment is shown in FIG. 1.

On day 4, the plates were refreshed with culture media with compounds.

On day 7, cell viability was assessed using the CellTiter-Glo®, and the cell culture supernatants were collected for determination of HBV DNA by qPCR.

HBV DNA Quantification by qPCR

Extracellular DNA was isolated with QIAamp 96 DNA Blood Kit per the manufacturer's manual. HBV DNA was then quantified by qPCR with HBV specific primers and probes as specified in Table 1 using the FastStart Universal MasterMix from Roche on an ABI-7900HT. The PCR cycle program consisted of 95° C. for 10 min, followed by 40 cycles at 95° C. for 15 sec and 60° C. for 1 min.

TABLE 1

HBV DNA Primers and Probe

| Items | Name | Sequence (5'→3') |
|---|---|---|
| HBV Primer | HBV-forward | GTGTCTGCGGCGTTTTATCA (SEQ ID NO: 1) |
| | HBV-reverse | GACAAACGGGCAACATACCTT (SEQ ID NO: 2) |
| HBV Probe | HBV probe | FAM-CCTCTKCATCCTGCTGC TATGCCTCATC-TAMRA (SEQ ID NO: 3) |

A DNA standard was prepared by dilution of the pAAV2 HBV1.3 plasmid with concentrations ranging from 10 to $1\times10^7$ copies/uL and used to generate a standard curve by plotting Ct value vs. the concentration of the HBV plasmid DNA standard. The quantity of HBV DNA in each sample was determined by interpolating from the standard curve.

Cell Viability

After harvest of the supernatants, the cell viability was detected by CellTiter-Glo® according to the manufacturer's manual. In brief, 50 μL of fresh cell culture medium was added to the culture plates, followed by addition of 50 μL CellTiter-Glo into each well. The plates were incubated at room temperature for 10 mins. The luminescence signal was collected on a BioTek Synergy 2 plate reader.

Data Analysis

Cell viability was calculated as follows: % Cell viability=(luminescence value of test sample−average luminescence value of blank)/(average luminescence value of 0.5% DMSO control−average luminescence of blank)×100%. HBV DNA inhibition was calculated as follows: 100−(HBV DNA copy number of test sample−HBV DNA copy number of ETV)/HBV DNA copy number of 0.5% DMSO control−HBV DNA copy number of ETV)×100%. The $CC_{50}$, $EC_{50}$ and $EC_{90}$ values were determined by dose-response curves fitted by GraphPad Prism using "log (agonist) vs. response—Variable slope".

Compounds of Formula (I) are active against HBV as shown in Table 2, where 'A' indicates an $EC_{50}$<1 nM, 'B' indicates an $EC_{50}$ of ≥1 nM and <10 nM, 'C' indicates an $EC_{50}$≥10 nM and <100 nM, 'D' indicates an $EC_{50}$≥100 nM and <1000 nM, and 'E' indicates an $EC_{50}$>1000 nM.

TABLE 2

Activity of compounds

| No. | $EC_{50}$ |
|---|---|
| 1 | B |
| 2 | B |
| 3 | E |
| 4 | B |
| 5 | C |
| 6 | D |
| 7 | D |
| 8 | C |
| 9 | B |
| 10 | C |
| 11 | A |
| 12 | D |
| 13 | B |
| 14 | A |
| 15 | A |
| 16 | C |
| 17a | B |
| 17b | B |
| 18 | B |
| 19 | A |
| 20 | C |
| 21 | B |
| 22 | B |
| 23a | A |
| 23b | A |
| 24 | A |
| 25 | D |
| 26 | A |
| 27 | C |
| 28a | B |
| 28b | B |
| 29 | B |
| 30a | A |
| 30b | A |
| 31a | B |
| 31b | B |
| 32 | B |
| 33 | B |
| 34 | A |
| 35 | A |
| 36a | A |
| 36b | A |
| 37 | A |
| 38a | A |
| 38b | A |
| 39 | A |
| 40 | A |
| 41 | B |
| 49 | A |
| 50 | A |
| 51 | A |
| 52 | A |
| 53 | B |

TABLE 2-continued

| Activity of compounds | |
|---|---|
| No. | $EC_{50}$ |
| 55 | A |
| 56 | A |
| 57 | A |
| 58 | B |
| 61a | B |
| 61b | B |
| 62 | D |
| 63a | B |
| 63b | B |
| 64a | B |
| 64b | B |
| 65a | A |
| 65b | B |
| 66a | A |
| 66b | B |
| 67 | C |
| 68 | A |
| 69a | B |
| 69b | B |
| 70 | B |
| 71a | B |
| 71b | B |
| 72a | B |
| 72b | B |
| 74a | B |
| 75b | C |
| 76a | B |
| 76b | B |
| 76 | C |
| 79a | B |
| 79b | B |
| 80a | B |
| 80b | B |
| 81 | B |
| 82 | B |
| 83 | B |
| 84 | B |
| 85 | B |
| 86 | B |
| 87 | B |
| 88 | B |
| 89 | B |
| 90 | B |
| 91 | B |
| 92 | B |
| 93 | B |
| 94a | C |
| 94b | B |
| 95a | B |
| 95b | B |
| 96 | B |
| 97 | A |
| 98 | A |
| 99 | B |

TABLE 2-continued

| Activity of compounds | |
|---|---|
| No. | $EC_{50}$ |
| 100 | A |
| 101 | B |
| 102 | B |
| 103 | B |
| 104 | B |
| 105 | B |
| 106 | B |
| 107 | B |
| 108 | B |
| 109 | B |
| 131 | B |
| 132 | B |
| 133 | B |
| 134 | B |
| 135 | B |
| 136 | B |
| 137 | B |
| 138 | B |
| 139 | B |
| 140 | B |
| 141 | B |
| 142 | B |
| 143 | B |
| 144 | B |
| 145 | B |
| 146 | B |
| 147 | B |
| 148 | B |
| 149 | D |
| 150 | A |
| 151 | B |
| 152 | B |
| 153 | A |
| 155 | B |
| 156 | A |
| 157 | B |
| 158 | A |
| 159 | B |
| 160 | B |
| 161 | B |
| 162 | B |

Although the foregoing has been described in some detail by way of illustrations and examples for purposes of clarity and understanding, it will be understood by those of skill in the art that numerous and various modifications can be made without departing from the spirit of the present disclosure. Therefore, it should be clearly understood that the forms disclosed herein are illustrative only and are not intended to limit the scope of the present disclosure, but rather to also cover all modification and alternatives coming with the true scope and spirit of the invention.

What is claimed is:

1. A compound having the structure

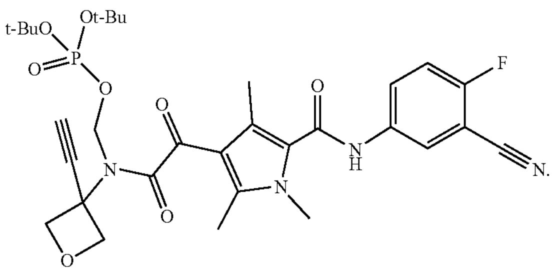 [SMILES: C#CC1(N(COP(=O)(OC(C)(C)C)OC(C)(C)C)C(=O)C(=O)c2c(C)c(C(=O)Nc3ccc(F)c(C#N)c3)n(C)c2C)COC1]

2. A compound having the structure

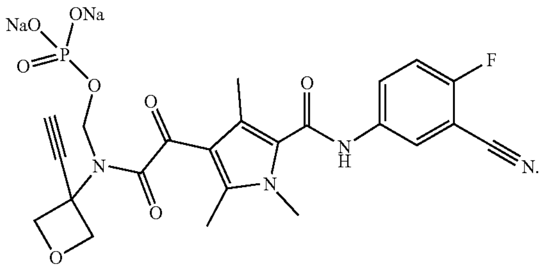

* * * * *